United States Patent [19]

Hemmi et al.

[11] Patent Number: 5,430,022

[45] Date of Patent: * Jul. 4, 1995

[54] PEPTIDE COMPOUND AND ITS PREPARATION

[75] Inventors: Keiji Hemmi, Tsukuba; Masahiro Neya, Tsuchiura; Naoki Fukami, Ibaraki; Masashi Hashimoto, Toride; Hirokazu Tanaka, Tsuchiura; Natsuko Kayakiri, Tsukuba, all of Japan

[73] Assignee: Fujisawa Pharmaceutical Co., Ltd., Osaka, Japan

[*] Notice: The portion of the term of this patent subsequent to Feb. 8, 2011 has been disclaimed.

[21] Appl. No.: 86,094

[22] Filed: Jul. 6, 1993

Related U.S. Application Data

[63] Continuation of Ser. No. 845,056, Mar. 3, 1992, abandoned, which is a continuation-in-part of Ser. No. 753,997, Sep. 3, 1991, abandoned, which is a continuation-in-part of Ser. No. 696,701, May 7, 1991, Pat. No. 5,284,828.

[30] Foreign Application Priority Data

May 14, 1990 [GB] United Kingdom ............ 9010740
Dec. 3, 1990 [GB] United Kingdom ............ 9026254
Feb. 27, 1991 [GB] United Kingdom ............ 9104064

[51] Int. Cl.⁶ .............. A61K 38/06; C07K 1/02; C07K 1/06; C07K 5/08
[52] U.S. Cl. ...................... 514/18; 530/331
[58] Field of Search ............ 530/331; 514/18

[56] References Cited

U.S. PATENT DOCUMENTS 4,048,305  9/1977  Molteni et al. ............ 530/331
4,127,534  11/1978  Coy et al. ................... 514/18

(List continued on next page.)

FOREIGN PATENT DOCUMENTS 0018072  10/1980  European Pat. Off.
0183245  6/1986   European Pat. Off.
333174   9/1989   European Pat. Off. ........ 514/18
0460679  12/1991  European Pat. Off.

OTHER PUBLICATIONS

Annalen der Chemie, vol. 683, issued 1965, Barth, "Synthese Von Oi-Und Tripeptiden Mittels . . . ", pp. 216–224.

(List continued on next page.)

Primary Examiner—Jeffrey E. Russel
Attorney, Agent, or Firm—Oblon, Spivak, McClelland, Maier, & Neustadt

[57] ABSTRACT

Peptide compounds of the formula (I')

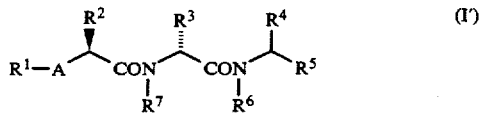

in which
 $R^1$ is acyl,
 $R^2$ is lower alkyl, cyclo(lower)alkyl(lower)alkyl or optionally substituted heterocyclic(lower)alkyl,
 $R^3$ is optionally substituted heterocyclic(lower)alkyl or optionally substituted ar(lower)alkyl,
 $R^4$ is lower alkyl, amino(lower)alkyl, protected amino(lower)alkyl, carboxy(lower)alkyl, protected carboxy(lower)alkyl or optionally substituted heterocyclic(lower)alkyl,
 $R^5$ is carboxy, protected carboxy, carboxy(lower)alkyl or protected carboxy(lower)alkyl,
 $R^6$ is hydrogen, lower alkyl, $C_{6\text{-}10}$ar(lower)alkyl amino(lower)alkyl, protected amino(lower)alkyl, carboxy(lower)alkyl, protected carboxy(lower)alkyl, or heterocyclic(lower)alkyl,
 $R^7$ is hydrogen or lower alkyl, and
 A is —O—, —NH—, lower alkylimino or lower alkylene, or a pharmaceutically acceptable salt thereof are disclosed. The compounds can be used to treat and prevent endothelin mediated diseases such as hypertension. The preparation of such peptides is also disclosed.

12 Claims, No Drawings

U.S. PATENT DOCUMENTS

| | | | |
|---|---|---|---|
| 4,228,156 | 10/1980 | Momany | 530/331 |
| 4,921,855 | 5/1990 | Hemmi et al. | 514/235.8 |
| 4,963,530 | 10/1990 | Hemmi et al. | 514/19 |
| 5,223,489 | 6/1993 | Hemmi et al. | 514/19 |
| 5,284,828 | 2/1994 | Hemmi et al. | 514/18 |

OTHER PUBLICATIONS

Biochemical and Biophysical Research Communications, vol. 156, No. 3, Nov. 15, 1988, pp. 1182–1186, Sadao Kimura, et al., "Structure–Activity Relationships of Endothelin: Importance of the C–Terminal Moiety".

Bulletin of the Chemical Society of Japan, vol. 43, No. 4, Apr. 1970, pp. 1197–1202, Shuji Matsuura, et al., "Studies of Peptide Antibiotics. XVI. Analogs of Gramicidin S Containing β–Alanine in Place of L–Proline".

Bulletin of the Chemical Society of Japan, vol. 39, No. 8, Aug. 1966, pp. 1747–1753, Haruhiko Aoyagi, et al., "Studies of Peptide Antibiotics. V. Syntheses of Cyclic Penta– and Decapeptides with the L–Valyl–L–Ornithyl–Leucyl–D–Phenylalanylsarcosyl Sequence".

PEPTIDE COMPOUND AND ITS PREPARATION

This is a continuation of application Ser. No. 07/845,056, filed on Mar. 3, 1992, now abandoned, which is a CIP of 07/753,997, filed on Sep. 3, 1991, now abandoned, which is a CIP of 07/696,701, filed on May 7, 1991, now U.S. Pat. No. 5,289,828.

The present invention relates to new peptide compound and a pharmaceutically acceptable salt thereof.

More particularly, it relates to new peptide compound and a pharmaceutically acceptable salt thereof which have pharmacological activities such as endothelin antagonistic activity and the like, to processes for its preparation, to a pharmaceutical composition comprising the same, and to a method of using the same therapeutically in the treatment and the prevention of endothelin mediated diseases such as hypertension, and the like.

One object of the present invention is to provide new and useful peptide compound and a pharmaceutically acceptable salt thereof which have pharmacological activities such as endothelin antagonistic activity and the like.

Another object of the present invention is to provide processes for the preparation of said peptide compound and a salt thereof.

A further object of the present invention is to provide a pharmaceutical composition comprising, as an active ingredient, said peptide compound or a pharmaceutically acceptable salt thereof.

Still further object of the present invention is to provide a method of using the same for the treatment and the prevention of endothelin mediated diseases such as hypertension, and the like.

The object compound of the present invention can be represented by the following general formula (I).

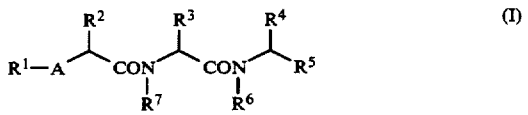

(I)

in which
R$^1$ is hydrogen or acyl,
R$^2$ is lower alkyl, optionally substituted ar(lower)alkyl, cyclo(lower)alkyl(lower)alkyl or optionally substituted heterocyclic(lower)alkyl,
R$^3$ is optionally substituted heterocyclic(lower)alkyl or optionally substituted ar(lower)alkyl,
R$^4$ is hydrogen or optionally substituted lower alkyl,
R$^5$ is carboxy, protected carboxy, carboxy(lower)alkyl or protected carboxy(lower)alkyl,
R is hydrogen or optionally substituted lower alkyl,
R$^7$ is hydrogen or lower alkyl, and
A is —O—, —NH—, lower alkylimino or lower alkylene,
provided that when R$^2$ is (S)-isobutyl, R$^3$ is N-(dichlorobenzyloxycarbonyl)indol-3-ylmethyl, R$^4$ is methyl, R$^5$ is methoxycarbonyl, R$^6$ is hydrogen, R$^7$ is hydrogen and A is —NH—, then the partial formula:

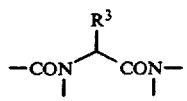

has the absolute configuration of

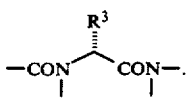

Particularly, the compound represented by the following formula (I') is more useful as an endothelin antagonist and the like.

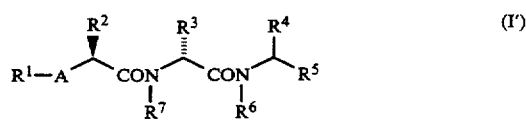

(I')

in which R$^1$, R$^2$, R$^3$, R$^4$, R$^5$, R$^6$, R$^7$ and A are each as defined above.

Further, the compound (I) having the most potent activities can be represented by the following formula.

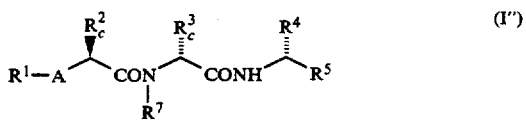

(I")

in which
R$^1$, R$^4$, R$^5$, R$^7$ and A are each as defined above, and
R$_c$$^2$ is lower alkyl and
R$_c$$^3$ is optionally N-substituted indolylmethyl.

According to the present invention, the new peptide compound (I) and a salt thereof can be prepared by the processes as shown in the following schemes.

Process 1

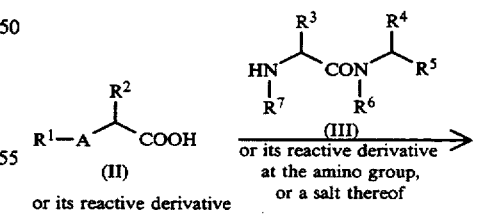

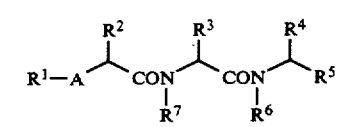

(I)

or a salt thereof

Process 2

-continued

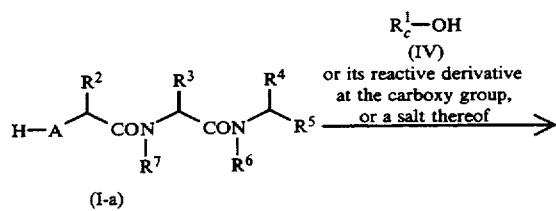

(I-a)
or its reactive derivative
at the amino group,
or a salt thereof

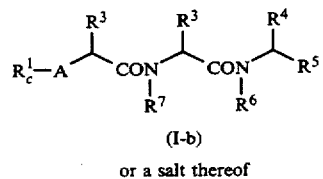

(I-b)
or a salt thereof

Process 3

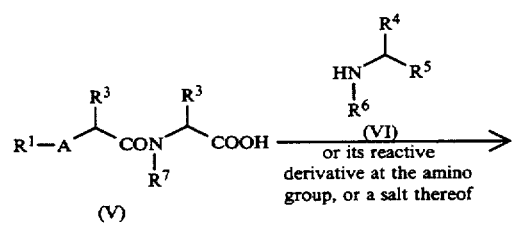

(V)
or its reactive derivative
at the carboxy group,
or a salt thereof

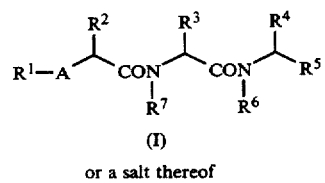

(I)
or a salt thereof

Process 4

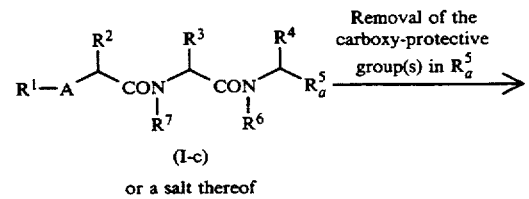

(I-c)
or a salt thereof

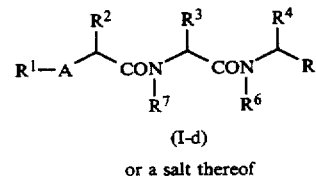

(I-d)
or a salt thereof

Process 5

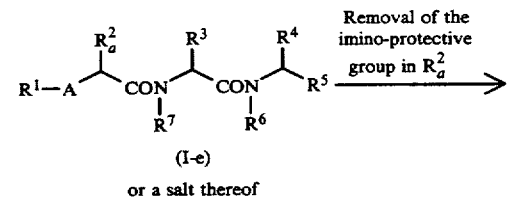

(I-e)
or a salt thereof

-continued

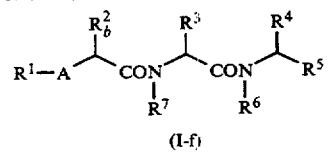

(I-f)
or a salt thereof

Process 6

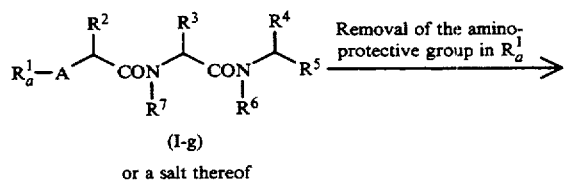

(I-g)
or a salt thereof

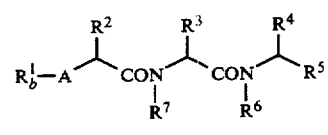

(I-h)
or a salt thereof

Process 7

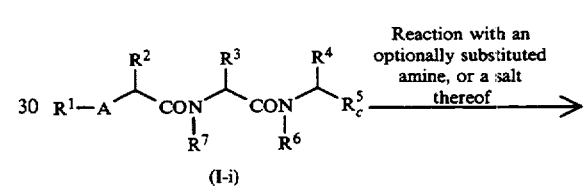

(I-i)
or its reactive derivative
at the carboxy group,
or a salt thereof

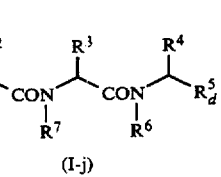

(I-j)
or a salt thereof

Process 8

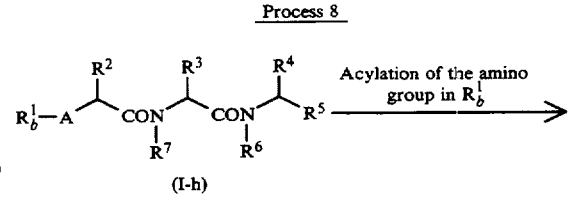

(I-h)
or a salt thereof

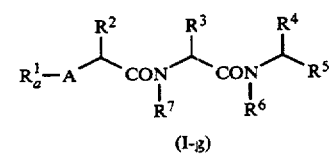

(I-g)
or a salt thereof

Process 9

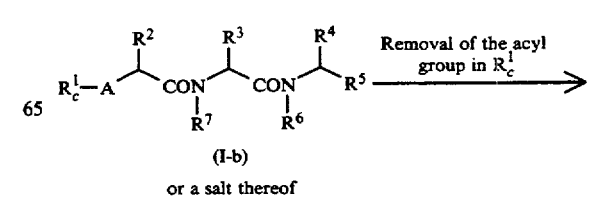

(I-b)
or a salt thereof

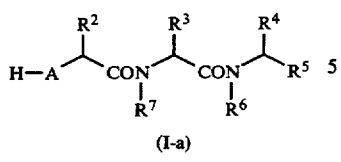

(I-a)

or a salt thereof

Process 10

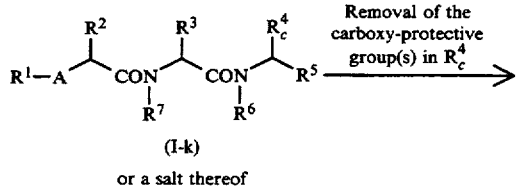

(I-k)

or a salt thereof

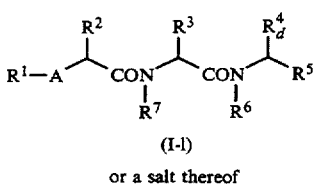

(I-l)

or a salt thereof

Process 11

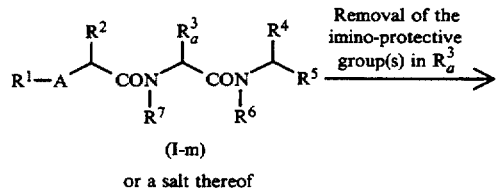

(I-m)

or a salt thereof

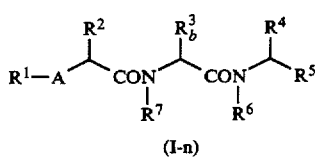

(I-n)

or a salt thereof

Process 12

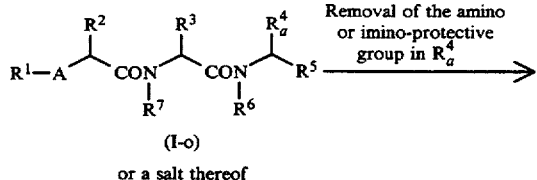

(I-o)

or a salt thereof

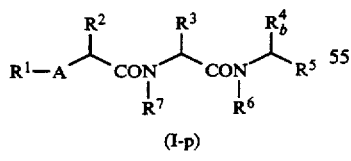

(I-p)

or a salt thereof in which $R^1$, $R^2$, $R^3$, $R^4$, $R^5$, $R^6$, $R^7$ and A are each as defined above, $R_a{}^1$ is acyl substituted by a protected amino group,
$R_b{}^1$ is acyl substituted by an amino group,
$R_c{}^1$ is acyl, $R_a{}^2$ and $R_a{}^3$ are each protected imino containing heterocyclic(lower)alkyl optionally substituted by suitable substituent(s), $R_a{}^4$ is protected amino(lower)alkyl or protected imino containing heterocyclic(lower)alkyl optionally substituted by suitable substituent(s), $R_b{}^2$ and $R_b{}^3$ are each imino containing heterocyclic(lower)alkyl optionally substituted by suitable substituent(s), $R_b{}^4$ is amino(lower)alkyl or imino containing heterocyclic(lower)alkyl optionally substituted by suitable substituent(s), $R_c{}^4$ is protected carboxy(lower)alkyl, $R_d{}^4$ is carboxy(lower)alkyl, $R_a{}^5$ is protected carboxy or protected carboxy(lower)alkyl, $R_b{}^5$ is carboxy or carboxy(lower)alkyl, $R_c{}^5$ is carboxy or esterified carboxy, and $R_d{}^5$ is amidated carboxy.

Some of the starting compounds used in the above Processes are novel and can be prepared according to the following Methods and/or by the procedures described in the following Preparations or by a conventional manner.

Method 1

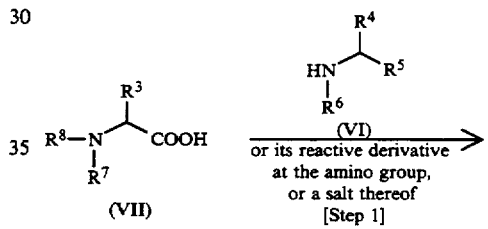

(VII)

or its reactive derivative at the carboxy group or a salt thereof

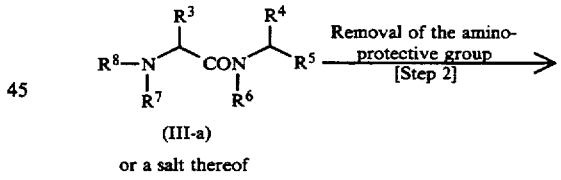

(III-a)

or a salt thereof

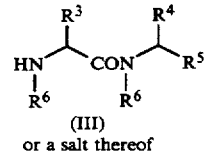

(III)

or a salt thereof

Method 2

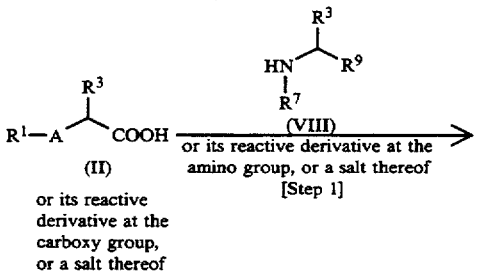

-continued

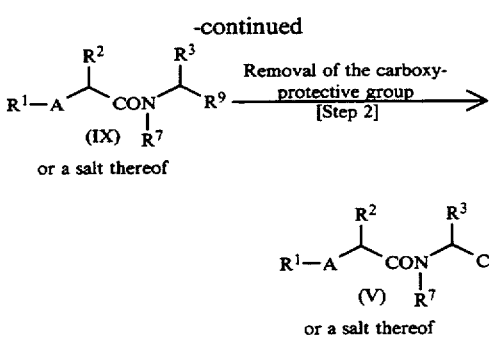

in which
R¹, R², R³, R⁴, R⁵, R⁶, R⁷ and A are each as defined above,
R⁸ is amino-protective group, and
R⁹ is protected carboxy.

Throughout the present specification, the amino acids, peptides, protective groups, condensing agents, etc. are indicated by the abbreviations according to the IUPAC-IUB (Commission on Biological Nomenclature) which are in common use in a field of this art.

Moreover, unless otherwise indicated, the amino acids and their residues when shown by such abbreviations are meant to be L-configured compounds and residues, while the D-configured compounds and residues are shown with the prescript of D-.

Suitable pharmaceutically acceptable salts of the object compound (I) may be a conventional non-toxic salt and include an acid addition salt such as an organic acid salt (e.g. acetate, trifluoroacetate, maleate, tartrate, fumarate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with a base such as an amino acid (e.g. arginine, aspartic acid, glutamic acid, etc.), an alkali metal salt (e.g. sodium salt, potassium salt, etc.), an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention includes within the scope thereof are explained in detail as follows.

The term "lower" is intended to mean 1 to 6, preferably 1 to 4 carbon atoms, and the term "higher" is intended to mean more than 6, preferably 7 to 12 carbon atoms, unless otherwise indicated.

Suitable "acyl" may include an aliphatic acyl, an aromatic acyl, a heterocyclic acyl and an aliphatic acyl substituted with aromatic or heterocyclic group(s) derived from acids such as carboxylic, carbonic, carbamic, sulfonic acids.

The aliphatic acyl may include saturated or unsaturated, acyclic or cyclic ones, such as carbamoyl, lower alkanoyl (e.g. formyl, acetyl, propionyl, butyryl, isobutyryl, 3,3-dimethylbutyryl, 4,4-dimethylvaleryl, valeryl, isovaleryl, pivaloyl, hexanoyl, 3-methylvaleryl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, t-butoxycarbonyl, etc.), lower alkenoyl (e.g. acryloyl, methacryloyl, crotonoyl, etc.), ($C_3$–$C_7$)cycloalkanecarbonyl (e.g. cyclohexanecarbonyl, etc.), ($C_3$–$C_7$)cycloalkyl(lower)alkanoyl (e.g. cyclohexylacetyl, etc.), amidino, protected carboxycarbonyl such as lower alkoxalyl (e.g. methoxalyl, ethoxalyl, t-butoxalyl, etc.), $C_3$–$C_7$ cycloalkyloxycarbonyl (e.g. cyclohexyloxycarbonyl, etc.), (heterocyclic acyl)(lower)alkanoyl, wherein said heterocyclic acyl being the same as those mentioned below, such as morpholinocarbonyl(lower)alkanoyl (e.g. 3-morpholinocarbonylpropanoyl, etc.), lower or higher alkylcarbamoyl (e.g. methylcarbamoyl, ethylcarbamoyl, propylcarbamoyl, isopropylcarbamoyl, butylcarbamoyl, 2-methylbutylcarbamoyl, pentylcarbamoyl, 1,3-dimethylbutylcarbamoyl hexylcarbamoyl, hepthylcarbamoyl, octylcarbamoyl, nonylcarbamoyl, etc.), di(lower)alkylcarbamoyl (e.g. N-methyl-N-ethylcarbamoyl, dimethylcarbamoyl, diethylcarbamoyl, dipropylcarbamoyl, diisopropylcarbamoyl, dibutylcarbamoyl, diisobutylcarbamoyl, dihexylcarbamoyl, etc.), $C_3$–$C_7$ cycloalkylcarbamoyl (e.g. cyclopropylcarbamoyl, cyclobutylcarbamoyl, cyclopentylcarbamoyl, cyclohexylcarbamoyl, cycloheptylcarbamoyl, etc.), N-lower alkyl-N-($C_3$–$C_7$)cycloalkylcarbamoyl (e.g. N-methyl-N-cyclopropylcarbamoyl, N-methyl-N-cyclohexylcarbamoyl, N-ethyl-N-cyclohexylcarbamoyl, N-propyl-N-hexylcarbamoyl, etc.), di($C_3$–$C_7$)cycloalkylcarbamoyl (e.g. dicyclopropylcarbamoyl, dicyclopentylcarbamoyl, dicyclohexylcarbamoyl, etc.), N-[di(lower)alkylcarbamoyl($C_3$–$C_7$)cycloalkyl]carbamoyl [e.g. N-(1-(or 4-)dimethylcarbamoylcyclohexyl)carbamoyl, etc.], N-[di(lower)alkylcarbamoyl(lower)alkyl($C_3$–$C_7$)cycloalkyl]carbamoyl [e.g. N-[1-(or 4-)(dimethylcarbamoylmethyl)cyclohexyl]carbamoyl, etc.], N-[carbamoyl(lower)alkyl]carbamoyl [e.g. N-[1-carbamoyl-2-methylbutyl]-carbamoyl, etc.], N-[N-(lower)alkylcarbamoyl(lower)alkyl]carbamoyl [e.g. N-(1-isopropylcarbamoyl-2-methylbutyl)carbamoyl, etc.], N-[N,N-lower alkylenecarbamoyl(lower)alkyl]carbamoyl [e.g. N-[2-methyl-1-(piperidinocarbonyl)butyl]carbamoyl, etc.], N-[N,N-di(lower)alkylcarbamoyl(lower)alkyl]carbamoyl [e.g. N-(dimethylcarbamoylmethyl)carbamoyl, N-[1-(or 2-)(dimethylcarbamoyl)ethyl]carbamoyl, N-[1-(dimethylcarbamoyl)-2-methylpropyl]carbamoyl, N-[2,2-dimethyl-1-(dimethylcarbamoyl)propyl]carbamoyl, N-[2-methyl-1-(dimethylcarbamoyl)butyl]carbamoyl, N-[2-methyl-1-(diethylcarbamoyl)butyl]carbamoyl, N-[3-methyl-1-(dimethylcarbamoyl)butyl]carbamoyl, N-(1-dimethylcarbamoylpentyl)carbamoyl, etc.], N-(lower)alkyl-N-[N,N-di(lower)alkylcarbamoyl]-(lower)alkylcarbamoyl [e.g. N-methyl-N-[1-dimethylcarbamoyl- 2-methylbutyl]carbamoyl, N-methyl-N-[1-dimethylcarbamoyl-3-methylbutyl]carbamoyl, etc.], N-[N-(lower)cycloalkylcarbamoyl(lower)alkyl]carbamoyl [e.g. N-(1-cyclohexylcarbamoyl-2-methylbutyl)carbamoyl, etc.], and the like.

The aromatic acyl may include ($C_6$–$C_{10}$)aroyl (e.g. benzoyl, toluoyl, xyloyl, naphthoyl, etc.), ($C_6$–$C_{10}$)arenesulfonyl (e.g. benzenesulfonyl, tosyl, etc.), ($C_6$–$C_{10}$)arylcarbamoyl (e.g. phenylcarbamoyl, tolylcarbamoyl, etc.), ($C_6$–$C_{10}$)aryloxalyl (e.g. phenyloxalyl, etc.), and the like.

The heterocyclic acyl, wherein said heterocyclic group may be the same as mentioned below, may include heterocyclecarbonyl (e.g. furoyl, thenoyl, 2-(or 3- or 4-)pyridylcarbonyl, thiazolylcarbonyl, thiadiazolylcarbonyl, tetrazolylcarbonyl, piperazinylcarbonyl, morpholinocarbonyl, thiomorpholinocarbonyl, indolylcarbonyl, etc.), lower or higher alkyleneaminocarbonyl (e.g. aziridin-1-ylcarbonyl, azetidn-1-ylcarbonyl, pyrrolidin-1-ylcarbonyl, piperidin-1-ylcarbonyl, hexahydro-1H-azepin-1-ylcarbonyl, octahydroazocin-1-ylcarbonyl, tetrahydroquinolinecarbonyl, tetrahydroisoquinolinecarbonyl, dihydropyridinecarbonyl, tetrahydropyridinecarbonyl, etc.), heterocyclic-carbamoyl wherein said heterocyclic group may be the same as mentioned below (e.g. pyridylcarbamoyl, piperidylcarbamoyl, hexahydro-1H-azepinylcarbamoyl, etc.), and the like.

The aliphatic acyl substituted with aromatic group(s) may include ($C_6$–$C_{10}$)ar(lower)alkanoyl such as phenyl(lower)alkanoyl (e.g. phenylacetyl, phenylpropionyl, phenylhexanoyl, naphthylacetyl etc.), ($C_6$–$C_{10}$)ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), ($C_6$–$C_{10}$)ar(lower)alkoxalyl such as phenyl(lower)alkoxalyl (e.g. benzyloxalyl etc.), ($C_6$–$C_{10}$)ar(lower)alkenoyl such as phenyl(lower)alkenoyl (e.g. cinnamoyl, etc.), ($C_6$–$C_{10}$)ar(lower)alkylsulfonyl (e.g. benzylsulfonyl, etc.), and the like.

The aliphatic acyl substituted with heterocyclic group(s) may include heterocyclic(lower)alkanoyl, wherein said heterocyclic group may be the same as mentioned below (e.g. thienylacetyl, imidazolylacetyl, furylacetyl, tetrazolylacetyl, thiazolylacetyl, thiadiazolylacetyl, thienylpropionyl, thiadiazolylpropionyl, pyridylacetyl, etc.), heterocyclic-lower alkylcarbamoyl, wherein said heterocyclic group may be the same as mentioned below (e.g. pyridylmethylcarbamoyl, morpholinoethylcarbamoyl, etc.), and the like.

These acyl groups may be further substituted with one or more, preferably one to three suitable substituent(s) such as hydroxy, lower alkyl (e.g. methyl, ethyl, propyl, isopropyl, butyl, t-butyl, pentyl, hexyl, etc.), halogen (e.g. chlorine, bromine, iodine, fluorine), carbamoyl, oxo, di(lower)alkylcarbamoyl, amino, protected amino such as lower alkanoylamino (e.g. formamido, acetamido, propionamido, etc.), lower alkoxycarbonylamino (e.g. t-butoxycarbonylamino, etc.), lower alkylsulfonyl (e.g. methylsulfonyl, etc.), arylsulfonyl (e.g. phenylsulfonyl, tosyl, etc.), ar(lower)alkyl (e.g. benzyl, etc.), lower alkoxy (e.g. methoxy, ethoxy, propoxy, isopropoxy, butoxy, t-butoxy, etc.], carboxy, protected carboxy as mentioned below, carboxy(lower)alkyl (e.g. carboxymethyl, carboxyethyl, etc.), protected carboxy(lower)alkyl (e.g. t-butoxycarbonylmethyl, etc.) and the like.

Suitable examples of the above acyl groups which is further substituted with one or more, preferably one to three suitable substituent(s) may be halophenyl(lower)alkanoyl (e.g., 2-chlorophenylacetyl, etc.), (aminophenyl)(lower)alkanoyl (e.g. 4-aminophenylacetyl, etc.), [(lower alkoxycarbonylamino)phenyl](lower)alkanoyl [e.g. 4-(t-butoxycarbonylamino)phenylacetyl, etc.], amino(lower)alkanoyl (e.g. 2-amino-3-methylpentanoyl, etc.), (lower alkoxycarbonylamino)(lower)alkanoyl [e.g. 2-(t-butoxycarbonylamino)-3-methylpentanoyl, etc.), lower alkanoyl substituted by suitable substituent(s) such as phenyl, amino, lower alkoxycarbonylamino, etc. [e.g. 2-amino-2-phenylacetyl, 2-(t-butoxycarbonylamino)-2-phenylacetyl, etc.], di(lower)alkylpiperidinylcarbonyl [e.g. 2,6-(or 3,5-)dimethylpyperidin-1-ylcarbonyl, etc.], [di(lower)alkylcarbamoyl]piperidinylcarbonyl [e.g. 4-(dimethylcarbamoyl)piperidin-1-ylcarbonyl, etc.], [di(lower)alkylcarbamoyl]pyrrolidinylcarbonyl [e.g. 2-(dimethylcarbamoyl)pyrrolidin-1-ylcarbonyl, etc.], piperazinylcarbonyl substituted by suitable substituent(s) such as lower alkyl, oxo, etc. [e.g. 4-methyl-3-oxo-2-(1-methylpropyl)piperazin-1-ylcarbonyl, etc.], N-(lower)alkyl-N-[hydroxy(lower)alkyl]carbamoyl [e.g. N-methyl-N-(2-hydroxyethyl)carbamoyl, etc.], N-[hydroxy(lower)alkyl]carbamoyl [e.g. N-{1-(hydroxymethyl)-3-methylbutyl}carbamoyl, etc.], N-[($C_3$–$C_7$)cycloalkyl(lower)alkyl]carbamoyl [e.g. N-(cyclohexylmethyl)carbamoyl, etc.], N-[carboxy(lower)alkyl]carbamoyl [e.g. N-(1-carboxy-2-methylbutyl)carbamoyl, etc.], N-[(lower)alkoxycarbonyl(lower)alkyl]carbamoyl [e.g. N-(1-methoxycarbonyl-2-methylbutyl)carbamoyl, etc.], (oxoheterocyclic)carbamoyl wherein said heterocyclic group may be the same as mentioned below such as {oxo(hexahydro-1H-azepinyl)}carbamoyl (e.g. ε-caprolactam-3-yl, etc.), etc., N-[N-(lower)alkoxycarbonylpiperidinyl]carbamoyl [e.g. N-(N-ethoxycarbonylpiperidin-4-yl)carbamoyl, etc.], N-[N,N-di(lower)alkylcarbamoyl(lower)alkyl]carbamoyl substituted by phenyl or cyclo(lower)alkyl [e.g. N-{1-(N,N-dimethylcarbamoyl)-1-phenylmethyl}carbamoyl, N-{1-(N,N-dimethylcarbamoyl)-1-cyclohexylmethyl}carbamoyl, etc.], N-[hydroxy($C_3$–$C_7$)cycloalkyl]carbamoyl [e.g. N-(4-hydroxycyclohexyl)carbamoyl, etc.], N-(lower)alkoxyphenylcarbamoyl [e.g. N-(4-methoxyphenyl)carbamoyl, etc.], N-(lower alkanoylamino)carbamoyl [e.g. N-(2-methylpropanoylamino)carbamoyl, etc.], and the like.

Preferable example of acyl may be carbamoyl, lower alkanoyl (e.g. formyl, acetyl, propionyl, butyryl, isobutyryl, 3,3-dimethylbutyryl, 4,4-dimethylvaleryl, valeryl, isovaleryl, pivaloyl, hexanoyl, 3-methylvaleryl, etc.), lower alkoxycarbonyl (e.g. methoxycarbonyl, ethoxycarbonyl, propoxycarbonyl, butoxycarbonyl, t-butoxycarbonyl, etc.), lower alkenoyl (e.g. acryloyl, methacryloyl, crotonoyl, etc.), ($C_3$–$C_7$)cycloalkanecarbonyl (e.g. cyclohexanecarbonyl, etc.), ($C_3$–$C_7$)cycloalkyl(lower)alkanoyl (e.g. cyclohexylacetyl, etc.), $C_3$–$C_7$ cycloalkyloxycarbonyl (e.g. cyclohexyloxycarbonyl, etc.), morpholinocarbonyl(lower)alkanoyl (e.g. 3-morpholinocarbonylpropanoyl, etc.), lower or higher alkylcarbamoyl (e.g. methylcarbamoyl, ethylcarbamoyl, propylcarbamoyl, isopropylcarbamoyl, butylcarbamoyl, 2-methylbutylcarbamoyl, pentylcarbamoyl, 1,3-dimethylbutylcarbamoyl hexylcarbamoyl, hepthylcarbamoyl, octylcarbamoyl, nonylcarbamoyl, etc.), di(lower)alkylcarbamoyl (e.g. N-methyl-N-ethylcarbamoyl, dimethylcarbamoyl, diethylcarbamoyl, dipropylcarbamoyl, diisopropylcarbamoyl, dibutylcarbamoyl, diisobutylcarbamoyl, dihexylcarbamoyl, etc.), $C_3$–$C_7$ cycloalkylcarbamoyl (e.g. cyclopropylcarbamoyl, cyclobutylcarbamoyl, cyclopentylcarbamoyl, cyclohexylcarbamoyl, cycloheptylcarbamoyl, etc.), N-lower alkyl-N-($C_3$–$C_7$)cycloalkylcarbamoyl (e.g. N-methyl-N-cyclopropylcarbamoyl, N-methyl-N-cyclohexylcarbamoyl, N-ethyl-N-cyclohexylcarbamoyl, N-propyl-N-cyclohexylcarbamoyl, etc.), di($C_3$–$C_7$)cycloalkylcarbamoyl (e.g. dicyclopropylcarbamoyl, dicyclopentylcarbamoyl, dicyclohexylcarbamoyl, etc.), N-[di(lower)alkylcarbamoyl ($C_3$–$C_7$)cycloalkyl]carbamoyl [e.g. N-(1-(or 4-)dimethylcarbamoylcyclohexyl)carbamoyl, etc.], N-[di(lower)alkylcarbamoyl(lower)alkyl($C_3$–$C_7$)cycloalkyl]carbamoyl [e.g. N-[1-(or 4-)(dimethylcarbamoylmethyl)cyclohexyl]carbamoyl, etc.], N-[carbamoyl(lower)alkyl]carbamoyl [e.g. N-[1-carbamoyl-2-methylbutyl]carbamoyl, etc.], N-[N-(lower)alkylcarbamoyl(lower)alkyl]carbamoyl [e.g. N-(1-isopropylcarbamoyl-2-methylbutyl)carbamoyl, etc.], N-[N,N-lower alkylenecarbamoyl(lower)alkyl]carbamoyl [e.g. N-[2-methyl-1-(piperidinocarbonyl)butyl]carbamoyl, etc.], N-[N,N-di(lower)alkylcarbamoyl(lower)alkyl]carbamoyl [e.g. N-(dimethylcarbamoylmethyl)carbamoyl, N-[1-(or 2-)(dimethylcarbamoyl)ethyl]carbamoyl, N-[1-(dimethylcarbamoyl)-2-methylpropyl]carbamoyl, N-[2,2-dimethyl-1-(dimethylcarbamoyl)propyl]carbamoyl, N-[2-methyl-1-(dimethylcarbamoyl)butyl]carbamoyl, N-[2-methyl-1-(diethylcarbamoyl)butyl]carbamoyl, N-[3-methyl-1-(dimethylcarbamoyl)butyl]carbamoyl, N-(1-dimethylcarbamoylpentyl)carbamoyl, etc.], N-(lower)alkyl-N-[N,N-di(lower)alkylcarbamoyl]-(lower)alkylcarbamoyl [e.g. N-methyl-N-[1-dimethylcarbamoyl-2-methylbutyl]carbamoyl, N-methyl-N-[1-dimethylcarbamoyl-3-methylbutyl]carbamoyl, etc.], N-[N-(lower)cycloalkylcarbamoyl(lower)alkyl]carbamoyl [e.g. N-(1-cyclohexylcarbamoyl-2-methylbutyl)carbamoyl, etc.], ($C_6$–$C_{10}$)aroyl (e.g. benzoyl, toluoyl, xyloyl, naphtoyl, etc.), ($C_6$–$C_{10}$)arylcarbamoyl (e.g. phenylcarbamoyl, tolylcarbamoyl, etc.), ($C_6$–$C_{10}$)aryloxalyl (e.g. phenyloxalyl, etc.), furoyl, thenoyl, 2-(or 3- or 4-)pyridylcarbonyl, thiazolylcarbonyl, thiadiazolylcarbonyl, tetrazolylcarbonyl, piperazinylcarbonyl, morpholinocarbonyl, thiomorpholinocarbonyl, indolylcarbonyl, lower alkyleneaminocarbonyl (e.g. aziridin-1-ylcarbonyl, azetidin-1-ylcarbonyl, pyrrolidin-1-ylcarbonyl, piperidin-1-ylcarbonyl, hexahydro-1H-azepin-1-ylcarbonyl, octahydroazocin-1-ylcarbonyl, tetrahydroquinolinecarbonyl, tetrahydroisoquinolinecarbonyl, dihydropyridinecarbonyl, tetrahydropyridinecarbonyl, etc.), pyridylcarbamoyl, piperidylcarbamoyl, hexahydro-1H-azepinylcarbamoyl, ($C_6$–$C_{10}$)ar(lower)alkanoyl such as phenyl(lower)alkanoyl (e.g. phenylacetyl, phenylpropionyl, phenylhexanoyl, naphthylacetyl, etc.), ($C_6$–$C_{10}$)ar(lower)alkoxycarbonyl such as phenyl(lower)alkoxycarbonyl (e.g. benzyloxycarbonyl, phenethyloxycarbonyl, etc.), ($C_6$–$C_{10}$)ar(lower)alkoxalyl such as phenyl(lower)alkoxalyl (e.g. benzyloxalyl etc.), ($C_6$–$C_{10}$)ar(lower)alkenoyl such as phenyl(lower)alkenoyl (e.g. cinnamoyl, etc.), ($C_6$–$C_{10}$)ar(lower)alkylsulfonyl (e.g. benzylsulfonyl, etc.), thienylacetyl, imidazolylacetyl, furylacetyl, tetrazolylacetyl, thiazolylacetyl, thiadiazolylacetyl, thienylpropionyl, thiadiazolylpropionyl, pyridylacetyl, pyridylmethylcarbamoyl, morpholinoethylcarbamoyl, halophenyl(lower)alkanoyl (e.g. 2-chlorophenylacetyl, etc.), (aminophenyl)(lower)alkanoyl (e.g. 4-aminophenylacetyl, etc.), [(lower alkoxycarbonylamino)-phenyl](lower)alkanoyl [e.g. 4-(t-butoxycarbonylamino)phenylacetyl, etc.], amino(lower)alkanoyl (e.g. 2-amino-3-methylpentanoyl, etc.), (lower alkoxycarbonylamino)(lower)alkanoyl [e.g. 2-(t-butoxycarbonylamino)-3-methylpentanoyl, etc.], lower alkanoyl substituted by suitable substituent(s) such as phenyl, amino, lower alkoxycarbonylamino [e.g. 2-amino-2-phenylacetyl, 2-(t-butoxycarbonylamino)-2-phenylacetyl, etc.], etc., di(lower)alkylpiperidinylcarbonyl [e.g. 2,6-(or 3,5-)dimethylpiperidin-1-ylcarbonyl, etc.], [di(-lower)alkylcarbamoyl]piperidinylcarbonyl [e.g. 4-(dimethylcarbamoyl)piperidin-1-ylcarbonyl, etc.], [di(-lower)alkylcarbamoyl]pyrrolidinylcarbonyl [e.g. 2-(dimethylcarbamoyl)pyrrolidin-1-ylcarbonyl, etc.], piperazinylcarbonyl substituted by suitable substituent(s) such as lower alkyl, oxo, etc. [e.g. 4-methyl-3-oxo-2-(1-methylpropyl)piperazin-1-ylcarbonyl, etc.], N-(lower)alkyl-N-[hydroxy(lower)alkyl]carbamoyl [e.g. N-methyl-N-(2-hydroxyethyl)carbamoyl, etc.], N-[hydroxy(lower)alkyl]carbamoyl [e.g. N-{1-(hydroxymethyl)-3-methylbutyl}carbamoyl, etc.], N-[($C_3$–$C_7$-)cycloalkyl(lower)alkyl]carbamoyl [e.g. N-(cyclohexylmethyl)carbamoyl, etc.], N-[carboxy(lower)alkyl]carbamoyl [e.g. N-(1-carboxy-2-methylbutyl)carbamoyl, etc.], N-[(lower)alkoxycarbonyl(lower)alkyl]carbamoyl [e.g. N-(1-methoxycarbonyl-2-methylbutyl)carbamoyl, etc.], (oxoheterocyclic)carbamoyl such as {oxo(-hexahydro-1H-azepinyl)}carbamoyl (e.g. ε-caprolactam-3-yl, etc.), etc., N-[N-(lower)alkoxycarbonylpiperidinyl]carbamoyl [e.g. N-(N-ethoxycarbonylpiperidin-4-yl)carbamoyl, etc.], N-[N,N-di(lower)alkylcarbamoyl(lower)alkyl]carbamoyl substituted by phenyl or cyclo(lower)alkyl [e.g. N-{1-(N,N-dimethylcarbamoyl)-1-phenylmethyl}carbamoyl, N-{1-(N,N-dimethylcarbamoyl)-1-cyclohexylmethyl}carbamoyl, etc.], N-[hydroxy($C_3$–$C_7$)cycloalkyl]carbamoyl [e.g. N-(4-hydroxycyclohexyl)carbamoyl, etc.], N-(lower)alkoxyphenyl)carbamoyl [e.g. N-(4-methoxyphenyl)carbamoyl, etc.], N-(lower alkanoylamino)carbamoyl [e.g. N-(2-methylpropanoylamino)carbamoyl, etc.], and the like.

Suitable "lower alkyl" may include a straight or branched one such as methyl, ethyl, propyl, isopropyl, butyl, isobutyl, tert-butyl, pentyl, hexyl, and the like, in which the most preferred example may be isobutyl, 1-methylpropyl, n-butyl and 2,2-dimethylpropyl for $R^2$, and methyl for $R^7$.

Suitable "lower alkylene" may include a straight or branched one such as methylene, ethylene, propylene, trimethylene, tetramethylene, pentamethylene, hexamethylene, and the like, in which the most preferred example may be methylene.

Suitable "protected carboxy" may include esterified carboxy and amidated carboxy as mentioned above.

"Esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s) for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], aroyl(lower)alkyl ester such as benzoyl(lower)alkyl ester (e.g. phenacyl ester, etc.), lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], phthalidylidene(-lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

Preferable examples of the esterified carboxy thus defined may be lower alkoxycarbonyl, phenyl(lower)alkoxycarbonyl and benzoyl(lower)alkoxycarbonyl, and the most preferable one may be methoxycarbonyl, ethoxycarbonyl, benzyloxycarbonyl and phenacyloxycarbonyl.

Suitable "carboxy(lower)alkyl" means aforementioned lower alkyl which is substituted by carboxy, wherein the preferable examples may be carboxymethyl, carboxyethyl, carboxypropyl and carboxybutyl for $R^5$.

Suitable "protected carboxy(lower)alkyl" means aforementioned lower alkyl which is substituted by above-mentioned "protected carboxy", wherein more preferable example may be lower alkoxycarbonyl(lower)alkyl, phenyl(lower)alkoxycarbonyl(lower)alkyl and benzoyl(lower)alkoxycarbonyl(lower)alkyl, and the most preferable one may be methoxycarbonylmethyl, methoxycarbonylethyl, methoxycarbonylpropyl, methoxycarbonylbutyl, phenacyloxycarbonylmethyl, phenacyloxycarbonylethyl, phenacyloxycarbonylpropyl and phenacyloxycarbonylbutyl for $R^5$.

Said "amidated carboxy" can be referred to the ones as mentioned below.

Suitable examples of the amidated carboxy may include carbamoyl, mono(or di)(lower)alkylcarbamoyl wherein the lower alkyl group may be the same as those mentioned above (e.g. methylcarbamoyl, ethylcarbamoyl, isopropylcarbamoyl, butylcarbamoyl, 3-methylbutylcarbamoyl, isobutylcarbamoyl, pentylcarbamoyl, dimethylcarbamoyl, diethylcarbamoyl, etc.), and further said lower alkyl may be substituted by the group consisting of carboxy; protected carboxy as mentioned above such as lower alkoxycarbonyl (e.g. methoxycarbonyl, ethoxycarbonyl, etc.), ar(lower)alkoxycarbonyl, preferably phenyl(lower)alkoxycarbonyl (e.g. benzyloxycarbonyl, etc.), aroyl(lower)alkoxycarbonyl, preferably benzoyl(lower)alkoxycarbonyl (e.g. phenacyloxycarbonyl, etc.); aryl (e.g. phenyl, naphthyl, etc.); heterocyclic group as mentioned below such as saturated or unsaturated 5 or 6-membered heteromonocyclic group containing 1 to 4 nitrogen atom(s) (e.g. pyridyl, pyrrolidinyl, etc.), wherein said heterocyclic group may be further substituted by suitable substituent(s) such as oxo, carboxy, protected carboxy as mentioned above and carbamoyl, for example, oxopyrrolidinyl substituted by carboxy, lower alkoxycarbonyl or carbamoyl [e.g. 2-oxo-5-carboxypyrrolidinyl, 2-oxo-5-ethoxycarbonylpyrrolidinyl, 2-oxo-5-carbamoylpyrrolidinyl, etc.); $C_3$–$C_7$ cycloalkyl optionally substituted by carboxy or protected carboxy as mentioned above such as lower alkoxycarbonyl (e.g. carboxycyclohexyl, ethoxycarbonylcyclohexyl, etc.);

($C_3$–$C_7$)cycloalkylcarbamoyl (e.g. cyclohexylcarbamoyl, etc.), carbamoyl substituted by amino or di(lower)alkylamino [e.g. N-aminocarbamoyl, N-(dimethylamino)carbamoyl, etc.], N-(optionally substituted heterocyclic)carbamoyl wherein the heterocyclic moiety is the same as those mentioned above such as saturated 5 or 6-membered heteromonocyclic group containing 1 to 2 oxygen atom(s) and 1 to 3 nitrogen atom(s), unsaturated 5 or 6-membered heteromonocyclic group containing 1 to 2 sulfur atom(s) and 1 to 3 nitrogen atom(s), unsaturated condensed 7 to 12-membered heterocyclic group containing 1 to 2 sulfur atom(s) and 1 to 3 nitrogen atom(s), each of said heterocyclic group may be substituted by suitable substituent(s) such as hydroxy, protected hydroxy, halogen, lower alkoxy, lower alkyl, amino, nitro and cyano, for example, thiazolylcarbamoyl, benzothiazolylcarbamoyl, morpholinocarbamoyl, N-(lower alkylthiadiazolyl)carbamoyl (e.g. methylthiadiazolylcarbamoyl, etc.), lower alkyleneaminocarbonyl (e.g. pyrrolidin-1-ylcarbonyl, hexahydro-1H-azepin-1-ylcarbonyl, etc.), said alkylene being optionally substituted by carboxy or protected carboxy as mentioned above such as lower alkoxycarbonyl [e.g. carboxypyrrolidin-1-ylcarbonyl, (methoxycarbonyl)pyrrolidin-1-ylcarbonyl, (ethoxycarbonyl)pyrrolidin-1-ylcarbonyl, etc.], or said lower alkylene being optionally interrupted by other hetero atom(s) such as nitrogen, oxygen or sulfur (e.g. morpholinocarbonyl, etc.), lower alkylsufonylcarbamoyl (e.g. methylsufonylcarbamoyl, etc.), arenesulfonylcarbamoyl (e.g. benzenesulfonylcarbamoyl, etc.), and the like.

Preferable example of the amidated carboxy thus defined may be:

carbamoyl, mono(or di)lower alkyl carbamoyl (e.g. methylcarbamoyl, ethylcarbamoyl, isopropylcarbamoyl, butylcarbamoyl, 3-methylbutylcarbamoyl, isobutylcarbamoyl, pentylcarbamoyl, dimethylcarbamoyl, diethylcarbamoyl, etc.), N-(lower)alkyl-N-[carboxy(lower)alkyl]carbamoyl [e.g. N-methyl-N-(carboxymethyl)carbamoyl, etc.]

N-(lower)alkyl-N-[protected carboxy(lower)alkyl]carbamoyl such as N-(lower)alkyl-N-[lower alkoxycarbonyl(lower)alkyl]carbamoyl [e.g. N-methyl-N-(methoxycarbonylmethyl)carbamoyl, etc.], N-[carboxy(lower)alkyl]carbamoyl [e.g. N-(carboxymethyl)carbamoyl, N-(2-carboxyethyl)carbamoyl, N-(3-carboxypropyl)carbamoyl, N-(4-carboxybutyl)carbamoyl, N-(5-carboxypentyl)carbamoyl, N-(1-carboxyethyl)carbamoyl, N-(1-carboxy-2-methylpropyl)carbamoyl, N-(1-carboxy-3-methylbutyl)carbamoyl, N-(1,2-dicarboxyethyl)carbamoyl, etc.], N-[protected carboxy(lower)alkyl]carbamoyl such as N-[lower alkoxycarbonyl(lower)alkyl]carbamoyl [e.g. N-(methoxycarbonylmethyl)carbamoyl, N-(2-methoxycarbonylethyl)carbamoyl, N-(3-methoxycarbonylpropyl)carbamoyl, N-(4-methoxycarbonylbutyl)carbamoyl, N-(5-methoxycarbonylpentyl)carbamoyl, N-[1,2-bis(methoxycarbonyl)ethyl]- carbamoyl, etc.), N-[ar(lower)alkoxycarbonyl(-lower)alkyl]carbamoyl, preferably N-[phenyl(-lower)alkoxycarbonyl(lower)alkyl]carbamoyl [e.g. N-(benzyloxycarbonylmethyl)carbamoyl, N-(2-benzyloxycarbonylethyl)carbamoyl, N-(3-benzyloxycarbonylpropyl)carbamoyl, N-(4-benzyloxycarbonylbutyl)carbamoyl, N-(5-benzyloxycarbonylpentyl)carbamoyl, etc.), N-[{aroyl(lower)alkoxy}(lower)alkyl]carbamoyl, preferably benzoyl(lower)alkoxy(lower)alkyl]carbamoyl [e.g. N-(phenacyloxycarbonylmethyl)carbamoyl, N-(2-phenacyloxycarbonylethyl)carbamoyl, N-(3-phenacyloxycarbonylpropyl)carbamoyl, N-(4-phenacyloxycarbonylbutyl)carbamoyl, N-(5-phenacyloxycarbonylpentyl)carbamoyl, N-(1-phenacyloxyethyl)carbamoyl, N-(1-phenacyloxy-2-methylpropyl)carbamoyl, N-(1-phenacyloxy-3-methylbutyl)carbamoyl, etc.], N-[carboxy(lower)alkyl]carbamoyl subsituted by aryl such as N-[carboxy(lower)alkyl]carbamoyl substituted by phenyl or naphthyl [e.g. N-(1-carboxy-2-phenylethyl)carbamoyl, etc.], N-[protected carboxy(lower)alkyl]carbamoyl subsituted by aryl such as N-[{lower alkoxycarbonyl}(lower)alkyl]carbamoyl substituted by phenyl on naphthyl [e.g. N-(1-ethoxycarbonyl-2-phenylethyl)carbamoyl, etc.], N-[carboxy(lower)alkyl]carbamoyl substituted by heterocyclic group such as pyrrolyl, pyrrolinyl, imidazolyl, pyrazolyl, pyridyl, and its N-oxide, pyrimidyl, pyrazinyl, pyridazinyl, triazolyl, tetrazolyl and dihydrotriazinyl [e.g. N-{1-carboxy-2-(pyridin-2-yl)ethyl}carbamoyl, etc.], N-[protected carboxy(lower)alkyl]carbamoyl subsituted by heterocyclic group such as N-[lower alkoxycarbonyl(lower)alkyl]carbamoyl substituted by pyrrolyl, pyrrolinyl, imidazolyl, pyrazolyl, pyridyl, and its N-oxide, pyrimidyl, pyrazinyl, pyridazinyl, triazolyl, tetrazolyl or dihydrotriazinyl [e.g. N-{1-ethoxycarbonyl-2-(pyridin-2-yl)ethyl}carbamoyl, etc.], N-[aryl(lower)alkyl]carbamoyl such as phenyl(-lower)alkylcarbamoyl (e.g. N-benzylcarbamoyl, etc.), N-[{carboxy(C$_3$-C$_7$)cycloalkyl}(lower)alkyl]carbamoyl [e.g. N-(4-carboxycyclohexylmethyl)carbamoyl, etc.], N-[{protected carboxy(C$_3$-C$_7$)cycloalkyl}(lower)alkyl]carbamoyl such as N-[{lower alkoxycarbonyl(-C$_3$-C$_7$)cycloalkyl}(lower)alkyl]carbamoyl [e.g. N-(4-ethoxycarbonylcyclohexylmethyl)carbamoyl, etc.], N-[heterocyclic-(lower)alkyl]carbamoyl, said heterocyclic group being azetidinyl, pyrrolidinyl, imidazolidinyl, peperidinyl, pyrazolidinyl and peperazinyl, such as N-[pyrrolidinyl(lower)alkyl]-carbamoyl [e.g. N-{2-(pyrrolidin-1-yl)ethyl}carbamoyl, etc.], wherein said heterocyclic group may be substituted by suitable substituent(s) such as oxo, carboxy, protected carboxy as mentioned above and carbamoyl, for example, oxopyrrolidinyl substituted by carboxy, lower alkoxycarbonyl or carbamoyl [e.g. 2-oxo-5-carboxypyrrolidinyl, 2-oxo-5-ethoxycarbonylpyrrolidinyl, 2-oxo-5-carbamoyl-pyrrolidinyl, etc.);

(C$_3$-C$_7$)cycloalkylcarbamoyl (e.g. cyclohexylcarbamoyl, etc.), carbamoyl substituted by amino or di(lower)alkylamino [e.g. N-aminocarbamoyl, N-(dimethylamino)carbamoyl, etc.], N-(optionally substituted heterocyclic)carbamoyl wherein the heterocyclic moiety being thiazolyl, 1,2-thiazolyl, thiazolinyl, thiadiazolyl, thiazolidinyl, benzothiazolyl, benzothiadiazolyl, morpholinyl, [e.g. thiazolylcarbamoyl, benzothiazolylcarbamoyland morpholinylcarbamoyl, etc.], each of said heterocyclic group may be substituted by lower alkyl, for example, N-(lower alkylthiadiazolyl)carbamoyl (e.g. methylthiadiazolylcarbanoyl, etc.), lower alkyleneaminocarbonyl (e.g. pyrrolidin-1-ylcarbonyl, hexahydro-1H-azepin-1-ylcarbonyl, etc.), lower alkyleneaminocarbonyl substituted by carboxy or protected carboxy such as lower alkoxycarbonyl [e.g. 2-carboxypyrrolidin-1-ylcarbonyl, 2-(methoxycarbonyl)pyrrolidin-1-ylcarbonyl, 2-(ethoxycarbonyl)pyrrolidin-1-ylcarbonyl, etc.], lower alkyleneaminocarbonyl wherein said lower alkylene being interrupted by oxygen (e.g. morpholinocarbonyl, etc.), lower alkylsufonylcarbamoyl (e.g. methylsufonylcarbamoyl, etc.), C$_6$-C$_{10}$arenesulfonylcarbamoyl (e.g. benzenesulfonylcarbamoyl, etc.), and the like.

Suitable "optionally substituted heterocyclic(lower-)alkyl" means aforementioned lower alkyl, which is substituted by saturated or unsaturated, monocyclic or polycyclic heterocyclic group containing at least one hetero-atom such as an oxygen, sulfur, nitrogen atom and the like.

More preferable heterocyclic moiety may be heterocyclic group such as:

unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

saturated 3 to 8-membered, preferably 5 or 6-membered heteromonocyclic group containing 1 to 4 nitrogen atom(s), for example, azetidinyl, pyrrolidinyl, imidazolidinyl, piperidinyl, pyrazolidinyl, piperazinyl, etc;

unsaturated condensed 7 to 12-membered heterocyclic group containing 1 to 5 nitrogen atom(s), for example, indolyl, isoindolyl, indolizinyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.;

unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.;

saturated 3 to 8-membered, preferably 5 or 6-membered heteromonocyclic group containing 1 to 2 oxygen atom(s) and 1 to 3 nitrogen atom(s), for example, morpholinyl, etc.;

unsaturated condensed 7 to 12-membered heterocyclic group containing 1 to 2 oxygen atom(s) and 1 to 3 nitrogen atom(s), for example, benzoxazolyl, benzoxadiazolyl, etc.;

unsaturated 3 to 8-membered, preferably 5 or 6-membered heteromonocyclic group containing 1 to 2 sulfur atom(s) and 1 to 3 nitrogen atom(s), for example, thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.;

saturated 3 to 8-membered, preferably 5 or 6-membered heteromonocyclic group containing 1 to 2 sulfur atom(s) and 1 to 3 nitrogen atom(s), for example, thiazolidinyl, etc.;

unsaturated 3 to 8-membered, preferably 5 or 6-membered heteromonocyclic group containing a sulfur atom, for example, thienyl, etc.

unsaturated condensed 7 to 12-membered heterocyclic group containing 1 to 2 sulfur atom(s) and 1 to 3 nitrogen atom(s), for example, benzothiazolyl, benzothiadiazolyl, etc. and the like;

wherein said heterocyclic group may be substituted by one or more, preferably one or two suitable substituent(s) such as:

hydroxy;

protected hydroxy, in which the hydroxy group is protected by a conventional hydroxy-protective group such as acyl as mentioned above, tri(lower)alkylsilyl (e.g. t-butyldimethylsilyl, etc.), etc.;

halogen (e.g. chlorine, bromine, iodine or fluorine);

lower alkoxy, which may be straight or branched one alkoxy such as methoxy, ethoxy, propoxy, isopropoxy, butoxy, pentyloxy, hexyloxy, etc., more preferably $C_1$–$C_4$ alkoxy (e.g. methoxy, etc.);

lower alkyl as mentioned above, more preferably $C_1$–$C_4$ alkyl (e.g. methyl, etc.); amino; nitro; cyano; and the like.

And further when said heterocyclic group has imino-moiety(ies) in its ring, the imino-moiety(ies) may be substituted by suitable substituent(s) such as;

lower alkyl as mentioned above (e.g. methyl, ethyl, propyl, isobutyl, etc.);

imino-protective group as mentioned below, more preferably lower alkanoyl (e.g. formyl, etc.), arenesulfonyl (e.g. tosyl, etc.); and the like.

Preferable example of "optionally substituted heterocyclic(lower)alkyl" thus defined may be:

lower alkyl substituted by unsaturated 5 or 6-membered heteromonocyclic group containing 1 to 4 nitrogen atom(s), such as pyridyl(lower)alkyl, imidazolyl(lower)alkyl, etc.;

lower alkyl substituted by unsaturated condensed 7 to 12-membered heterocyclic group containing 1 to 5 nitrogen atom(s), such as indolyl(lower)alkyl, etc.;

lower alkyl substituted by unsaturated 5 or 6-membered heteromonocyclic group containing 1 to 2 sulfur atom(s) and 1 to 3 nitrogen atom(s) such as thiazolyl(lower)alkyl, etc.; and the like, wherein said heterocyclic group may be substituted by suitable substituent(s) such as lower alkyl (e.g. methyl, ethyl propyl, isobutyl, etc.), lower alkanoyl (e.g. formyl, etc.), ($C_6$–$C_{10}$)arenesulfonyl (e.g. tosyl, etc.), and the like.

More preferable example may be:

pyridyl(lower)alkyl [e.g. 2-(or 3- or 4-)pyridylmethyl, etc.], imidazolyl(lower)alkyl [e.g. imidazol-1(or 3)-yl methyl, etc.], indolyl(lower)alkyl [e.g. indol-3-ylmethyl, etc.], thiazolyl(lower)alkyl [e.g. thiazol-3-ylmethyl, etc.], N-arenesulfonylimidazolyl(lower)alkyl (e.g. 1-tosylimidazol-3-ylmethyl, etc.), N-(lower)alkanoylindolyl(lower)alkyl (e.g. N-formylindol-3-ylmethyl, etc.), and N-(lower)alkylindoyl(lower)alkyl [e.g. N-methyl(or ethyl or propyl or isobutyl)indol-3-ylmethyl, etc.] for $R^3$; and pyridyl(lower)alkyl (e.g. 2-pyridylmethyl, etc.), imidazolyl(lower)alkyl [e.g. imidazol-1(or 3)-ylmethyl, etc.], and N-arenesulfonylimidazolyl(lower)alkyl (e.g. 1-tosylimidazol-3-ylmethyl, etc.) for $R^2$, and the most preferred one may be:

indolyl(lower)alkyl, N-(lower)alkanoylindolyl(lower)alkyl and N-(lower)alkylindolyl(lower)alkyl for $R^3$, and pyridyl(lower)alkyl and imidazolyl(lower)alkyl for $R^2$.

Suitable "ar(lower)alkyl" may include $C_6$–$C_{10}$ ar(lower)alkyl such as phenyl(lower)alkyl (e.g. benzyl, phenethyl, etc.), tolyl(lower)alkyl, xylyl(lower)alkyl, naphthyl(lower)alkyl (e.g. naphthylmethyl, etc.), and the like, wherein said ar(lower)alkyl may be substituted by suitable substituent(s) such as those mentioned in the explanation of "optionally substituted heterocyclic(lower)alkyl" as mentioned above.

Preferable example of optionally substituted ar(lower)alkyl may be phenyl(lower)alkyl and naphthyl(lower)alkyl, and the most preferable one may be benzyl and naphthylmethyl for $R^2$, and benzyl for $R^3$.

Suitable "lower alkylimino" means imino group substituted by aforementioned lower alkyl, in which the most preferable example may be methylimino.

Suitable "cyclo(lower)alkyl(lower)alkyl" means aforementioned lower alkyl which is substituted by $C_3$–$C_7$ cyclo(lower)alkyl such as cyclopropyl, cyclobutyl, cyclopentyl, cyclohexyl, cycloheptyl, and the like, wherein more preferable example may be $C_4$–$C_6$ cyclo(lower)alkyl(lower)alkyl, and the most preferable one may be cyclohexylmethyl.

Suitable "optionally substituted lower alkyl" may include aforementioned lower alkyl (e.g. methyl, ethyl, isopropyl, butyl, isobutyl, etc.) which is optionally substituted by suitable substituent(s) such as optionally substituted heterocyclic group as mentioned above (e.g. pyridyl, thiazolyl, imidazolyl, N-tosylimidazolyl, etc.); $C_6$–$C_{10}$ aryl as mentioned below (e.g. phenyl, naphthyl, etc.); amino; protected amino as mentioned below (e.g. benzyloxycarbonylamino, etc.); carboxy; protected carboxy as mentioned above (e.g. benzyloxycarbonyl, etc.); and the like.

Preferable example of "optionally substituted lower alkyl" thus defined may be:

lower alkyl (e.g. isopropyl, isobutyl, etc.), pyridyl(lower)alkyl [e.g. 2-(or 3- or 4-)pyridylmethyl, 2-(2-pyridyl)ethyl, etc.], thiazolyl(lower)alkyl [e.g. 3-thiazolylmethyl, etc.], imidazolyl(lower)alkyl [e.g. 2-(or 3-)imidazolylmethyl, etc.], N-protected imidazolyl(lower)alkyl such as N-(arenesulfonyl)imidazolyl(lower)alkyl [e.g. N-tosyl-2-(or 3-)imidazolylmethyl, etc.], $C_6$–$C_{10}$ ar(lower)alkyl such as phenyl(lower)alkyl (e.g. benzyl, naphthylmethyl, etc.), amino(lower)alkyl (e.g. 4-aminobutyl, etc.),
protected amino(lower)alkyl such as $C_6$-$C_{10}$ ar(lower)alkoxycarbonyl [e.g. 4-(benzyloxycarbonylamino)butyl, etc.],
carboxy(lower)alkyl (e.g. carboxymethyl, 2-carboxyethyl, etc.),
protected carboxy(lower)alkyl such as $C_6$-$C_{10}$ ar(lower)alkoxycarbonyl(lower)alkyl (e.g. benzyloxycarbonylmethyl, 2-benzyloxycarbonylethyl, etc.), and the like.

The most preferable example of "optionally substituted lower alkyl" thus defined may be:

isopropyl, isobutyl, 2-(or 3- or 4-)pyridylmethyl, 2-(2-pyridyl)ethyl, 3-thiazolylmethyl, 2-(or 3-)imidazolylmethyl, N-tosyl-2-(or 3-)imidazolylmethyl, benzyl, naphthylmethyl, 4-aminobutyl, 4-(benzyloxycarbonylamino)butyl, carboxymethyl, 2-carboxyethyl, benzyloxycarbonylmethyl and 2-benzyloxycarbonylethyl for $R^4$; and 2-pyridylmethyl and 2-(2-pyridyl)ethyl for $R^6$.

Suitable "optionally substituted heterocyclic group" may include the same heterocyclic moiety as mentioned before such as pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.], dihydrotriazinyl (e.g. 4,5-dihydro-1,2,4-triazinyl, 2,5-dihydro-1,2,4-triazinyl, etc.), thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), and the like, wherein said heterocyclic group is optionally substituted by the same substituent(s) mentioned therein such as iminoprotective group (e.g. arenesulfonyl, etc.).

Suitable "aryl" may include $C_6$-$C_{10}$ aryl such as phenyl, tolyl, xylyl, cumenyl, naphthyl, and the like, in which more preferable example may be phenyl and naphthyl.

Suitable amino- or imino-protective group for protected amino or protected imino may include acyl as mentioned above, in which more preferable example may be lower alkanoyl, ($C_6$-$C_{10}$)ar(lower)alkoxycarbonyl and ($C_6$-$C_{10}$) arenesulfonyl, and the most preferable one may be benzyloxycarbonyl.

Suitable "imino containing heterocyclic(lower)alkyl optionally substituted by suitable substituent(s)" means those given for "optionally substituted heterocyclic(lower)alkyl" mentioned above, in which the heterocyclic ring contains an imino group (—NH—), such as indolyl(lower)alkyl, imidazolyl(lower)alkyl, and the like.

Suitable "protected imino containing heterocyclic(lower)alkyl optionally substituted by suitable substituent(s)" means aforementioned "imino containing. heterocyclic(lower)alkyl optionally substituted by suitable substituent(s)", in which the imino group is protected by a conventional imino-protective group as mentioned below.

"Acyl substituted by a protected amino group" means the acyl as explained above which is substituted by the protected amino as mentioned above.

"Acyl substituted by an amino group" means the acyl as explained above which is substituted by amino group.

Suitable "imino-protective group" may include conventional ones used in the peptide chemistry such as those given for the amino-protective group in the protected amino.

The preferred embodiments of each definition may be as follows.

$R^1$ is acyl such as carbamoyl, or an organic carboxylic, an organic carbonic, an organic sulfonic or an organic carbamic acyl, for instance: lower alkanoyl (e.g. acetyl, propionyl, 3,3-dimethylbutyryl, pivaloyl, 4-methylpentanoyl, etc.); amino(lower)alkanoyl (e.g. 2-amino-3-methylpentanoyl, etc.); protected amino(lower)alkanoyl, for example, acylamino(lower)alkanoyl such as lower alkoxycarbonylamino(lower)alkanoyl (e.g. 2-tert-butoxycarbonylamino-3-methylpentanoyl, etc.), $C_3$-$C_7$.cycloalkylureido(lower)alkanoyl (e.g. 2-(3-cyclohexylureido)-3-methylpentanoyl, etc.); lower alkoxycarbonyl (e.g. tert-butoxycarbonyl, etc.); $C_3$-$C_7$cycloalkyl(lower)alkanoyl (e.g. cyclohexylacetyl, etc.); $C_3$-$C_7$cycloalkylcarbonyl, (e.g. cyclohexylcarbonyl, etc.); $C_3$-$C_7$cycloalkyloxycarbonyl (e.g. cyclohexyloxycarbonyl, etc.); aroyl such as $C_6$-$C_{10}$aroyl (e.g. benzoyl, 1- or 2-naphthoyl, etc.); ar(lower)alkanoyl such as $C_6$-$C_{10}$ar(lower)alkanoyl (e.g. phenylacetyl, 1- or 2-naphthylacetyl, 3-phenylpropionyl, etc.); amino-substituted ar(lower)alkanoyl, for example, amino-substituted ($C_6$-$C_{10}$)ar(lower)alkanoyl such as amino-substituted phenyl(lower)alkanoyl (e.g. 2-amino-2-phenylacetyl, etc.); protected amino-substituted ar(lower)alkanoyl, for example, acylamino-substituted ($C_6$-$C_{10}$)ar(lower)alkanoyl such as lower alkoxycarbonylamino-substituted phenyl(lower)alkanoyl (e.g. 2-(4-tert-butoxycarbonylaminophenyl)acetyl, 2-tert-butoxycarbonylamino-2-phenylacetyl, etc.); haloar(lower)alkanoyl, for example, halo($C_6$-$C_{10}$)ar(lower)alkanoyl such as halophenyl(lower)alkanoyl (e.g. (2-chlorophenyl)acetyl, etc.); ar(lower)alkenoyl, for example, $C_6$-$C_{10}$ar(lower)alkenoyl such as phenyl(lower)alkenoyl (e.g. cinnamoyl, etc.); arylglyoxyloyl such as $C_6$-$C_{10}$arylglyoxyloyl (e.g. phenylglyoxyloyl, etc.); ar(lower)alkylglyoxyloyl such as $C_6$-$C_{10}$ar(lower)alkylglyoxyloyl (e.g. benzylglyoxyloyl, etc.); pyridylcarbonyl (e.g. 2- or 3- or 4-pyridylcarbonyl, etc.); tetrahydropyridylcarbonyl (e.g. 1,2,3,6-tetrahydropyridin-1-ylcarbonyl, etc.); tetrahydroquinolylcarbonyl (e.g. 1,2,3,4-tetrahydroquinolin-1-ylcarbonyl, etc.); tetrahydroisoquinolylcarbonyl (e.g. 1,2,3,4-tetrahydroisoquinolin-2-ylcarbonyl, etc.); morpholinylcarbonyl (e.g. morpholinocarbonyl, etc.); thiomorpholinylcarbonyl (e.g. thiomorpholinocarbonyl, etc.); indolylcarbonyl (e.g. 2-indolylcarbonyl, etc.); piperazinylcarbonyl substituted by one to three substituents selected from oxo and lower alkyl (e.g. 4-methyl-2-(1-methylpropyl)-3-oxopiperazin-1-ylcarbonyl, etc.); pyridyl(lower)alkanoyl (e.g. 2- or 3- or 4-pyridylacetyl, etc.); morpholinylcarbonyl(lower)alkanoyl (e.g. 3-(morpholinocarbonyl)propionyl, etc.); ar(lower)alkylsulfonyl, for example, $C_6$-$C_{10}$ar(lower)alkylsulfonyl such as phenyl(lower)alkylsulfonyl (e.g. benzylsulfonyl, etc.); N- or N,N-di(lower or higher)alkylcarbamoyl such as N- or N,N-di($C_1$-$C_{10}$)alkylcarbamoyl (e.g. isopropylcarbamoyl, 2-methylbutylcarbamoyl, heptylcarbamoyl, dimethylcarbamoyl, diethylcarbamoyl, dipropylcarbamoyl, diisopropylcarbamoyl, dibutylcarbamoyl, diisobutylcarbamoyl, etc.); hydroxy(lower)alkylcarbamoyl (e.g. 1-hydroxymethyl-3-methylbutylcarbamoyl, etc.); carboxy(lower)alkylcarbamoyl (e.g. 1-carboxy-2-methylbutylcarbamoyl, etc.); protected carboxy(lower)alkylcarbamoyl, for example, esterified carboxy(lower)alkylcarbamoyl such as lower alkoxycarbonyl(lower)alkylcarbamoyl (e.g. 1-methoxycarbonyl-2-methylbutylcarbamoyl, etc.); carbamoyl(lower)alkylcarbamoyl (e.g. 1-carbamoyl-2-methylbutylcarbamoyl, etc.); [N- or N,N-di(lower)alkylcarbamoyl](lower)alkylcarbamoyl (e.g. 1-isopropylcarbamoyl-2-methylbutylcarbamoyl, dimethylcarbamoylmethylcarbamoyl, 1-(dimethylcarbamoyl)ethylcarbamoyl, 2-(dimethylcarbamoyl)ethylcarbamoyl, 1-(dimethylcarbamoyl)-2-methylpropylcarbamoyl, 1-(dimethylcarbamoyl)-2,2-dimethylpropylcarbamoyl, 1-(dimethylcarbamoyl)-2-methylbutylcarbamoyl, 1-(dimethylcarbamoyl)-3-methylbutylcarbamoyl, 1-(diethylcarbamoyl)-2-methylbutylcarbamoyl, 1-(dimethylcarbamoyl)-pentylcarbamoyl, etc.); N-lower alkyl-N-[hydroxy(lower)alkyl]carbamoyl (e.g. N-(2-hydroxyethyl)-N-methylcarbamoyl, etc.); N-lower alkyl-N-[di(lower)alkylcarbamoyl(lower)alkyl]carbamoyl (e.g. N-(1-dimethylcarbamoyl-2-methylbutyl)-N-methylcarbamoyl, N-(1-dimethylcarbamoyl-3-methylbutyl)-N-methylcarbamoyl, etc.); lower or higher alkyleneaminocarbonyl such as $C_3-C_{10}$alkyleneaminocarbonyl (e.g. pyrrolidin-1-ylcarbonyl, piperidin-1-ylcarbonyl, 3,5- or 2,6-dimethylpiperidin-1-ylcarbonyl, hexahydro-1H-azepin-1-ylcarbonyl, octahydroazocin-1-ylcarbonyl, etc.); di(lower)alkylcarbamoyl(lower)alkyleneaminocarbonyl (e.g. 2-(dimethylcarbamoyl)pyrrolidin-1-ylcarbonyl, 4-(dimethylcarbamoyl)piperidin-1-ylcarbonyl, etc.); N-lower alkyl-N-($C_3-C_7$)cycloalkylcarbamoyl (e.g. N-cyclohexyl-N-methylcarbamoyl, etc.); mono- or di($C_3-C_7$)cycloalkylcarbamoyl (e.g. cyclohexylcarbamoyl, dicyclohexylcarbamoyl, etc.); hydroxy- or di(lower)alkylcarbamoyl- or di(lower)alkylcarbamoyl(lower)alkyl-substituted ($C_3-C_7$)cycloalkylcarbamoyl (e.g. 4-hydroxycyclohexylcarbamoyl, 1- or 4-(dimethylcarbamoyl)cyclohexylcarbamoyl, 1- or 4-(dimethylcarbamoylmethyl)cyclohexylcarbamoyl, etc.); $C_3-C_7$cycloalkyl(-lower)alkylcarbamoyl (e.g. cyclohexylmethylcarbamoyl, etc.); di(lower)alkylcarbamoyl-substituted $C_3-C_7$cycloalkyl(lower)alkylcarbamoyl (e.g. [1-cyclohexyl-1-(dimethylcarbamoyl)methyl]carbamoyl, etc.); di(lower)alkylcarbamoyl-substituted ar(-lower)alkylcarbamoyl such as di(lower)alkylcarbamoyl-substituted phenyl(lower)alkylcarbamoyl (e.g. [1-phenyl-1-(dimethylcarbamoyl)methyl]carbamoyl, etc.); arylcarbamoyl, preferably $C_6-C_{10}$arylcarbamoyl, in which the aryl group may be substituted by one to three substituents selected from halogen, lower alkyl and lower alkoxy (e.g. phenylcarbamoyl, 2- or 3- or 4-chlorophenylcarbamoyl, 4-tolylcarbamoyl, 4-methoxyphenylcarbamoyl, etc.); pyridylcarbamoyl (e.g. 2-pyridylcarbamoyl, 3-pyridylcarbamoyl, etc.); N-protected piperidylcarbonyl, for example, N-acylpireridylcarbonyl such as N-lower alkoxycarbonylpiperidylcarbonyl (e.g. 1-ethoxycarbonylpiperidin-4-ylcarbonyl, etc.); morpholinyl(lower)alkylcarbamoyl (e.g. 2-(morpholino)ethylcarbamoyl, etc.); lower alkanoylcarbazoyl (e.g. 3-isobutyrylcarbazoyl, etc.); lower alkyleneamminocarbamoyl (e.g. piperidin-1-ylcarbamoyl, etc.); N-($C_3-C_7$)cycloalkylcarbamoyl(lower)alkylcarbamoyl (e.g. 1-cyclohexylcarbammoyl-2-methylbutylcarbamoyl, etc.); lower alkyleneaminocarbonyl(lower)alkylcarbamoyl (e.g. 1-(piperidin-1-ylcarbonyl)-2-methylbutylcarbamoyl, etc.); pyridyl(lower)alkylcarbamoyl (e.g. 2-pyridylmethylcarbamoyl, etc.); or oxo-substituted hexahydroazepinylcarbamoyl (e.g. 2-oxo-hexahydro-1H-azepin-3-ylcarbamoyl, etc.); particularly, N,N-di(lower)alkylcarbamoyl; mono- or di($C_3-C_7$)cycloalkylcarbamoyl; N-lower alkyl-N-($C_3-C_7$)cycloalkylcarbamoyl; N-lower alkyl-N-[di(lower)alkylcarbamoyl(lower)alkyl]-carbamoyl; $C_6-C_{10}$arylcarbamoyl; lower or higher alkyleneaminocarbonyl such as $C_3-C_{10}$alkyleneaminocarbonyl; or N-lower alkyl-N-[hydroxy(lower)alkyl]carbamoyl;

$R^2$ is lower alkyl (e.g. butyl, isobutyl, 1-methylpropyl, 2,2-dimethylpropyl, etc.); particularly, isobutyl;

$R^3$ is indolyl(lower)alkyl (e.g. 3-indolylmethyl, etc.); N-(lower)alkylindolyl(lower)alkyl (e.g. 1-methyl-3-indolylmethyl, 1-ethyl-3-indolylmethyl, 1-propyl-3-indolylmethyl, 1-isobutyl-3-indolylmethyl, etc.); N-acylindolyl(lower)alkyl such as N-(lower)alkanoylindolyl(lower)alkyl (e.g. 1-formyl-3-indolylmethyl, etc.); or ar(lower)alkyl such as $C_6-C_{10}$ar(lower)alkyl (e.g. benzyl, 1- or 2-naphthylmethyl, etc.); particularly, N-(lower)alkylindolyl(lower)alkyl such as 1-methyl-3-indolylmethyl;

$R^4$ is hydrogen, lower alkyl (e.g. isopropyl, isobutyl, etc.); amino(lower)alkyl (e.g. 4-aminobutyl, etc.); protected amino(lower)alkyl, for example, acylamino(lower)alkyl such as mono- or di or triphenyl(lower)alkoxycarbonylamino(lower)alkyl (e.g. 4-benzyloxycarbonylaminobutyl, etc.); carboxy(lower)alkyl (e.g. carboxymethyl, 2-carboxyethyl, etc.); protected carboxy(lower)alkyl, for example, esterified carboxy(lower)alkyl such as mono- or di or triphenyl(lower)alkoxycarbonyl(lower)alkyl (e.g. benzyloxycarbonylmethyl, 2-benzyloxycarbonylethyl, etc.); ar(lower)alkyl such as $C_6-C_{10}$ar(lower)alkyl (e.g. benzyl, 1- or 2-naphthylmethyl, etc,); pyridyl(lower)alkyl (e.g. 2- or 3- or 4-pyridylmethyl, etc.); imidazolyl(lower)alkyl (e.g. 1H-4-imidazolylmethyl, etc.); or thiazolyl(-lower)alkyl (e.g. 4-thiazolylmethyl, etc.); particularly, $C_6-C_{10}$ar(lower)alkyl such as benzyl; or pyridyl(lower)alkyl such as 2-pyridylmethyl;

$R^5$ is carboxy; esterified carboxy such as: lower alkoxycarbonyl (e.g. methoxycarbonyl, ethoxycarbonyl, etc.), ar(lower)alkoxycarbonyl such as mono or di or triphenyl(lower)alkoxycarbonyl (e.g. benzyloxycarbonyl, etc.), aroyl(lower)alkoxycarbonyl such as benzoyl(lower)alkoxycarbonyl (e.g. phenacyl, etc.); amidated carboxy such as: carbamoyl, N- or N,N-di(lower)alkylcarbamoyl (e.g. methylcarbamoyl, ethylcarbamoyl, propylcarbamoyl, isopropylcarbamoyl, butylcarbamoyl, N,N-dimethylcarbamoyl, N,N-diethylcarbamoyl etc.), lower alkylcarbamoyl substituted by one or two substituents selected from carboxy and protected carboxy (preferably, esterified carboxy, more preferably, lower alkoxycarbonyl, mono or di or triphenyl(lower)alkoxycarbonyl or benzoyl(lower)alkoxycarbonyl) (e.g. carboxymethylcarbamoyl, 1- or 2-carboxyethylcarbamoyl, 4-carboxybutylcarbamol, 5-carboxypentylcarbamoyl, 1-carboxy-2-methylpropylcarbamoyl, 1-carboxy-3-methylbutylcarbamoyl, 1,2-dicarboxyethylcarbamoyl, benzyloxycarbonylmethylcarbamoyl, 2-benzyloxycarbonylethylcarbamoyl, 1- or 2-phenacyloxycarbonylethylcarbamoyl, 4-phenacyloxycarbonylbutylcarbamoyl, 5-phenacyloxycarbonylpentylcarbamoyl, 1-methoxycarbonyl-2-methylpropylcarbamoyl, 1-methoxycarbonyl-3-methylbutylcarbamoyl, 1,2-bis(methoxycarbonyl)ethylcarbamoyl, etc.), N-(lower)alkyl-N-[carboxy- or protected carboxy (preferably, esterified carboxy, more preferably lower alkoxycarbonyl)(lower)alkyl]carbamoyl (e.g. N-methyl-N-(carboxymethyl)carbamoyl, N-methyl-N-(methoxycarbonylmethyl)carbamoyl, etc.), ar(lower)alkylcarbamoyl, for example, $C_6-C_{10}$ar(lower)alkylcarbamoyl such as phenyl(lower)alkylcarbamoyl (e.g. benzylcarbamoyl, etc.), carboxy- or protected carboxy (preferably, esterified carboxy)-substituted ar(lower)alkylcarbamoyl such as carboxy- or lower alkoxycarbonyl-substituted phenyl(lower)alkylcarbamoyl (e.g. 1-carboxy-2-phenylethylcarbamoyl, 1-ethoxycarbonyl-2-phenylethylcarbamoyl, etc.), $C_3-C_7$cycloalkylcarbamoyl (e.g. cyclohexylcarbamoyl, etc.), N-[carboxy- or protected carboxy-substituted $C_3-C_7$-cycloalkyl(lower)alkyl]carbamoyl, for example, [carboxy($C_3-C_7$)cycloalkyl(lower)alkyl]carbamoyl (e.g. 4-carboxycyclohexylmethylcarbamoyl, etc.), [esterified carboxy-substituted $C_3-C_7$cycloalkyl(lower)alkyl]carbamoyl such as lower alkoxycarbonyl($C_3-C_7$)cycloalkyl(lower)alkyl]carbamoyl (e.g. 4-(ethoxycarbonyl)cyclohexylmethylcarbamoyl, etc.), acylcarbamoyl such as lower alkylsulfonylcarbamoyl (e.g. methylsulfonylcarbamoyl, etc.), arylsulfonylcarbamoyl, for example, $C_6-C_{10}$arylsulfonylcarbamoyl (e.g. phenylsulfonylcarbamoyl, etc.), carboxy- or protected carboxy (preferably, esterified carboxy)-substituted pyridyl(lower)alkylcarbamoyl such as carboxy- or lower alkoxycarbonyl-substituted pyridyl(lower)alkylcarbamoyl (e.g. 1-carboxy-2-(2-pyridyl)ethylcarbamoyl, 1-ethoxycarbonyl-2-(2-pyridyl)ethylcarbamoyl, etc.) lower alkyleneaminocarbonyl (e.g. pyrrolidin-1-ylcarbonyl, piperidin-1-ylcarbonyl, etc.), lower alkyleneaminocarbonyl substituted by carboxy or protected carboxy (preferably, esterified carboxy, more preferably, lower alkoxycarbonyl) (e.g. 2-carboxypyrrolidin-1-ylcarbonyl, 2-methoxycarbonylpyrrolidin-1-ylcarbonyl, etc.), [lower alkyleneamino(lower)alkyl]carbamoyl substituted by one to two substituents selected from carboxy, protected carboxy (preferably, esterified carboxy, more preferably, lower alkoxycarbonyl) and carbamoyl (e.g. 2-(2-carboxy-5-oxopyrrolidin-1-yl)ethylcarbamoyl, 2-(2-ethoxycarbonyl-5-oxopyrrolidin-1-yl)ethylcarbamoyl, 2-(2-carbamoyl-5-oxopyrrolidin-1-yl)ethylcarbamoyl, etc.), morpholinocarbonyl, morpholinylcarbamoyl (e.g. morpholinocarbamoyl, etc.), pyridylcarbamoyl (e.g. 2-pyridylcarbamoyl, etc.), thiazolylcarbamoyl (e.g. 2-thiazolylcarbamoyl, etc.), lower alkylthiadiazolylcarbamoyl such as 5-(lower)alkyl-1,3,4-thiadiazolylcarbamoyl (e.g. 5-methyl-1,3,4-thiadiazolylcarbamoyl, etc.), benzothiazolylcarbamoyl (e.g. 2-benzothiazolylcarbamoyl, etc.), morpholinyl(lower)alkylcarbamoyl (e.g. 2-morpholinoethylcarbamoyl, etc.), pyridyl(lower)alkylcarbonyl (e.g. 2-pyridylmethylcarbonyl, etc.), carbazoyl, di(lower)alkylcarbazoyl (e.g. 3,3-dimethylcarbazoyl, etc.); carboxy(lower)alkyl (e.g. carboxymethyl, 2-carboxyethyl, 3-carboxypropyl, 4-carboxybutyl, etc.); or protected carboxy(lower)alkyl, for example, esterified carboxy(lower)alkyl such as lower alkoxycarbonyl(lower)alkyl (e.g. methoxycarbonylmethyl, 2-methoxycarbonylethyl, 3-methoxycarbonylpropyl, 4-methoxycarbonylbutyl, etc.), aroyl(lower)alkoxycarbonyl(lower)alkyl (e.g. phenacyloxycarbonylmethyl, 2-phenacyloxycarbonylethyl, 3-phenacyloxycarbonylpropyl, 4-phenacyloxycarbonylbutyl, etc.); particularly, carboxy; lower alkoxycarbonyl; or carbamoyl; N- or N,N-di(lower)alkylcarbamoyl;

$R^6$ is hydrogen; or pyridyl(lower)alkyl (e.g. 2-pyridylmethyl, 2-(2-pyridyl)ethyl, etc.); particularly, hydrogen;

$R^7$ is hydrogen; or lower alkyl (e.g. methyl, etc.); particularly, hydrogen; and A is lower alkylene (e.g. methylene, etc.); —O—; —NH—; or lower alkylimino (e.g. methylimino, etc.); particularly, methylene or —NH—.

The processes for preparing the object compound (I) are explained in detail in the following.

Process 1

The object compound (I) or a salt thereof can be prepared by reacting the compound (II) or its reactive derivative at the carboxy group, or a salt thereof with the compound (III) or its reactive derivative at the amino group, or a salt thereof.

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by reaction of the compound (III) with phosphorus trichloride or phosgene, and the like.

Suitable salts of the compound (III) and its reactive derivative can be referred to the acid addition salts as exemplified for the compound (I).

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminiomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

Suitable salts of the compound (II) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt N,N'-dibenzylethylenediamine salt, etc.], or the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The object compound (I-b) or a salt thereof can be prepared by reacting the compound (I-a) or its reactive derivative at the amino group, or a salt thereof with the compound (IV) or its reactive derivative at the carboxy group, or a salt thereof.

Suitable salts of the compound (I-a) and its reactive derivative can be referred to the ones as exemplified for the compound (III).

Suitable salts of the compound (IV) and its reactive derivative can be referred to the ones as exemplified for the compound (II).

Suitable salts of the compound (I-b) can be referred to the ones as exemplified for the compound (I).

In case that the acyl of the symbol "$R^1$" is one derived from carbamic acids, the starting compound (IV) is usually used in a form of isocyanates.

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

Process 3

The object compound (I) or a salt thereof can be prepared by reacting the compound (V) or its reactive derivative at the carboxy group, or a salt thereof with the compound (VI) or its reactive derivative at the amino group, or a salt thereof.

Suitable salts of the compound (V) and its reactive derivative can be referred to the ones as exemplified for the compound (II).

Suitable salts of the compound (VI) and its reactive derivatives can be referred to the ones as exemplified for the compounds (I) and (III), respectively.

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

Process 4

The object compound (I-d) or a salt thereof can be prepared by subjecting a compound (I-c) or a salt thereof to removal reaction of the carboxy-protective group in $R_a^5$.

Suitable salts of the compounds (I-c) and (I-d) can be referred to the ones as exemplified for the compound (I).

This reaction is carried out in accordance with a conventional method such as solvolysis including hydrolysis, reduction or the like.

The solvolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.].

The removal reaction using Lewis acid such as trihaloacetic acid [e.g. trichloroacetic acid, trifluoroacetic acid, etc.] or the like, is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, carbon tetrachloride, tetrahydrofuran, N,N-dimethylformamide, a mixture thereof or any other solvent which does not adversely influence the reaction. A liquid base or acid can be also used as the solvent. The reaction temperature is not critical and the reaction is usually carried out under cooling to heating.

The reduction method applicable for the removal reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acid to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.

Process 5

The object compound (I-f) or a salt thereof can be prepared by subjecting the compound (I-e) or a salt thereof to removal reaction of the imino- or amino-protective group(s) in $R_a{}^2$.

Suitable salts of the compounds (I-e) and (I-f) can be referred to the ones as exemplified for the compound (I).

This removal reaction can be carried out by a conventional method in the peptide chemistry such as solvolysis, reduction, and the like, the details of which can be referred to those of Process 4.

Process 6

The object compound (I-h) or a salt thereof can be prepared by subjecting the compound (I-g) or a salt thereof to removal reaction of the amino-protective group in $R_a{}^1$.

Suitable salts of the compounds (I-g) and (I-h) can be referred to the ones as exemplified for the compound (I).

This removal reaction can be carried out by a conventional method in the peptide chemistry such as solvolysis, reduction, and, the like, the details of which can be referred to those of Process 4.

Process 7

The object compound (I-j) or a salt thereof can be prepared by reacting the compound (I-i) or its reactive derivative at the carboxy group, or a salt thereof with an optionally substituted amine, or a salt thereof.

Suitable salts of the compound (I-i) and its reactive derivative can be referred to the ones as exemplified for the compound (II).

Suitable salts of the compound (I-j) can be referred to the ones as exemplified for the compound (I).

Suitable optionally substituted amines means the ones which can form aforementioned amidated carboxy of $R_d{}^5$ in the resulting compound (I-j).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

Process 8

The compound (I-g) or a salt thereof can be prepared by acylating the amino group in $R_b{}^1$ of the compound (I-h) or a salt thereof.

Suitable salts of the compounds (I-g) and (I-h) may be the same as those for the compound (I).

Suitable acylating agent used in this reaction may be a conventional acylating agent which is capable of introducing the acyl group as mentioned before such as carboxylic acid, carbonic acid, sulfonic acid and their reactive derivative, for example, an acid halide, an acid anhydride, an activated amide, an activated ester, and the like. Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl ester, trichlorophenyl ester, pentachlorophenylester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

This reaction can be carried out in the presence of an organic or inorganic base such as alkali metal (e.g. lithium, sodium potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

In case that the acylating agent is used in a free form or its salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dichloromethane, alcohol (e.g. methanol, ethanol, etc.), tetrahydrofuran, pyridine, N,N-dimethylformamide, etc., or a mixture thereof.

The reaction temperature is not critical and the reaction is usually carried out under from cooling to heating.

Process 9

The object compound (I-a) or a salt thereof can be prepared by subjecting the compound (I-b) or a salt thereof to a removal reaction of the acyl group of $R_c{}^1$.

This removal reaction can be carried out by a conventional method in the peptide chemistry such as solvolysis, reduction, and the like, the details of which can be referred to those of Process 4.

Process 10

The object compound (I-l) or a salt thereof can be prepared by subjecting a compound (I-k) or a salt thereof to removal reaction of the carboxy-protective group in $R_c{}^4$.

Suitable salts of the compound (I-k) and (I-l) can be referred to ones as exemplified for the compound (I).

This removal reaction can be carried out by a conventional method in the peptide chemistry such as solvolysis, reduction, and the like, the details of which can be referred to those of Process 4.

Process 11

The object compound (I-n) or a salt thereof can be prepared by subjecting a compound (I-m) or a salt thereof to removal reaction of the imino-protective group in $R_a{}^3$.

Suitable salts of the compound (I-m) and (I-n) can be referred to ones as exemplified for the compound (I).

This removal reaction can be carried out by a conventional method in the peptide chemistry such as solvolysis, reduction, and the like, the details of which can be referred to those of Process 4.

Process 12

The object compound (I-p) or a salt thereof can be prepared by subjecting a compound (I-o) or a salt thereof to removal reaction of the amino or imino-protective group in $R_a{}^4$.

Suitable salts of the compound (I-o) and (I-p) can be referred to ones as exemplified for the compound (I).

This removal reaction can be carried out by a conventional method in the peptide chemistry such as solvolysis, reduction, and the like, the details of which can be referred to those of Process 4.

The compounds obtained by the above processes can be isolated and purified by a conventional method such as pulverization, recrystallization, column chromatography, reprecipitation, or the like.

The object compound (I) can be transformed into its salt in a conventional manner.

The method for preparing the new starting compounds are explained in detail in the following.

Method 1

[Step 1]

The compound (III-a) or a salt thereof can be prepared by reacting the compound (VII) or its reactive derivative at the carboxy group, or a slat thereof with the compound (VI) or its reactive derivative at the amino group, or a salt thereof.

Suitable salts of the compound (VII) and its reactive derivative can be referred to the ones as exemplified for the compound (II).

Suitable salts of the compound (VIII) and its reactive derivative can be referred to the ones as exemplified for the compound (III).

This reaction can be carried out in substantially the same manner as Process 1, and therefore the reaction mode and reaction conditions [e.g. reactive derivatives, solvents, reaction temperature; etc.] of this reaction are to be referred to those as explained in Process 1.

[Step 2]

The compound (II) or a salt thereof can be prepared by subjecting the compound (III-a) or a salt thereof to a removal reaction of the amino-protective group of $R^8$ in a conventional manner such as those explained in Process 4.

Method 2

[Step 1]

The compound (IX) or a salt thereof can be prepared by reacting the compound (II) or its reactive derivative at the carboxy group, or a salt thereof with the compound (VIII) or its reactive derivative at the amino group, or a salt thereof.

Suitable salts of the compound (IX) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

[Step 2]

The compound (V) or a salt thereof can be prepared by subjecting the compound (IX) or a salt thereof to a removal reaction of the carboxy-protective group of $R^9$ in a conventional manner such as those explained in Process 4.

It is to be noted that the compound (I) and the other compounds may include one or more stereoisomers due to asymmetric carbon atoms, and all of such isomers and mixture thereof are included within the scope of this invention.

The object compound (I) and a pharmaceutically acceptable salt thereof have pharmacological activities such as endothelin antagonistic activity, for example, relaxating activity of blood vessel, and the like, and useful for therapeutical treatment and prevention of endothelin mediated diseases such as hypertension (e.g. essential hypertension, pulmonary hypertension, renal hypertension, etc.), heart disease such as angina pectoris, cardiomyopathy, vasospastic angina, myocardial infarction, heart failure, or the like, cerebral stroke such as cerebral arterial spasm, cerebral ischemia, cerebral infarction, cerebral embolus, cerebrovascular twitch, cerebral hemorrhage, or the like, late phase cerebral spasm after subarachnoid hemorrhage, asthma such as bronchial asthma, or the like, renal failure such acute or chronic renal failure, renal insufficiency caused by pharmaceutical (e.g. Cisplatin, Cyclosporins, FK506, etc.), peripheral circulatory failure such as Takayushi's disease, Raynaud'd disease, Buerger's disease, etc, arteriosclerosis, diabetic angiopathy such as diabetic nephropathy, diabetic retinopathy, shock such as hemorrhagic shock, shock induced by endotoxins, etc, malignant hemangioendothelioma, organopathy after reperfusion [e.g. after organ and tissue transplantation, myocardial reperfusion injury, percutaneous transluminal coronary angiopathy (PTCA), or percutaneous transluminal coronary recanalization (PTCR), etc.], bloodstream disturbance after an operation, ulcer, irritable bowel syndrome (IBS), dysuria, retinopathy, dysmenorrhea, premature birth such as premature labor, threatened abortion, or the like, glaucoma, reocclusion after operation of PTCA, adult respiratory distress syndrome (ARDS), and the like.

For therapeutic purpose, the peptide compound (I) and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, sublingual tablet, suppositories, ointment, aerosol, infusion, ophthalmic solutions, vaginal suppository, and the like. If desired, there may be included in these preparations, auxiliary substances, stabilizing agents, wetting or emulsifying agents, buffers and other commonly used additives.

While the dosage of the compound (I) will vary depending upon the age and condition of the patient, in the case of intravenous administration, a daily dose of 0.01-100 mg of the active ingredient per kg weight of human being, in the case of intramuscular administration, a daily dose of 0.05-100 mg of the same per kg weight of human being, in case of oral administration, a daily dose of 0.1-100 mg of the same per kg weight of human being is generally given for the treatment of endothelin-mediated diseases.

In order to illustrate the usefulness of the object compound (I), the pharmacological test data of some representative compounds of the compound (I) are shown in the following.

Test 1

Radioligand binding assay:

(1) Test Compounds
 a. Compound A [The compound of Example 7-2)]
 b. Compound B [The compound of Example 296]
 c. Compound C [The compound of Example 325]
 d. Compound D [The compound of Example 319]
 e. Compound E [The compound of Example 379]
 f. Compound F [The compound of Example 17]

(2) Test Method (a) Crude receptor membrane preparation:

Porcine aorta was purchased from Pel-Freez Biologicals (U.S.A.) and stored at $-80°$ C. until use.

Porcine aorta (50 g) was thawed and dissected free from fatty tissue, minced with scissors and then homogenized with a polytron (Brinkmann PT-20, maximal speed for $3 \times 10$ sec) in 100 ml buffer (0.25M sucrose, 10 mM Tris-HCl, 0.1 mM EDTA).

The homogenate was centrifuged at 10,000 g for 20 minutes at $4°$ C.

The supernatant, containing the plasma membrane fraction, was centrifuged at 100,000 g for 60 minutes at $4°$ C., and then resultant pellets were referred to as crude membrane fractions.

The pellets were resuspended in 25 ml of binding assay buffer (50 mM Tris-HCl, 100 mM NaCl, 5 mM $MgCl_2$, 1.5 $\mu g/ml$ phenylmethylsulfonyl fluoride (PMSF), 120 $\mu g/ml$ bacitracin, 12 $\mu g/ml$ leupepcin, 6 $\mu g/ml$ chymostain, 0.1% bovine serum albumin (BSA), pH 7.5).

The aorta membrane fractions were stored at $-80°$ C. until use.

(b) $^{125}$I-endothelin-1 binding assay:

$^{125}$I-Endothelin-1 ($1.67 \times 10^{-11}M$) (Amersham Japan, specific activity: 2000 Ci/m mol) was incubated with 50 $\mu l$ of aorta membrane preparation in binding assay buffer at room temperature ($20°-22°$ C.) for 60 minutes in a final volume of 250 $\mu l$.

After incubation, the incubation mixture were filtered through Glass-fiber GF/C filter (pretreated with 0.1% polyethylene imine for 3 hours prior to use) using cell harvester (Brandel M-24S). The filters were then washed ten times with a total of 3 ml of the washing buffer (50 mM Tris-HCl, pH 7.5) at $0°$ C. The filters were counted in a gamma counter (Packard Auto Gamma Model 5650).

(3) Test Results

The results are shown in Table 1.

TABLE 1

| Effect on specific binding of $^{125}$I-endothelin-1 in porcine aorta membrane | |
|---|---|
| Test Compound | $IC_{50}(M)$ |
| A | $2.3 \times 10^{-9}$ |
| B | $3.2 \times 10^{-8}$ |
| C | $7.6 \times 10^{-9}$ |
| D | $2.1 \times 10^{-8}$ |
| E | $7.6 \times 10^{-9}$ |

Test 2

Effect on rabbit aorta or contraction response of endothelin:

(1) Test Compound
 Test Compound A (2) Test Method

Thoracic aorta were isolated from freshly killed male albino rabbits (11 weeks old) and cut into 25 mm strips with the intima denuded. After removing fatty tissues, these arterial segments (2 mm width and 25 mm length) were suspended in 25 ml organ chambers filled with Krebs-Ringer solution (113 mM NaCl, 4.8 mM KCl, 2.2 mM $CaCl_2$, 1.2 mM $MgCl_2$, 25 mM $NaHCO_3$, 1.2 mM $KH_2PO_4$, 5.5 mM glucose) maintained at $37°$ C. and gassed with 95% $O_2$/5% $CO_2$.

A preload of 0.5 g was applied after the aorta had been conditioned by application of increasing concentration of KCl. Contractions were measured as an increase in isometric tension.

Test Compound was tested against contractile response of rabbit aorta induced by endothelin ($3.2 \times 10^{-9}$M). Synthetic endothelin was obtained from Peptide Institute Inc. (Osaka, Japan). Test Compound was added after the full contraction response induced by endothelin.

(3) Test Result

The activity of Test Compound is expressed as the $IC_{50}$ value of maximum contraction response induced by endothelin and shown in Table 2.

TABLE 2

| Test Compound | Effect on the contractile responses of rabbit thoracic aorta induced by endothelin |
|---|---|
| | Inhibition against contraction response of endothelin ($IC_{50}$) |
| A | $2.3 \times 10^{-7}$M |

Test 3

Effect on endothelin-1-pressor response (1) Test Compound

Test Compound A (2) Test Method

Wistar rats, weighing 200 g to 250 g, were anesthetized with ether, and the abdominal aorta was canulated with a polyethylene tube via the femoral artery and vein for blood pressure measurement and intravenous injection of endothelin-1. The animals were allocated to recover for 3 hours and tethered in each cage. The blood pressure was directly monitored via pressure transducer (PT-200T, made by Nihon Kohden) and were recorded on a pre-writing recorder (CWT685G, made by Nihon Kohden). Pressor response to intravenous injection of endothelin-1 (3.2 μg/kg) was obtained.

This dose produced a sustained pressor response which continued over 1 hour.

The effect of intravenous injection of the Test Compound was studied in rats 20 minutes after starting an intravenous injection of endothelin-1.

(3) Test Result

Potency of the Test Compound in rats was expressed by the following index.

| | Dose (mg/kg) | Response |
|---|---|---|
| A | 10 | ++ |

++: completely antagonized (almost 100%) +: moderately antagonized (about 50%) −: no effect Test 4

Effect on myocardial infarction (1) Test Compound

Compound F (2) Test Method

Male SD rats weighing 250–400 g were anesthetized with sodium pentobarbital (50 mg/kg i.p.).

The left side of the thorax was opened under artificial repiration.

The left coronary artery was ligated about 5–6 mm from its origin for 60 minutes and reperfused for 24 hours.

The test drug was administered subcutaneously 60 minutes before coronary ligation.

The hearts were removed immediately, weighed and sectioned in transvers ring 2.0 mm thick from apex to base.

The atrium was separated and discarded.

To determine the myocardial infarct size, the tissue were rinsed in cold isotonic saline solution and then incubated at 37° C. for 20 minutes in a phosphate buffer solution of triphenyltetrazolium chloride.

The unstained region of ventricule (infarct area) was separated from stained region (normal area).

The index of the myocardial infarction was calculated according to the following formula.

$$\frac{\text{Weight of unstained region}}{\text{weight of total ventricule}} \times 100 \, (\%)$$

(3) Test Results

The results are shown in Table 4.

TABLE 4

| | Effect on myocardial infarction. | | |
|---|---|---|---|
| Test Compound | dose (mg/kg) | n | Index of myocardial infarction (%) |
| Vehicle | 0 | 8 | 18.3 |
| F | 100 | 5 | 10.6 |

Test 5

Effect on intimal thickening of carotid artery after endothelial denudation with balloon catheter in rats.

(1) Test Compound

Compound F (2) Test Method 14 male 17-week-old Sprague-Dawley rats were anethetized with sodium pentobarbital (50 mg/kg). The distal left common carotid and external carotid arteries were exposed through a midline incision in the neck. The left carotid artery was denuded of endothelium by the intraluminal passage of a Fogarty 2F balloon catheter introduced through the external carotid artery. The catheter was passed three times with the balloon distended sufficiently with saline to generate slight resistance. The external carotid artery was ligated after removal of the catheter and the wound was closed.

After 14 days, the animals were anethetized and infused with saline containing heparin (20 unit/ml). The left carotid arteries were removed and placed in 10% buffered formalin for fixation. The central part of each segments were embedded in paraffin for cross-sectioning. Semi-thin section (3 um) were stained with Orcein. The cross-sectional area of the neointima(I) and the media(M) were measured with an image analyzer (LUZEX 2D, Nikon).

Test compound was administered subcutaneously at the dose of 100 mg/kg, once a day, from 2 days before to 13 days after balloon injury.

(3) Test Result

The results are shown in Table 5.

TABLE 5

| | Effect on intimal thickening of carotid artery | | | |
|---|---|---|---|---|
| Test Compound | area of neointima (mm$^2$) | inhibition (%) | (I)/(M) | inhibition (%) |
| Vehicle | 0.170 ± 0.034 | — | 0.850 ± 0.166 | — |
| F | 0.098 ± 0.028 | 42.4 | 0.615 ± 0.182 | 27.7 |

From the results of the above-mentioned biological test, it is clear that compound (I) has endothelin antagonistic activity, therefore are useful for the treatment and prevention of endothelin mediated diseases, for example, hypertension, heart disease such as angina pectoris, cardiomyopathy, myocardial infarction or the like, organopathy after reperfusion [e.g. after organ and tissue plantation, myocardial reperfusion injuly, PTCA, PTCR, etc.], cerebral stroke such as cerebral arterial spasm, cerebral ischemia, cerebrovascular twitch or the like, late phase cerebral spasm after subarachnoid hemorrhage, asthma such as bronchial asthma, or the like renal failure such as chronic or acute renal failure, renal insufficiency caused by pharmaceuticals (e.g. Cisplatin, Cyclosporins, etc.), or the like.

The following examples are given for purpose of illustrating the present invention in detail.

In these examples, there are employed the following abbreviations in addition to the abbreviations adopted by the IUPAC-IUB.

Ac: acetyl
Boc: t-butoxycarbonyl
Bu: butyl
Bzl: benzyl
DMF: dimethylformamide
DMSO: dimethyl sulfoxide
Et: ethyl
HOBT: N-hydroxybenzotriazole
Me: methyl
NMM: N-methylmorpholine
Pac: phenacyl
D-Pya: D-(2-pyridyl)alanine
D-4Pya: D-(4-pyridyl)alanine
TFA: trifluoroacetic acid
TEA: triethylamine
Ts or Tos: tosyl
WSCD: 1-ethyl-3-(3-dimethylaminopropyl)carbodiimide
Z: benzyloxycarbonyl
DMAP: dimethylaminopyridine Preparation 1-1)

To a mixture of Boc-D-Trp($CH_3$)-OH (1.59 g), HCl.H-D-Phe-OCH$_3$ (1.08 g) and HOBT (0.81 g) in DMF (20 ml) was added WSCD (0.93 g) under ice-bath cooling. After being stirred for 2 hours at room temperature, the mixture was concentrated in vacuo and the residue was dissolved in ethyl acetate (50 ml). The solution was washed with 0.5N hydrochloric acid (20 ml), water (20 ml), saturated sodium bicarbonate (20 ml) and water (20 ml×2) successively, dried over magnesium sulfate and evaporated in vacuo. The residue was triturated with ether to give Boc-D-Trp($CH_3$)-D-Phe-OCH$_3$ (1.45 g).

mp: 95°–96° C. Rf: 0.83 (CHCl$_3$:MeOH=9:1)

Preparation 1-2)

A solution of Boc-D-Trp($CH_3$)-D-Phe-OCH$_3$ (1.40 g) in a mixture of anisole (1.4 ml) and TFA (14 ml) was stirred for one hour at 0° C. The mixture was concentrated in vacuo and dissolved in 4N HCl in 1,4-dioxane (10 ml) and the solution was concentrated in vacuo. The residue was triturated with ether to give HCl.H-D-Trp($CH_3$)-D-Phe-OCH$_3$ (1.09 g).

mp: 188°–192° C. Rf: 0.51 (CHCl$_3$:MeOH=9:1)

Preparation 1-3)

Phenylacetyl chloride (5.7 ml) was added dropwise to a mixture of TsOH.H-L-Leu-OBzl (14.15 g) and TEA (12 ml) in dichloromethane (300 ml) under ice-bath cooling. After being stirred for 10 minutes at the same temperature, the mixture was concentrated in vacuo, and the residue was dissolved in ethyl acetate (300 ml). The solution was washed with 1N HCl (100 ml), water (100 ml), 1M aqueous sodium bicarbonate (100 ml), and brine (100 ml×2), dried over magnesium sulfate and evaporated to give N-phenylacetyl-L-Leu-OBzl (14 g). This product was used in a next step without further purification.

Rf: 0.50 (CHCl$_3$:MeOH=9:1)

Preparation 1-4)

A solution of N-phenylacetyl-L-Leu-OBzl (14 g) in methanol (140 ml) was hydrogenated over 10% palladium on carbon (1.4 g) at 3 atmospheric pressure of hydrogen for 2 hours. After removal of the catalyst by filtration, the filtrate was concentrated in vacuo. The residue was triturated with diisopropyl ether to give N-phenylacetyl-L-Leu-OH (7.7 g).

mp: 135°–136° C. Rf: 0.17 (CHCl$_3$:MeOH=9:1)

Preparation 2-1)

Boc-D-Trp($CH_3$)-D-Phe-OBzl was obtained in 87.2% yield in substantially the same manner as that of Preparation 1-1).

Rf: 0.77 (CHCl$_3$:MeOH=9:1)

Preparation 2-2)

HCl.H-D-Trp($CH_3$)-D-Phe-OBzl was obtained quantitatively in substantially the same manner as that of Preparation 1-2).

mp: 147°–150° C. Rf: 0.57 (CHCl$_3$:MeOH=9:1)

Preparation 3-1)

Boc-L-Leu-OH (1.30 g), HCl.H-D-Trp($CH_3$)-OBzl (1.76 g), WSCD (950 mg) and HOBT (827 mg) in DMF (30 ml) was reacted at 5° C. overnight in a similar manner to that of Preparation 1-1) to give Boc-L-Leu-D-Trp($CH_3$)-OBzl (2.48 g).

mp: 124°–126° C. Rf: 0.87 (CHCl$_3$:MeOH=9:1)

Preparation 3-2)

Boc-L-Leu-D-Trp($CH_3$)-OBzl (2.40 g) in MeOH (50 ml) and water (1 ml) was hydrogenated over 10% palladium on carbon in a similar manner to that of Preparation 1-4) to give Boc-L-Leu-D-Trp($CH_3$)-OH (1.95 g).

mp: 64°–67° C. Rf 0.57 (CHCl$_3$:MeOH:AcOH=16:1:1)

Preparation-4-1)

N-Phenylacetyl-L-Leu-D-Trp($CH_3$)-OBzl (5.96 g) was obtained from N-phenylacetyl-L-Leu-OH (2.96 g), HCl.H-D-Trp($CH_3$)-OBzl (3.9 g), HOBT (1.68 g) and WSCD (1.93 g) in a similar manner to that of Preparation 1-1).

mp: 152°–155° C. Rf: 0.72 (CHCl$_3$:MeOH=9:1)

Preparation 4-2)

To a solution of N-phenylacetyl-L-Leu-D-Trp($CH_3$)-OBzl (5.9 g) in a mixture of methanol (60 ml), acetic acid (60 ml) and DMF (100 ml) was added 10% palladium on activated carbon (0.6 g). The mixture was stirred for 5 hours at 3 atmospheric pressure of hydrogen at room temperature. The solution was filtered and the filtrate was concentrated in vacuo. The residue was triturated with ether-ethyl acetate to give N-phenylacetyl-L-Leu-D-Trp($CH_3$)-OH (4.69 g).

mp: 76°–79° C. Rf: 0.50 (CHCl$_3$:MeOH:AcOH=16:1:1)

Preparation 5

Boc-D-Trp($CH_3$)-OH (6.0 g), D-Pya-OC$_2$H$_5$.2HCl (5.54 g), WSCD (3.51 g), HOBT (3.05 g) and TEA (2.09 g) were reacted in DMF (200 ml) in a similar manner to that of Preparation 1-1) to give Boc-D-Trp($CH_3$)-D-Pya-OC$_2$H$_5$ (6.18 g).

mp: 99°–101° C. Rf: 0.67 (CHCl$_3$:MeOH=9:1)

Preparation 6

Boc-D-Trp($CH_3$)-D-Pya-OC$_2$H$_5$ (4.50 g), TFA (50 ml) and anisole (5 ml) were reacted in a similar manner to that of Preparation 1-2) to give 2HCl.H-D-Trp($CH_3$)-D-Pya-OC$_2$H$_5$ (4.15 g).

mp: 81°–83° C. Rf: 0.22 (CHCl$_3$:MeOH-:AcOH=8:1:1)

Preparation 7

To a solution of (S)-α-benzyloxycarbonyl-γ-methylbutyl isocyanate (1.50 g) in ethyl acetate (60 ml) was added hexahydro-1H-azepine (722 mg) at room temperature. After being stirred for 30 minutes at the same temperature, the solution was washed with 5% HCl, 1M sodium bicarbonate solution and saturated sodium chloride solution successively, and dried over anhydrous magnesium sulfate. The solution was concentrated in vacuo to give N-(hexahydro-1H-azepin-1-ylcarbonyl)-L-Leucine benzyl ester (2.06 g) as a crystal.

mp: 79°–82° C. Rf: 0.64 (n-hexane:EtOAc=1:1)

Preparation 8

(2S)-2-Amino-3,3-dimethyl-N,N-dimethylbutyramide hydrochloride (0.20 g), (S)-α-benzyloxycarbonyl-γ-methylbutyl isocyanate (0.25 g) and TEA (0.1 ml) were reacted in ethyl acetate (10 ml) in a similar manner to that of Preparation 7 to give N-[(1S)-2,2-dimethyl-1-(N,N-dimethylcarbamoyl)propyl]carbamoyl]-L-Leu-OBzl (0.40 g).

Rf: 0.59 (hexane:EtOAc=2:1)

Preparation 9

(S)-α-Benzyloxycarbonyl-γ-methylbutyl isocyanate (500 mg) and octahydroazocine (275 mg) were reacted in a similar manner to that of Preparation 7 to give N-(octahydroazocin-1-ylcarbonyl)-L-Leu-OBzl (680 mg).

mp: 87°–89° C. Rf: 0.65 (n-hexane:EtOAc=1:1)

Preparation 10

(2S)-2-Amino-3,3-dimethyl-N,N-dimethylbutyramide hydrochloride (0.25 g), (2S)-2-chlorocarbonyloxy-4-methylvaleric acid benzylester (0.36 g) and TEA (0.31 g) were reacted in ethyl acetate (10 ml) in a similar manner to that of Example 4-1) to give (2S)-2-[N-[(1S)-2,2-dimethyl-1-(N,N-dimethylcarbamoyl)propyl]carbamoyloxy]-4-methylvaleric acid benzyl ester (0.44 g).

Rf: 0.42 (hexane:EtOAc=2:1)

Preparation 11

Benzyl (2R)-2-carboxymethyl-4-methylvalerate (1.35 g), hexahydro-1H-azepine (0.610 g) and WSCD.HCl (1.18 g) were reacted in methylene chloride (30 ml) in a similar manner to that of Preparation 1-1) to give benzyl (2R)-2-(hexahydro-1H-azepin-1-ylcarbonylmethyl)-4-methylvalerate (1.65 g).

Rf: 0.87 (benzene:EtOAc:AcOH=20:20:1)

Preparation 12

The following compounds were obtained by catalytic reduction of the corresponding benzyl esters in a similar manner to that of Preparation 4-2).

1) N-[(1S)-2,2-Dimethyl-1-(N,N-dimethylcarbamoyl)propyl]carbamoyl]-L-Leu-OH.
   mp: 90°–93° C. Rf: 0.50 (CHCl$_3$:MeOH:AcOH=16:1:1)
2) (2S)-2-[N-[(1S)-2,2-Dimethyl-1-(N,N-dimethylcarbamoyl)propyl]carbamoyloxy]-4-methylvaleric acid.
   mp: 146°–148° C. Rf: 0.20 (CHCl$_3$:MeOH=9:1)
3) N-(Hexahydro-1H-azepin-1-ylcarbonyl)-L-Leu-OH.
   Rf: 0.40 (benzene:EtOAc:AcOH=20:20:1)
4) (2R)-2-(Hexahydro-1H-azepin-1-ylcarbonylmethyl)-4-methylvaleric acid.
   Rf: 0.55 (benzene:EtOAc:AcOH=20:20:1)
5) N-(Octahydroazocin-1-ylcarbonyl)-L-Leu-OH.
   Rf: 0.45 (benzene:EtOAc:AcOH=20:20:1)

Preparation 13

The following compounds could be obtained by reacting the corresponding starting compounds with 2HCl.H-D-Pya-OC$_2$H$_5$ in the presence of NMM in a similar manner to that of Preparation 1-1).

1) Boc-D-Trp(i-C$_4$H$_9$)-D-Pya-OC$_2$H$_5$
   mp: 60°–62° C. Rf: 0.62 (CHCl$_3$:MeOH=9:1)
2) Boc-D-Trp(CHO)-D-Pya-OC$_2$H$_5$
   mp: 131°–134° C. Rf: 0.60 (CHCl$_3$:MeOH=9:1)
3) Boc-D-Trp(C$_2$H$_5$)-D-Pya-OC$_2$H$_5$
   mp: 64°–67° C. Rf: 0.61 (CHCl$_3$:MeOH=9:1)
4) Boc-D-Trp(n-C$_3$H$_7$)-D-Pya-OC$_2$H$_5$
   mp: 62°–63° C. Rf: 0.60 (CHCl$_3$:MeOH=9:1)

Preparation 14

The following compounds could be obtained by removing tert-butoxycarbonyl groups from the corresponding starting compounds with TFA and anisole in a similar manner to that of Preparation 1-2).

1) 2HCl.H-D-Trp(i-C$_4$H$_9$)-D-Pya-OC$_2$H$_5$
   Rf: 0.09 (CHCl$_3$:MeOH=9:1)
2) 2HCl.H-D-Trp(CHO)-D-Pya-OC$_2$H$_5$
   Rf: 0.15 (CHCl$_3$:MeOH=9:1)
3) HCl.H-D-Trp(C$_2$H$_5$)-D-Pya-OC$_2$H$_5$
   Rf: 0.15 (CHCl$_3$:MeOH=9:1)
4) HCl.H-D-Trp(n-C$_3$H$_7$)-D-Pya-OC$_2$H$_5$
   Rf: 0.13 (CHCl$_3$:MeOH=9:1)

Preparation 15

The following compounds could be obtained by reacting (S)-α-benzyloxycarbonyl-γ-methylbutyl isocyanate with the corresponding amines in a similar manner to that of Preparation 7.

1) N-(Thiomorpholinocarbonyl)-L-Leu-OBzl
   mp: 89°–91° C. Rf: 0.53 (n-hexane:AcOEt=1:1)
2) N-(1,2,3,4-Tetrahydroisoquinolin-2-ylcarbonyl)-L-Leu-OBzl
   Rf: 0.71 (n-hexane:AcOEt=1:1)
3) N-(1,2,3,4-Tetrahydroquinolin-1-ylcarbonyl)-L-Leu-OBzl
   Rf: 0.62 (n-hexane:AcOEt=2:1)
4) N-(N,N-Dibutylcarbamoyl)-L-Leu-OBzl
   Rf: 0.70 (n-hexane:AcOEt=2:1)
5) N-(N,N-Dipropylcarbamoyl)-L-Leu-OBzl
   Rf: 0.69 (n-hexane:AcOEt=2:1)
6) N-(N-Heptylcarbamoyl)-L-Leu-OBzl
   Rf: 0.63 (n-hexane:AcOEt=2:1)
7) N-(N,N-Diisobutylcarbamoyl)-L-Leu-OBzl
   Rf: 0.76 (n-hexane:AcOEt=2:1)
8) N-(N-Cyclohexyl-N-methylcarbamoyl)-L-Leu-OBzl
   Rf: 0.82 (n-hexane:AcOEt=1:1)
9) N-[4-(N,N-Dimethylcarbamoyl)piperidinocarbonyl]-L-Leu-OBzl
   Rf: 0.53 (CHCl$_3$:MeOH:AcOH=16:1:1)
10) N-(2-Pyridylcarbamoyl)-L-Leu-OBzl
    Rf: 0.61 (CHCl$_3$:MeOH=9:1)
11) N-[(2S)-2-(N,N-Dimethylcarbamoyl)pyrrolidin-1-ylcarbonyl]-L-Leu-OBzl
    Rf: 0.47 (CHCl$_3$:MeOH=9:1)
12) N-[(2R)-2-(N,N-Dimethylcarbamoyl)pyrrolidin-1-ylcarbonyl]-L-Leu-OBzl
    Rf: 0.51 (CHCl$_3$:MeOH=9:1)
13) N-[1-(N,N-Dimethylcarbamoyl)cyclohexylcarbamoyl]-L-Leu-OBzl
    mp: 145°–148° C. Rf: 0.61 (CHCl$_3$:MeOH=9:1)
14) N-[(1S,2S)-1-(N,N-Diethylcarbamoyl)-2-methylbutylcarbamoyl]-L-Leu-OBzl
    Rf: 0.31 (n-hexane:AcOEt=2:1)
15) N-(1,2,3,6-Tetrahydropyridin-1-ylcarbonyl)-L-Leu-OBzl
    Rf: 0.49 (n-hexane:AcOEt=2:1)

16) N-(2,6-Dimethylpiperidinocarbonyl)-L-Leu-OBzl
mp: 81°–83° C. Rf: 0.53 (n-hexane:AcOEt=2:1)
17) N-(3,5-Dimethylpiperidinocarbonyl)-L-Leu-OBzl
Rf: 0.60 (n-hexane:AcOEt=2:1)
18) N-(N,N-Dicyclohexylcarbamoyl)-L-Leu-OBzl
mp: 100°–103° C. Rf: 0.80 (n-hexane:AcOEt=2:1)
19) N-(N,N-Diethylcarbamoyl)-L-Leu-OBzl
Rf: 0.45 (n-hexane:AcOEt=2:1)
20) N-(N,N-Diisopropylcarbamoyl)-L-Leu-OBzl
Rf: 0.65 (n-hexane:AcOEt=2:1)
21) N-[N-Methyl-N-[(1S)-3-methyl-1-(N,N-dimethylcarbamoyl)butyl]carbamoyl]-L-Leu-OBzl
mp: 183°–187° C. Rf: 0.38 (CHCl$_3$:MeOH:AcOH=16:1:1)
22) N-[(1S)-1-(N,N-Dimethylcarbamoyl)pentylcarbamoyl]-L-Leu-OBzl
mp: 133°–136° C. Rf: 0.59 (n-hexane:AcOEt=2:1)
23) N-[N-Methyl-N-[(1S,2S)-1-(N,N-dimethylcarbamoyl)-2-methylbutyl]carbamoyl]-L-Leu-OBzl
Rf: 0.60 (n-hexane:AcOEt=2:1)
24) N-[(1S)-1-(N,N-Dimethylcarbamoyl)ethylcarbamoyl)]L-Leu-OBzl
Rf: 0.55 (n-hexane:AcOEt=2:1)

Preparation 16

To a solution of benzyl (2S)-2-chlorocarbonyloxy-4-methylvalerate (0.56 g) in tetrahydrofuran (11 ml) was added cyclohexylamine (0.40 g) at room temperature. After being stirred for 10 minutes, the solvent was removed by evaporation under reduced pressure, and the residue was dissolved in ethyl acetate (30 ml). The solution was washed with 1N HCl, water and brine successively. The organic layer was dried over magnesium sulfate and concentrated in vacuo. The residual solid was triturated with hexane to give benzyl (2S)-2-cyclohexylcarbamoyloxy-4-methylvalerate (0.45 g).

mp: 89°–90° C. Rf: 0.70 (n-hexane:AcOEt=2:1)

Preparation 17

The following compounds could be obtained by reacting benzyl (2S)-2-chlorocarbonyloxy-4-methylvalerate with the corresponding amines in a similar manner to that of Preparation 16.
1) Benzyl (2S)-4-methyl-2-[(2S)-2-methylbutylcarbamoyloxy]valerate
mp : 48°–49° C. Rf: 0.69 (n-hexane:AcOEt=2:1)
2) Benzyl (2S)-4-methyl-2-[(1S,2S)-2-methyl-1-(N,N-dimethylcarbamoyl)butylcarbamoyloxy]valerate
Rf: 0.91 (CHCl$_3$:MeOH=9:1)
3) Benzyl (2S)-4-methyl-2-[(1R,2S)-2-methyl-1-(N,N-dimethylcarbamoyl)butylcarbamoyloxy]valerate
Rf: 0.36 (n-hexane:AcOEt=2:1)
4) Benzyl (2S)-4-methyl-2-[(1S)-2-methyl-1-(N,N-dimethylcarbamoyl)propylcarbamoyloxy]valerate
Rf: 0.36 (n-hexane:AcOEt=2:1)
5) Benzyl (2S)-4-methyl-2-[(1S)-3-methyl-1-(N,N-dimethylcarbamoyl)butylcarbamoyloxy]valerate
Rf: 0.37 (n-hexane:AcOEt=2:1)
6) Benzyl (2S)-4-methyl-2-[(1S,2S)-2-methyl-1-(piperidinocarbonyl)butylcarbamoyloxy]valerate
Rf: 0.36 (n-hexane:AcOEt=2:1)
7) Benzyl (2S)-4-methyl-2-[(1S,2S)-1-carbamoyl-2-methylbutylcarbamoyloxy]valerate
mp: 140°–141° C. Rf: 0.13 (n-hexane:AcOEt=2:1)
8) Benzyl (2S)-2-[(1S,2S)-1-(isopropylcarbamoyl)-2-methylbutylcarbamoyloxy]-4-methylvalerate
mp: 90°–92° C. Rf: 0.67 (n-hexane:AcOEt=2:1)
9) Benzyl (2S)-4-methyl-2-(piperidinocarbonyloxy)valerate
Rf: 0.70 (n-hexane:AcOEt=2:1)
10) Benzyl (2S)-2-[(1S,2S)-1-(cyclohexylcarbamoyl)-2-methylbutylcarbamoyloxy]-4-methylvalerate
mp: 98°–100° C. Rf: 0.55 (n-hexane:AcOEt=2:1)
11) Benzyl (2S)-2-(hexahydro-1H-azepin-1-ylcarbonyloxy)-4-methylvalerate
Rf: 0.78 (n-hexane:AcOEt=2:1)
12) Benzyl (2S)-2-(1,2,3,4-tetrahydroisoquinolin-2-ylcarbonyloxy)-4-methylvalerate
Rf: 0.68 (n-hexane:AcOEt=2:1)

Preparation 18

To a solution of benzyl (2R)-2-carboxymethyl-4-methylvalerate (527 mg) and cyclohexylamine (238 mg) in methylene chloride (10 ml) was added WSCD.HCl (460 mg) at room temperature. After being stirred overnight, the mixture was concentrated in vacuo and the residue was dissolved in ethyl acetate (30 ml). The solution was washed with 5% HCl, water, saturated sodium bicarbonate and water, dried over magnesium sulfate and evaporated in vacuo. The residue was triturated with n-hexane to give benzyl (2R)-2-(cyclohexylcarbamoylmethyl)-4-methylvalerate (410 mg).

mp: 99°–102° C. Rf: 0.84 (benzene:AcOEt:AcOH=20:20:1)

Preparation 19

Benzyl (2R)-2-carboxymethyl-4-methylvalerate (320 mg), octahydroazocin (165 mg) and WSCD.HCl (280 mg) were reacted in methylene chloride (20 ml) in a similar manner to that of Preparation 18 to give benzyl (2R)-2-(octahydroazocin-1-ylcarbonylmethyl)-4-methylvalerate (378 mg).

Rf: 0.83 (benzene:AcOEt:AcOH=20:20:1)

Preparation 20

The following compounds could be obtained by reducing the corresponding benzylester compounds in the presence of 10% palladium on carbon in a similar manner to that of Preparation 1-4).
1) N-(1,2,3,4-Tetrahydroisoquinolin-2-ylcarbonyl)-L-Leu-OH
mp: 93°–95° C. Rf: 0.32 (benzene:AcOEt:AcOH=20:20:1)
2) N-(1,2,3,4-Tetrahydroquinolin-1-ylcarbonyl)-L-Leu-OH
Rf: 0.46 (benzene:AcOEt:AcOH=20:20:1)
3) N-(N,N-Dibutylcarbamoyl)-L-Leu-OH
mp: 121°–123° C. Rf: 0.51 (benzene:AcOEt:AcOH=20:20:1)
4) N-(N,N-Dipropylcarbamoyl)-L-Leu-OH
Rf: 0.41 (benzene:AcOEt:AcOH=20:20:1)
5) N-(N-Heptylcarbamoyl)-L-Leu-OH
Rf: 0.48 (benzene:AcOEt:AcOH=20:20:1)
6) N-(N,N-Diisobutylcarbamoyl)-L-Leu-OH
mp: 116°–118° C. Rf: 0.39 (benzene:AcOEt:AcOH=20:20:1)
7) N-(N-Cyclohexyl-N-methylcarbamoyl)-L-Leu-OH
Rf: 0.51 (benzene:AcOEt:AcOH=20:20:1)
8) N-[4-(N,N-Dimethylcarbamoyl)piperidinocarbonyl]-L-Leu-OH
Rf: 0.10 (CHCl$_3$:MeOH:AcOH=16:1:1)
9) N-(2-Pyridylcarbamoyl)-L-Leu-OH
Rf: 0.19 (CHCl$_3$:MeOH:AcOH=16:1:1)
10) N-[(2S)-2-(N,N-Dimethylcarbamoyl)pyrrolidin-1-ylcarbonyl)-L-Leu-OH
Rf: 0.34 (CHCl$_3$:MeOH:AcOH=16:1:1)
11) N-[(2R)-2-(N,N-Dimethylcarbamoyl)pyrrolidin-1-ylcarbonyl)-L-Leu-OH
Rf: 0.34 (CHCl$_3$:MeOH:AcOH=16:1:1)
12) N-[1-(N,N-Dimethylcarbamoyl)cyclohexylcarbamoyl]-L-Leu-OH mp: 191°-192° C. Rf: 0.35 (CHCl₃:MeOH:AcOH=16:1:1)
13) N-[(1S,2S)-1-(N,N-Dimethylcarbamoyl)-2-methylbutylcarbamoyl]-L-Leu-OH
Rf: 0.35 (CHCl₃:MeOH:AcOH=16:1:1)
14) N-(2,6-Dimethylpiperidinocarbonyl)-L-Leu-OH
Rf: 0.53 (CHCl₃:MeOH:AcOH=16:1:1)
15) N-(3,5-Dimethylpiperidinocarbonyl)-L-Leu-OH
Rf: 0.53 (CHCl₃:MeOH:AcOH=16:1:1)
16) N-(N,N-Dicyclohexylcarbamoyl)-L-Leu-OH
mp: 62°-73° C. Rf: 0.42 (CHCl₃:MeOH:AcOH=16:1:1)
17) N-(N,N-Diethylcarbamoyl)-L-Leu-OH
mp: 106°-107° C. Rf: 0.36 (CHCl₃:MeOH:AcOH=16:1:1)
18) N-(N,N-Diisopropylcarbamoyl)-L-Leu-OH
Rf: 0.38 (CHCl₃:MeOH:AcOH=16:1:1)
19) N-[N-Methyl-N-[(1S)-3-methyl-1-(N,N-dimethylcarbamoyl)butyl]carbamoyl]-L-Leu-OH
Rf: 0.38 (CHCl₃:MeOH:AcOH=16:1:1)
20) N-[(1S)-1-(N,N-Dimethylcarbamoyl)pentylcarbamoyl]-L-Leu-OH
mp: 155°-160° C. Rf: 0.34 (CHCl₃:MeOH:AcOH=16:1:1)
21) N-[N-Methyl-N-[(1S,2S)-1-(N,N-Dimethylcarbamoyl)-2-methylbutyl]carbamoyl]-L-Leu-OH
Rf: 0.52 (CHCl₃:MeOH:AcOH=16:1:1)
22) N-[(1S)-1-(N,N-Dimethylcarbamoyl)ethylcarbamoyl)]-L-Leu-OH
Rf: 0.46 (CHCl₃:MeOH:AcOH=16:1:1)
23) (2S)-2-Cyclohexylcarbamoyloxy-4-methylvaleric acid
Rf: 0.45 (CHCl₃:MeOH=9:1)
24) (2S)-4-Methyl-2-[(2S)-2-methylbutylcarbamoyloxy]valeric acid
Rf: 0.40 (CHCl₃:MeOH=9:1)
25) (2S)-4-Methyl-2-[(1S,2S)-2-methyl-1-(N,N-dimethylcarbamoyl)butylcarbamoyloxy]valeric acid
Rf: 0.50 (CHCl₃:MeOH:AcOH=16:1:1)
26) (2S)-4-Methyl-2-[(1R,2S)-2-methyl-1-(N,N-dimethylcarbamoyl)butylcarbamoyloxy]valeric acid
Rf: 0.33 (CHCl₃:MeOH:AcOH=16:1:1)
27) (2S)-4-Methyl-2-[(1S)-2-methyl-1-(N,N-Dimethylcarbamoyl)propylcarbamoyloxy]valeric acid
Rf: 0.31 (CHCl₃:MeOH:AcOH=16:1:1)
28) (2S)-4-Methyl-2-[(1S)-3-methyl-1-(N,N-dimethylcarbamoyl)butylcarbamoyloxy]valeric acid
Rf: 0.35 (CHCl₃:MeOH:AcOH=16:1:1)
29) (2S) -4-Methyl-2-[(1S,2S)-1-carbamoyl-2-methylbutylcarbamoyloxy]valeric acid
mp: 170°-175° C. Rf: 0.50 (CHCl₃:MeOH:AcOH=16:1:1)
30) (2S)-2-[(1S,2S)-1-(Isopropylcarbamoyl)-2-methylbutylcarbamoyloxy]-4-methylvaleric acid
mp: 179°-180° C. Rf: 0.37 (CHCl₃:MeOH:AcOH=16:1:1)
31) (2S)-4-Methyl-2-(Piperidinocarbonyloxy)valeric acid
Rf: 0.56 (CHCl₃:MeOH:AcOH=16:1:1)
32) (2S)-2-[(1S,2S)-1-(Cyclohexylcarbamoyl)-2-methylbutylcarbamoyloxy]-4-methylvaleric acid
mp: 193°-195° C. Rf: 0.43 (CHCl₃:MeOH:AcOH=16:1:1)
33) (2S)-2-(Hexahydro-1H-azepin-1-ylcarbonyloxy)-4-methylvaleric acid
mp: 86°-88° C. Rf: 0.53 (benzene:AcOEt:AcOH=20:20:1)
34) (2S)-2-(1,2,3,4-Tetrahydroisoquinolin-2-ylcarbonyloxy-4-methylvaleric acid
Rf: 0.48 (benzene:AcOEt:AcOH=20:20:1)
35) (2R)-2-(Cyclohexylcarbamoylmethyl)-4-methylvaleric acid
mp: 86°-88° C. Rf: 0.53 (benzene:AcOEt:AcOH=20:20:1)
36) (2R)-2-(Octahydroazocin-1-ylcarbonylmethyl)-4-methylvaleric acid
mp: 79°-81° C. Rf: 0.56 (benzene:AcOEt:AcOH=20:20:1)
37) N-Cyclohexylcarbamoyl-L-Leu-OH
mp: 105°-108° C. Rf: 0.32 (CHCl₃:MeOH=9:1)
38) N-[1-(N,N-Dimethylcarbamoylmethyl)cyclohexylcarbamoyl]-L-Leu-OH
Rf: 0.35 (CHCl₃:MeOH:AcOH=16:1:1)
39) N-Cyclohexylcarbamoyl-L-Leu-D-TrP(CH₃)-OH
mp: 202°-206° C. Rf: 0.51 (CHCl₃:MeOH:AcOH=8:1:1)
40) N-(Piperidinocarbamoyl)-L-Leu-OH
mp: 185°-187° C. Rf: 0.70 (CHCl₃:MeOH=9:1)
41) N-[(2S)-2-Methylbutylcarbamoyl]-L-Leu-OH
Rf: 0.22 (CHCl₃:MeOH:AcOH=8:1:1)
42) N-(2-Pyridylmethylcarbamoyl)-L-Leu-OH
mp: 183°-185° C. Rf: 0.23 (CHCl₃:MeOH:AcOH=8:1:1)
43) N-[(1S,2S)-1-(N,N-Dimethylcarbamoyl)-2-methylbutylcarbamoyl]-L-Leu-OH
mp: 185°-187° C. Rf: 0.27 (CHCl₃:MeOH:AcOH=8:1:1)

Preparation 21

To a solution of N-(1,2,3,6-tetrahydropyridin-1-ylcarbonyl)-L-Leu-OBzl (0.58 g) in MeOH (6 ml) was added 1N NaOH (3.5 ml) at room temperature. After one hour, the mixture was acidified with 1N HCl (5 ml) and the solvent was removed by evaporation in vacuo. The residue was dissolved in ethyl acetate (20 ml) and washed with water (20 ml) and brine (20 ml). The organic layer was dried over magnesium sulfate and concentrated in vacuo to give N-(1,2,3,6-tetrahydropyridin-1-ylcarbonyl)-L-Leu-OH (0.31 g) as an oil.
Rf: 0.42 (CHCl₃:MeOH:AcOH=16:1:1)

Preparation 22

The following compounds could be obtained by hydrolyzing the corresponding benzyl ester compounds with 1N NaOH in a similar manner to that of Preparation 21.

1) N-(Thiomorpholinocarbonyl)-L-Leu-OH
Rf: 0.31 (benzene:AcOEt:AcOH=20:20:1)
2) (2S)-2-[(1S,2S)-1-(Piperidinocarbonyl)-2-methylbutylcarbamoyloxy]-4-methylvaleric acid
Rf: 0.47 (CHCl₃:MeOH:AcOH=16:1:1)

Preparation 23

L-Leu-OH (10.0 g) was dissolved in water (150 ml) containing concentrated sulfuric acid (3.2 ml) at 0° C. To the solution was added dropwise a solution of sodium nitrate (7.9 g) in water (50 ml) over 1 hour. The mixture was saturated with sodium chloride and extracted with ethyl acetate (500 ml). The organic layer was dried over magnesium sulfate and concentrated in vacuo. The residual solid was triturated with hexane to give (2S)-2-hydroxy-4-methylvaleric acid (6.51 g).
mp: 70°-72° C. Rf: 0.80 (n-BuOH:AcOH:H₂O=4:1:1)

Preparation 24

To a stirring solution of (2S)-2-hydroxy-4-methylvaleric acid (5.0 g) and benzyl bromide (4.95 ml) in DMF (50 ml) was added potassium carbonate (3.13 g) at room temperature. After being stirred for 12 hours, the solvent was removed by evaporation in vacuo. The residue was dissolved in ethyl acetate (100 ml) and washed with water, 1N HCl and brine successively. The organic layer was dried over magnesium sulfate and concentrated in vacuo. The residual oil was purified with silica gel column chromatography (hexane-ethyl acetate as an eluent) to give benzyl (2S)-2-hydroxy-4-methylvalerate (8.2 g) as a colorless oil.

Rf: 0.67 (CHCl$_3$:MeOH:AcOH=16:1:1)

Preparation 25

To a solution of benzyl (2S)-2-hydroxy-4-methylvalerate (1.00 g) in tetrahydrofuran (20 ml) was added trichloromethyl chloroformate (0.55 ml) at room temperature. The solution was refluxed for 11 hours and the solvent was removed by evaporation at atmospheric pressure to give benzyl (2S)-2-chlorocarbonyloxy-4-methylvalerate (1.26 g) as an oil.

Rf: 0.81 (n-hexane:AcOEt=2:1)

Preparation 26

A solution of benzyl (2R)-2-t-butoxycarbonylmethyl-4-methylvalerate (3.40 g) in TFA (60 ml) was stirred for 1 hour under ice-bath cooling. Evaporation of TFA gave benzyl (2R)-2-carboxymethyl-4-methylvalerate (2.72 g) as an oil.

Rf: 0.73 (benzene:AcOEt:AcOH=20:20:1)

Preparation 27

The following compounds could be obtained by reacting the corresponding starting compounds with phenyl isocyanate in Et$_3$N or NMM in a similar manner to that of Preparation 7.

1) N-Cyclohexylcarbamoyl-L-Leu-OBzl
   mp: 120°–125° C. Rf: 0.73 (CHCl$_3$:MeOH=9:1)
2) N-Cyclohexylcarbamoyl-L-Leu-D-Trp(CH$_3$)-OBzl
   mp: 190°–193° C. Rf: 0.74 (CHCl$_3$:MeOH=9:1)

Preparation 28

The following compounds could be obtained by reacting TsOH.H-L-Leu-OBzl with the corresponding amines in the presence of trichloromethyl chloroformate in a similar manner to that of Example 72.

1) N-[1-(N,N-Dimethylaminocarbonylmethyl)cyclohexylcarbamoyl]-L-Leu-OBzl
   Rf: 0.70 (CHCl$_3$:MeOH=9:1)
2) N-[(1S,2S)-1-(N,N-Dimethylcarbamoyl-2-methylbutylcarbamoyl)-L-Leu-OBzl
   mp: 95°–98° C. Rf: 0.32 (n-hexane:AcOEt=1:1)
3) N-(Piperidinocarbamoyl)-L-Leu-OBzl
   Rf: 0.43 (n-hexane:AcOEt=1:1)
4) N-(2-Pyridylmethylcarbamoyl)-L-Leu-OBzl
   Rf: 0.50 (AcOEt)
5) N-[(2S)-2-Methylbutylcarbamoyl]-L-Leu-OBzl
   mp: 73°–75° C. Rf: 0.29 (n-hexane:AcOEt=3:1)

Preparation 29

1) A mixture of TSOH.H-L-Leu-OBzl (12.0 g), ethyl acetate (150 ml) and 1M sodium bicarbonate (150 ml) was stirred at room temperature for 20 minutes. The separated organic phase was washed with 1M sodium bicarbonate and a saturated aqueous sodium chloride, and then dried over magnesium sulfate. To this solution was added 4N hydrogen chloride in ethyl acetate (15.3 ml), followed by stirring for 5 minutes under ice-cooling. Removal of the solvent gave HCl.H-L-Leu-OBzl (7.66 g).

2) To a solution of the above product (7.6 g) in toluene (228 ml) were added charcoal (380 mg) and a solution of trichloromethyl chloroformate (3.6 ml) in toluene (7.6 ml), and the mixture was stirred at 120° C. for 2 hours and then filtered. The solvent was removed from the filtrate and the residue was dissolved in toluene (152 ml). This solution was evaporated to give (S)-α-benzyloxycarbonyl-γ-methylbutylisocyanate (7.58 g).

3) To a solution of this product in ethyl acetate (114 ml) was added hexahydro-1H-azepin (3.5 g) under ice-cooling, and the mixture was stirred at the same temperature for 30 minute. The resultant solution was washed with 5% HCl, aqueous sodium bicarbonate and saturated aqueous sodium chloride and then dried over magnesium sulfate. Removal of the solvent gave N-(hexahydro-1H-azepin-1-ylcarbonyl)-L-Leu-OBzl (9.96 g).

Rf: 0.71 (n-hexane:EtOAc=2:1)

4) To a solution of N-(hexahydro-1H-azepin-1-ylcarbonyl)-L-Leu-OBzl (9.0 g) in ethanol (69 ml) was catalytically reduced with 10% palladium on carbon (0.692 g) under 3 atmospheric pressure of hydrogen for 30 minutes. The catalyst was removed by filtration and the filtrate was evaporated to dryness. The residue was dissolved in ethyl acetate (138 ml), and this solution was washed with 5% HCl and saturated aqueous sodium chloride and then dried. Removal of the solvent gave a residue, which was crystallized from ethyl acetate and hexane to afford N-(hexahydro-1H-azepin-1-ylcarbonyl)-L-Leu-OH (5.7 g).

mp: 90°–92° C. Rf: 0.43 (benzene:EtOAc:AcOH=20:20:1)

Preparation 30

1) To a solution of Boc-D-Trp-OH (15.0 g) in DMF (150 ml) were added potassium tert-butoxide (13.8 g) and methyl iodide (10.5 g) under ice-cooling. After stirring under ice-cooling for 30 minutes and at room temperature for 15 minutes, the reaction mixture was poured into ice-cooled 0.24 NHCl, followed by extraction with ethyl acetate. The extract was washed with 5% NaHSO$_3$ and saturated aqueous sodium chloride. Removal of the solvent gave a residue, which was crystallized from diisopropyl ether to afford Boc-D-Trp(CH$_3$)-OH (9.18 g).

Rf: 0.61 (CHCl$_3$:MeOH=8:2)

2) To a solution of this product (6.84 g) in dichloromethane (137 ml) were added NMM (2.17 g) and isobutyl chloroformate (2.93 g) at −30° C. Thereto was added 2HCl.H-D-Pya-OC$_2$H$_5$ (6.0 g) at −15° to −10° C. and then NMM (4.54 g) at −20° C., and the mixture was stirred at the same temperature for 30 minutes. The reaction mixture was washed with 1M sodium bicarbonate and saturated aqueous sodium chloride, and then treated with charcoal. The solvent was removed by evaporation and the residue was crystallized from ethyl acetate and hexane to give Boc-D-Trp(CH$_3$)-D-Pya-OC$_2$H$_5$ (7.88 g).

mp: 99°–101° C. Rf: 0.80 (CHCl$_3$:MeOH=9:1) $[\alpha]_D^{23}$: +26.5° (C=1.0, MeOH)

3) To a solution of the above product (7.8 g) in ethyl acetate (61.7 ml) was added 4N hydrogen chloride in ethyl acetate (30.8 ml) under ice-cooling, and this mixture was stirred at room temperature for an hour. The desired product was collected by decantation and triturated with ethyl acetate to give 2HCl.H-D-Trp(CH$_3$)-D-Pya-OC$_2$H$_5$ (7.4 g).

Preparation 31-1)

N$^\alpha$-Boc-N$^\alpha$-methyl-N$^{in}$-methyl-D-Trp-OH (0.65 g), 2HCl.H-D-Pya-OEt (0.52 g) HOBt (0.32 g), WSCD (0.36 g), Et$_3$N (0.20 g) and DMF (20 ml) were reacted in a similar manner to that of Preparation 1-1) to give N$^\alpha$-Boc-N$^\alpha$-methyl-N$^{in}$-methyl-D-Trp-D-Pya-OEt (0.78 g).

Rf=0.81 (CHCl$_3$:MeOH=9:1)

Preparation 31-2)

Boc-D-Trp(CHO)-OH (2.0 g), 2HCl.H-D-Pya-OEt (1.61 g), WSCD (1.03 g), HOBt (0.90 g), NMM (0.61 g) and DMF (20 ml) were reacted in a similar manner to that of Preparation 1-1) to give Boc-D-Trp(CHO)-D-Pya-OEt (2.23 g).

mp: 136°–137° C. Rf: 0.65 (ethyl acetate)

Preparation 31-3)

To a solution of Boc-D-Trp(CHO)-OH (0.79 g) and N-methylmorpholine (0.13 ml) in methylene chloride (20 ml) was added dropwise isobutyl chloroformate (0.31 ml) at −15° C. After 15 minutes, N-methylmorpholine (0.13 ml) and HCl.H-D-Glu(OBzl)-OPac (0.85 g) were added to this solution at −30° C. After being stirred for 1 hour, the mixture was washed with 0.5N hydrochloric acid (10 ml), water (10 ml) and 1M sodium hydrogen carbonate (10 ml), dried over magnesium sulfate and concentrated in vacuo. The residual solid was triturated with ethyl ether to give Boc-D-Trp(CHO)-D-Glu(OBzl)-OPac (1.31 g).

mp: 142°–144° C. Rf: 0.79 (chloroform:methanol=9:1)

Preparation 31-4)

Boc-D-Trp(CHO)-D-Phe-OPac was obtained in a similar manner to that of Preparation 1-1).

mp: 142°–146° C. Rf: 0.78 (chloroform:methanol=9:1)

Preparation 31-5)

Boc-D-Trp(CHO)-OH (1.0 g), HCl.H-βAla-OPac (0.81 g), HOBT (0.49 g), WSCD (0.56 g) and DMF (10 ml) were reacted in a similar manner to that of Preparation 1-1) to give Boc-D-Trp(CHO)-βAla-OPac (3.15 g).

mp: 153°–155° C. Rf: 0.58 (chloroform:methanol=9:1)

Preparation 31-6)

Boc-D-Trp(CHO)-OH (10.0 g), HCl.H-βAla-OMe (4.41 g) HOBt (4.47 g), WSCD (5.14 g) and DMF (100 ml) were reacted in a similar manner to that of Preparation 1-1) to give Boc-D-Trp(CHO)-βAla-OMe (8.77 g).
mp: 134°–135° C. Rf: 0.54 (CHCl$_3$:MeOH=9:1)

Preparation 31-7)

Boc-D-Phe-OH (265 mg), 2HCl.H-D-Pya-OEt (267 mg), HOBt (0.16 g) WSCD (0.19 g), N-methylmorpholine (0.10 g) and DMF (6 ml) were reacted in a similar manner to that of Preparation 1-1) to give Boc-D-Phe-D-Pya-OEt (0.32 g).

mp: 97°–99° C. Rf: 0.58 (CHCl$_3$:MeOH=9:1)

The following compounds could be obtained by removing t-butoxycarbonyl groups from the corresponding starting compounds in a similar manner to that of Preparation 1-2).

Preparation 32-1)

HCl.H-D-Trp(Me)-D-Leu-OBzl
mp: 85°–90° C. Rf: 0.27 (CHCl$_3$:MeOH=9:1)

Preparation 32-2)

2HCl.N$^\alpha$-methyl-D-Trp(Me)-D-Pya-OEt
mp: 100°–110° C. Rf: 0.50 (CHCl$_3$:MeOH=9:1)

Preparation 32-3)

2HCl.H-D-Trp(CHO)-D-Pya-OEt Rf: 0.16 (CHCl$_3$:MeOH:AcOH=8:1:1, V/V)

Preparation 32-4)

HCl.H-D-Trp(CHO)-D-Glu(OBzl)-OPac
mp: 80°–89° C. Rf=0.50 (chloroform:methanol=9:1)

Preparation 32-5)

HCl.H-D-Trp(CHO)-D-Phe-OPac
mp: 185° C. (dec.) Rf: 0.37 (chloroform:methanol:acetic acid=16:1:1)

Preparation 32-6)

HCl.H-D-Trp(CHO)-βAla-OPac
mp: 157°–164° C. Rf: 0.17 (chloroform:methanol:acetic acid=16:1:1)

Preparation 32-7)

HCl.H-D-Trp(CHO)-βAla-OMe
mp: 168°–169° C. Rf: 0.53 (10% MeOH in CHCl$_3$)

Preparation 32-8)

2HCl.H-D-Phe-D-Pya-OEt
Rf: 0.12 (10% MeOH in CHCl$_3$)

The following compounds could be obtained by reacting (S)-α-benzyloxycarbonyl-γ-methylbutylisocyanate with the corresponding amines in a similar manner to that of Preparation 7.

Preparation 33-1)

N-(Pyrrolidin-1-ylcarbonyl)-L-Leu-OBzl
Rf: 0.14 (EtOAc:hexane=1:2)

Preparation 33-2)

N-(Piperidin-1-ylcarbonyl)-L-Leu-OBzl
mp: 75°–76° C. Rf: 0.27 (EtOAc:hexane=1:2)

Preparation 33-3)

N-[(2S)-4-Methyl-2-(1-methylpropyl)-3-oxopiperidin-1-ylcarbonyl]-L-Leu-OBzl
Rf: 0.13 (EtOAc:hexane=1:1, V/V)

Preparation 33-4)

N-[{(1S)-1-(N,N-Dimethylcarbamoyl)-1-cyclohexylmethyl}carbamoyl]-L-Leu-OBzl
Rf: 0.26 (EtOAc:hexane=1:1, V/V)

Preparation 33-5)

N-[{(1S)-1-(N,N-Dimethylcarbamoyl)-1-phenylmethyl}carbamoyl]-L-Leu-OBzl
Rf: 0.08 (EtOAc:hexane=1:2, V/V)

Preparation 33-6)

N-[{cis-4-(N,N-Dimethylcarbamoylmethyl)cyclohexyl}carbamoyl]-L-Leu-OBzl
Rf: 0.25 (ethyl acetate)

Preparation 33-7)

N-[{cis-4-(N,N-Dimethylcarbamoyl)cyclohexyl}carbamoyl]-L-Leu-OBzl
Rf: 0.34 (ethyl acetate)

Preparation 33-8)

N-(N,N-Dimethylcarbamoylmethyl)carbamoyl-L-Leu-OBzl
Rf: 0.23 (ethyl acetate)

Preparation 33-9)

N-[{2-(N,N-Dimethylcarbamoyl)ethyl}carbamoyl]-L-Leu-OBzl
Rf: 0.33 (ethyl acetate)

Preparation 33-10)

N-[(trans-4-Hydroxycyclohexyl)carbamoyl]-L-Leu-OBzl
mp: 169°–171° C. Rf: 0.53 (ethyl acetate)

Preparation 33-11)

N-[{(1S)-1-(Hydroxymethyl)-3-methylbutyl}carbamoyl]-L-Leu-OBzl
Rf: 0.38 (n-hexane:ethyl acetate=1:1)

Preparation 33-12

N-[{2-(Morpholino)ethyl}carbamoyl]-L-Leu-OBzl
Rf: 0.46 (CHCl$_3$:MeOH:AcOH=8:2:1)

Preparation 33-13)

N-(ε-Caprolactam-3-ylcarbamoyl)-L-Leu-OBzl
mp: 148°–150° C. Rf=0.52 (ethyl acetate)

Preparation 33-14)

N-(N'-Isobutyrylhydrazinocarbonyl)-L-Leu-OBzl
mp: 93°–96° C. Rf: 0.16 (n-hexane:ethyl acetate=1:1)

Preparation 33-15)

N-[(1-Ethoxycarbonylpiperidin-4-yl)carbamoyl]-L-Leu-OBzl
Rf: 0.35 (n-hexane:ethylacetate=1:1)

The following compounds were obtained by removing benzyl groups from the corresponding starting compounds in a similar manner to that of Preparation 1-4).

Preparation 34-1)
N-(Pyrrolidin-1-ylcarbonyl)-L-Leu-OH
Rf: 0.18 (10% MeOH in CHCl₃)

Preparation 34-2)
N-(Piperidinocarbonyl)-L-Leu-OH
Rf: 0.17 (10% MeOH in CHCl₃)

Preparation 34-3)
N-(2-Chlorophenylcarbamoyl)-L-Leu-OH
Rf: 0.20 (10% MeOH in CHCl₃)

Preparation 34-4)
N-(o-Chlorophenylacetyl)-L-Leu-OH
mp: 145°–146° C. Rf: 0.21 (10% MeOH in CHCl₃)

Preparation 34-5)
(2R)-2-[{(1S)-1-(N,N-Dimethylcarbamoyl)-2,2-dimethylpropyl}carbamoyl]methyl-4-methylvaleric acid
Rf: 0.43 (10% MeOH in CHCl₃)

Preparation 34-6)
N-[(2S)-4-Methyl-2-(1-methylpropyl)-3-oxopiperazin-1-ylcarbonyl]-L-Leu-OH
mp: 180° C. (dec.) Rf: 0.20 (10% MeOH in CHCl₃)

Preparation 34-7)
N-[{(1S)-1-(N,N-Dimethylcarbamoyl)-1-cyclohexylmethyl}carbamoyl]-L-Leu-OH
mp: 210°–211° C. Rf: 0.20 (10% MeOH in CHCl₃)

Preparation 34-8)
N-[{(1S)-1-(N,N-Dimethylcarbamoyl)-1-phenylmethyl}carbamoyl]-L-Leu-OH
Rf: 0.38 (CHCl₃:MeOH:AcOH=16:1:1, V/V)

Preparation 34-9)
N-(Hexahydro-1H-azepin-1-ylcarbonyl)-N-methyl-Leu-OH
Rf: 0.58 (benzene:ethyl acetate:acetic acid=20:20:1, V/V)

Preparation 34-10)
N-[{cis-4-(N,N-Dimethylcarbamoylmethyl)cyclohexyl}carbamoyl]-L-Leu-OH
Rf: 0.57 (CHCl₃:MeOH:AcOH=8:1:1)

Preparation 34-11)
N-[{cis-4-(N,N-Dimethylcarbamoyl)cyclohexyl}carbamoyl]-L-Leu-OH
Rf: 0.52 (CHCl₃:MeOH:AcOH=8:1:1)

Preparation 34-12)
N-(N,N-Dimethylcarbamoylmethyl)carbamoyl-L-Leu-OH
Rf: 0.73 (CHCl₃:MeOH:AcOH=8:2:1)

Preparation 34-13)
N-[{2-(N,N-Dimethylcarbamoyl)ethyl}carbamoyl]-L-Leu-OH
Rf: 0.77 (CHCl₃:MeOH:AcOH=8:2:1)

Preparation 34-14)
N-[(trans-4-Hydroxycyclohexyl)carbamoyl]-L-Leu-OH
Rf: 0.78 (CHCl₃:MeOH:AcOH=8:1:1)

Preparation 34-15)
N-[N-(2-Hydroxyethyl)-N-methylcarbamoyl]-L-Leu-OH
Rf: 0.65 (CHCl₃:MeOH:AcOH=8:1:1)

Preparation 34-16)
N-[{(1S)-(1-Hydroxymethyl)-3-methylbutyl}carbamoyl]-L-Leu-OH
Rf: 0.38 (benzene:ethyl acetate:acetic acid=20:20:1)

Preparation 34-17)
N-[{2-(Morpholino)ethyl}carbamoyl]-L-Leu-OH
Rf: 0.21 (CHCl₃:MeOH:AcOH=8:2:1)

Preparation 34-18)
N-(ε-Caprolactam-3-ylcarbamoyl)-L-Leu-OH
Rf: 0.67 (CHCl₃:MeOH:AcOH=8:2:1)

Preparation 34-19)
N-(N'-Isobutyrylhydrazinocarbonyl)-L-Leu-OH
Rf: 0.45 (CHCl₃:MeOH:AcOH=8:1:1)

Preparation 34-20)
N-[(1-ethoxycarbonylpiperidin-4-yl)-carbamoyl]-L-Leu-OH
Rf: 0.48 (CHCl₃:MeOH:AcOH=8:1:1)

Preparation 35
Hexahydro-1H-azepine (0.3 g), (S)-α-benzyloxycarbonyl-γ,γ-dimethylbutylisocyanate (0.48 g) and EtOAc (10 ml) were reacted in a similar manner to that of Preparation 7 to give N-(hexahydro-1H-azepin-1-ylcarbonyl)-γ-methyl-L-Leu-OBzl. This product, 10% pd-C (60 mg), MeOH (10 ml) and H₂O (1 ml) were reacted in a similar manner to that of Preparation 1-4) to give N-(hexahydro-1H-azepin-1-ylcarbonyl)-γ-methyl-L-Leu-OH (0.43 g).
mp: 64°–66° C. Rf: 0.20 (10% MeOH in CHCl₃)

Preparation 36-1)
Boc-D-1-Nal-OH (0.50 g), methanesulfonamide (0.18 g) DMAP (0.23 g), WSCD.HCl (0.37 g) and CH₂Cl₂ (10 ml) were reacted in a similar manner to that of Preparation 1-1) to give Boc-D-1-Nal-methanesulfonamide (0.63 g).
Rf: 0.48 (10% MeOH in CHCl₃)

Preparation 36-2)
Boc-D-Phe-OH (0.20 g), methanesulfonamide (79 mg) DMAP (0.11 g), WSCD.HCl (0.17 g) and DMF (4 ml) were reacted in a similar manner to that of Preparation 1-1) to give Boc-D-Phe-methanesulfonamide (0.21 g).
mp: 73°–75° C. Rf: 0.80 (CHCl₃:MeOH:AcOH=8:1:1, V/V)

Preparation 36-3)
Boc-D-Phe-OH (0.20 g), benzenesulfonamide (0.13 g), DMAP (0.11 g) WSCD.HCl (0.17 g) and CH₂Cl₂ (4 ml) were reacted in a similar manner to that of Preparation 1-1) to give Boc-D-Phe-benzenesulfonamide (0.32 g).
Rf: 0.83 (CHCl₃:MeOH:AcOH=8:1:1, V/V)

Preparation 36-4)
Boc-D-Pya-OH (0.20 g), diethylamine (66 mg), HOBt (0.12 g), WSCD.HCl (0.17 g) and DMF (2 ml) were reacted in a similar manner to that of Preparation 1-1) to give Boc-D-Pya-diethylamide (45 mg).
mp: 133°–135° C. Rf: 0.32 (EtOAc)

Preparation 37-1)
Boc-D-1-Nal-methanesulfonamide (0.60 g), 4N HCl-EtOAc (10 ml) and EtOAc (3 ml) were reacted in a similar manner to that of Preparation 1-2) to give HCl.H-D-1-Nal-methanesulfonamide.
mp: 250° C. (dec.) Rf: 0.42 (CHCl₃:MeOH:AcOH=8:2:1, V/V)

Preparation 37-2)
Boc-D-Phe-methanesulfonamide (0.19 g) and 4N HCl-EtOAc (10 ml) were reacted in a similar manner to that of Preparation 1-2) to give HCl.H-D-Phe-methanesulfonamide (0.13 g).
mp: 243° C. (dec.) Rf: 0.12 (CHCl₃:MeOH:AcOH=8:1:1, V/V)

Preparation 37-3)
Boc-D-Phe-benzenesulfonamide (0.30 g) and 4N HCl-EtOAc (10 ml) were reacted in a similar manner to that of Preparation 1-2) to give HCl.H-D-Phe-benzenesulfonamide (0.22 g).

Rf: 0.22 (CHCl₃:MeOH:AcOH=8:1:1, V/V) mp: 230° C. (dec.)

Preparation 37-4)

Boc-D-Pya-diethylamide (45 mg) and 4N HCl-EtOAc (1 ml) were reacted in a similar manner to that of Preparation 1-2) to give 2HCl.H-D-Pya-diethylamide (41 mg).

Rf: 0.18 (10% MeOH in CHCl₃)

Preparation 38-1)

o-Chlorophenylisocyanate (1.54 g), TosOH.H-L-Leu-OBzl (3.94 g) N-methylmorpholine (1.1 g) and EtOAc (50 ml) were reacted in a similar manner to that of Preparation 7 to give N-(2-chlorophenylcarbamoyl)-L-Leu-OBzl (4.30 g).

Rf: 0.86 (10% MeOH in CHCl₃)

Preparation 38-2)

o-Chlorophenylacetic acid (0.73 g), HCl.H-L-Leu-OBzl (1.0 g), WSCD (0.66 g) and CH₂Cl₂ (20 ml) were reacted in a similar manner to that of Preparation 1-1) to give N-(o-chlorophenylacetyl)-L-Leu-OBzl (1.4 g).

mp : 75°-77° C. Rf: 0.86 (10% MeOH in CHCl₃)

Preparation 39

To a stirring solution of N-Boc-N-methyl-glycinal (2.0 g) and HCl.H-L-Ile-OMe (2.0 g) in MeOH was added sodium cyanoborohydride (0.87 g) at room temperature. After 30 minutes, the solvent was evaporated in vacuo and the residue was dissolved in ethyl acetate (50 ml) and washed with sodium hydrogen carbonate. The organic layer was dried over magnesium sulfate and concentrated in vacuo. The residue was purified by a silica gel column chromatography (40 g, ethyl acetate:hexane=1:3~3:1 as an eluent) to give N-[2-(N-Boc-N-methylamino)ethyl]-L-Ile-OMe (1.67 g).

Rf: 0.78 (EtOAc:hexane=2:1, V/V)

Preparation 40

N-[2-(N-Boc-N-methylamino)ethyl]-L-Ile-OMe (1.60 g) and 4N HCl-EtOAc (20 ml) were reacted in a similar manner to that of Preparation 1-2) to give 2HCl.N-[2-(N-methylamino)ethyl]-L-Ile-OMe (1.40 g).

mp: 148°-150° C. Rf: 0.19 (10% MeOH in CHCl₃)

Preparation 41

2HCl.N-[2-(N-methylamino)ethyl]-L-Ile-OMe (1.30 g) was dissolved in 24N NH₃-MeOH (20 ml) at room temperature and the solution was allowed to stand for 5 days. The solvent was evaporated in vacuo and the residue was dissolved in EtOAc (30 ml) and washed with sodium hydrogen carbonate (20 ml). The organic layer was dried over magnesium sulfate and concentrated in vacuo to give (3S)-1-methyl-3-(1-methylpropyl)-2-oxopiperazine (0.69 g).

Rf: 0.57 (10% MeOH in CHCl₃)

Preparation 42

To a stirring suspension of $N^\alpha$-Boc-$N^{in}$-methyl-D-Trp-OH (1.0 g) and NaH (0.31 g, 60% in oil) in tetrahydrofuran was added methyl iodide (1.34 g) at room temperature. After eight days, the mixture was evaporated in vacuo and the residue was suspended in EtOAc (30 ml) and washed with 1N HCl and brine. The organic layer was dried over magnesium sulfate and concentrated in vacuo. The residue was purified by silica gel column chromatography (20 g, 2% MeOH in CHCl₃ as an eluent) to give $N^\alpha$-Boc-$N^\alpha$-methyl-$N^{in}$-methyl-D-Trp-OH (0.70 g).

Rf: 0.42 (10% MeOH in CHCl₃)

Preparation 43

Finely powdered potassium carbonate (5.8 g) was suspended in a solution of 2-(aminomethyl)pyridine (3.0 g) and ethyl bromoacetate (3.1 ml) in dimethylformamide (30 ml). The mixture was stirred at room temperature overnight, then poured into ice water. The mixture was extracted with ethyl acetate (50 ml×2) and the organic layer was washed with saturated sodium chloride solution (2 times), dried over magnesium sulfate, and evaporated in vacuo. The residue was purified with a silica gel column chromatography (MeOH:CHCl₃=1:99 as an eluent) to give N-(ethoxycarbonylmethyl)-N-(pyridin-2-ylmethyl)amine (2.30 g).

Rf: 0.27 (MeOH:CHCl₃=1:19)

Preparation 44

A solution of 2-[2-(t-butoxycarbonylamino)ethyl]-pyridine (2 g) in dimethylformamide (10 ml) was added to a suspension of sodium hydride (0.54 g) in dimethylformamide (10 ml) at 0° C. The mixture was stirred at 0° C. for 1 hour and at room temperature for 1 hour. Then a solution of ethyl bromoacetate (1.5 ml) in dimethylformamide (5 ml) was added thereto, and the mixture was stirred at room temperature for 2 hours. The solution was poured into saturated ammonium chloride (50 ml) and the mixture was extracted with ethyl acetate (30 ml×2). The combined organic layer was washed with saturated sodium chloride solution, dried over magnesium sulfate, and evaporated in vacuo. The residue was purified with silica gel column chromatography (MeOH:CHCl₃=1:99 as an eluent) to give 2-[2-{N-(t-butoxycarbonyl)-N-(ethoxycarbonylmethyl)amino}ethyl]pyridine.

Rf: 0.47 (CHCl₃:MeOH=1:19)

Preparation 45

2-[2-{N-(t-Butoxycarbonyl)-N-(ethoxycarbonylmethyl)amino}ethyl]pyridine (439 mg) and 4NHCl-1,4-dioxane (5 ml) were reacted in a similar manner to that of Preparation 1-2) to give N-(ethoxycarbonylmethyl)-N-[2-(pyridin-2-yl)ethyl]amine dihydrochloride (400 mg).

Rf: 0.24 (MeOH:CHCl₃=1:19)

Preparation 46

N-Methyl-L-Leu-OBzl hydrochloride (600 mg), trichloromethyl chloroformate (0.54 ml), and hexamethyleneimine (877 mg) were reacted in a similar manner to those of Preparations 29-2) and 29-3) to give N-(hexahydro-1H-azepin-1-ylcarbonyl)-N-methyl-L-Leu-OBzl (515 mg).

Rf: 0.44 (n-hexane:ethyl acetate=3:1)

Preparation 47

Boc-L-Asp(OBzl)-OH (1.0 g), 2-aminopyridine (0.35 g), HOBT (0.50 g), WSCD (0.71 g) and DMF (20 ml) were reacted in a similar manner to that of Preparation 1-1) to give Boc-L-Asp(OBzl)-2-pyridylamide.

Rf: 0.52 (CHCl₃:MeOH:AcOH=16:1:1)

Preparation 48

H-L-Asp(OBzl)-2-pyridylamide.2HCl was obtained in a similar manner to that of Preparation 1-2).

mp: 170°-178° C. Rf: 0.23 (chloroform:methanol:acetic acid=8:1:1)

Preparation 49

HCl.H-L-tert-Leu dimethylamide (0.22 g), benzyl (2R)-2-(carboxymethyl)-4-methylvalerate (0.30 g), WSCD (0.21 g) and CH₂Cl₂ (8 ml) were reacted in a similar manner to that of Preparation 1-1) to give benzyl (2R)-2-[{(1S)-1-(N,N-dimethylcarbamoyl)-2,2-dimethylpropyl}carbamoyl]methyl-4-methylvalerate (0.40 g).

Rf: 0.71 (10% MeOH in CHCl₃)

Preparation 50

N-[N-{(1S)-1-Dimethylcarbamoyl-2-methylpropyl}carbamoyl]-L-leucine was obtained from L-valine dimethylamide hydrochloride and (S)-α-benzyloxycarbonyl-γ-methylbutyl isocyanate in substantially the same manner as those of Preparations 7 and 1-4).

Rf: 0.25 (benzene:AcOEt:AcOH=20:20:1, v/v)

Preparation 51

N-[N-(2-Hydroxyethyl-N-methylcarbamoyl)]-L-Leu-OBzl was obtained in substantialy the same manner as that of Preparation 7.

Rf: 0.44 (AcoEt)

Preparation 52

Boc-D-alloIle-L-Leu-D-Trp(CHO)-OH was obtained in substantially the same manner as that of Example 172.

mp : 91°–113° C. Rf: 0.52 (chloroform:methanol:acetic acid=16:1:1)

Preparation 53-1)

N-(Hexahydro-1H-azepin-1-ylcarbonyl)-L-Leu-D-Trp(CH$_3$)-OBzl was obtained in substantially the same manner as that of Preparation 1-1).

mp: 107°–109° C. Rf: 0.80 (ethyl acetate)

Preparation 53-2)

N-(Hexahydro-1H-azepin-1-ylcarbonyl)-L-Leu-D-Trp(CH$_3$)-OH was obtained in substantially the same manner as that of Preparation 1-4).

Rf: 0.33 (benzene:ethyl acetate:acetic acid=20:20:1, v/v)

Preparation 54-1)

Boc-D-alloIle-L-Leu-D-Trp(CHO)-OPac was obtained in substantially the same manner as that of Preparation 1-1).

Rf: 0.76 (chloroform:methanol=9:1)

Preparation 54-2)

N-[2-(t-butoxycarbonylamino)ethyl]-L-Glu(OBzl)OEt was obtained in substantialy the same manner as that of Preparation 39.

Rf: 0.39 (AcOEt:n-hexane=3:2)

Preparation 54-3)

Ethyl (5S)-1-[2-(t-butoxycarbonylamino)ethyl]-2-pyrrolidone-5-carboxylate was obtained from N-[2-(t-butoxycarbonylamino)ethyl]-L-Glu(OBzl)OEt in substantially the same manner as those of Preparations 1-4) and 1-1).

Rf: 0.57 (MeOH:CHCl$_3$=1:10)

Preparation 54-4)

Ethyl (5S)-1-(2-aminoethyl)-2-pyrrolidone-5-carboxylate hydrochloride was obtained in substantially the same manner as that of Preparation 1-2).

mp : 72°–80° C. Rf: 0.31 (CHCl$_3$:MeOH:AcOH=8:2:1)

EXAMPLE 1-1

To a mixture of N-phenylacetyl-L-Leu-OH (0.25 g), HCl.H-D-Trp(CH$_3$)-D-Phe-OCH$_3$ (0.48 g) and HOBT (0.16 g) in DMF (8 ml) was added WSCD (0.19 g) under ice-bath cooling. After being stirred for 4.5 hours at the same temperature, the mixture was concentrated in vacuo and the residue was dissolved in ethyl acetate (50 ml). The solution was washed with 0.5N HCl (10 ml), saturated aqueous sodium bicarbonate (10 ml), and brine (10 ml) successively, dried over magnesium sulfate and concentrated in vacuo. The residue was triturated with ether to give the object compound (0.90 g).

mp: 185°–188° C. Rf: 0.52 (CHCl$_3$:MeOH=9:1)

EXAMPLE 1-2

To a solution of N-phenylacetyl-L-Leu-D-Trp(CH$_3$)-D-Phe-OCH$_3$ (0.85 g) in DMF (7 ml) was added 1N NaOH (1.5 ml) at 0° C. After being stirred for 20 minutes at the same temperature, the mixture was acidified with 1N HCl (2 ml) and concentrated in vacuo. The residue was dissolved in ethyl acetate (20 ml) and the solution was washed with 0.5N HCl (10 ml) and brine (10 ml). The organic layer was dried over magnesium sulfate and concentrated in vacuo. The residue was triturated with ether to give the object compound (0.50 g).

mp: 177°–185° C. FAB-MS m/z: 598 [M+H]$^+$ Rf: 0.52 (CHCl$_3$:MeOH:AcOH=16:1:1)

EXAMPLE 2-1

3-Phenylpropionic acid (33 mg), HCl.H-L-Leu-D-Trp(CH$_3$)-D-Phe-OBzl (0.12 g), HOBT (32 mg) and WSCD (37 mg) in DMF (2 ml) were reacted in a similar manner to that of Example 1-1) to give the object compound (0.13 g).

mp: 218°–220° C. Rf: 0.74 (CHCl$_3$:MeOH=9:1)

EXAMPLE 2-2

N-(3-Phenylpropionyl)-L-Leu-D-Trp(CH$_3$)-D-Phe-OBzl (0.1 g) in DMF (1.5 ml) was hydrolyzed with 1N NaOH (0.5 ml) in a similar manner to that of Example 1-2) to give the object compound (68 mg).

mp: 175°–180° C. Rf: 0.51 (CHCl$_3$:MeOH:AcOH=16:1:1) FAB-MS m/z: 611 [M+H]$^+$

EXAMPLE 3-1

Cyclohexylacetic acid (31 mg), HCl.H-L-Leu-D-Trp(CH$_3$)-D-Phe-OBzl (0.12 g), HOBT (32 mg) and WSCD (37 mg) in DMF (2 ml) was reacted in a similar manner to that of Example 1-1) to give the object compound (0.12 g).

mp: 191°–194° C. Rf: 0.74 (CHCl$_3$:MeOH=9:1)

EXAMPLE 3-2

N-Cyclohexylacetyl-L-Leu-D-Trp(CH$_3$)-D-Phe-OC$_2$H$_5$ (0.1 g) was reacted with 1N NaOH (0.5 ml) in DMF (1.5 ml) in a similar manner to that of Example 1-2) to give the object compound (63 mg).

mp: 225°–228° C. Rf: 0.51 (CHCl$_3$:MeOH:AcOH=16:1:1) FAB-MS m/z: 603 [M+H]$^+$

EXAMPLE 4-1

To a solution of HCl.H-L-Leu-D-Trp(CH$_3$)-D-Phe-OBzl (120 mg) and Et$_3$N (22 mg) in DMF (5 ml) was added phenyl isocyanate (26 mg) at room temperature. The mixture was stirred at the same temperature for 30 minutes. After evaporation of the solvent, the residue was dissolved in AcOEt (20 ml) and the solution was washed with 5% HCl, 1M aqueous sodium bicarbonate and saturated aqueous sodium chloride solution successively, dried over anhydrous magnesium sulfate, and concentrated under reduced pressure. The residue was crystallized from ether to give the object compound (115 mg).

mp: 222°–224° C. Rf: 0.77 (CHCl$_3$:MeOH=9:1)

EXAMPLE 4-2

N-Phenylcarbamoyl-L-Leu-D-Trp(CH$_3$)-D-Phe-OBzl (115 mg) in DMF (2 ml) was hydrolyzed with 1N NaOH (0.3 ml) in a similar manner to that of Example 1-2) to give the object compound (93 mg).

mp: 248°–251° C. Rf: 0.60 (CHCl$_3$:MeOH:AcOH=16:1:1)

EXAMPLE 5-1

HCl.H-L-Leu-D-Trp(CH$_3$)-D-Phe-OBzl (300 mg), Et$_3$N (50.2 mg) and cyclohexyl isocyanate (68.2 mg) in DMF (10 ml) was reacted at room temperature for 30 minutes in a similar manner to that of Example 4-1) to give the object compound (325 mg).

mp: 218°–220° C. Rf: 0.67 (CHCl$_3$:MeOH=9:1)

EXAMPLE 5-2

N-Cyclohexylcarbamoyl-L-Leu-D-Trp(CH$_3$)-D-Phe-OBzl (300 mg) in DMF (10 ml) was hydrolyzed with 1N NaOH (2.2 ml) at room temperature for 30 minutes in a similar manner to that of Example 1-2) to give the object compound (246 mg).

mp: 219°–221° C. Rf: 0.52 (CHCl$_3$:MeOH:AcOH=16:1:1)

EXAMPLE 6-1

N-Phenylacetyl-L-Leu-D-Trp(CH$_3$)-OH (0.20 g), HOBT (72 mg), WSCD (83 mg) and NMM (54 mg) were reacted in a similar manner to that of Preparation 3-3) to give the object compound (0.21 g).

mp: 130°–137° C. Rf: 0.51 (CHCl$_3$:MeOH=9:1) FAB-MS m/z: 626 [M+H]+

EXAMPLE 6-2

N-Phenylacetyl-L-Leu-D-Trp(CH$_3$)-D-Pya-OC$_2$H$_5$.HCl (0.15 g) in DMF (2 ml) was reacted with 1N-NaOH (1 ml) at 0° C. for 20 minutes in a similar manner to that of Example 1-2) to give the object compound (102 mg).

mp: 205° C. (dec.) Rf: 0.33 (CHCl$_3$:MeOH:AcOH=8:1:1) FAB-MS m/z: 598 [M+H]+

EXAMPLE 7-1

2HCl.H-L-Leu-D-Trp(CH$_3$)-D-Pya-OC$_2$H$_5$ (350 mg), Et$_3$N (122 mg) and cyclohexylisocyanate (91 mg) in DMF (10 ml) was reacted at room temperature for 30 minutes in a similar manner to that of Example 4-1) to give the object compound (284 mg).

mp: 216°–218° C. Rf: 0.61 (CHCl$_3$:MeOH=9:1)

EXAMPLE 7-2

N-Cyclohexylcarbamoyl-L-Leu-D-Trp(CH$_3$)-D-Pya-OC$_2$H$_5$ (230 mg) in MeOH (10 ml) was reacted with 1N NaOH (1.6 ml) at room temperature for 1 hour in a similar manner to that of Example 1-2) to give the object compound (125 mg).

mp: 207°–210° C. Rf: 0.45 (CHCl$_3$:MeOH:AcOH=8:1:1)

EXAMPLE 8-1

N-Phenylacetyl-L-Leu-D-Trp(CH$_3$)-OH (90 mg), HCl.H-L-Phe-OEt (46 mg), WSCD (33 mg) and HOBT (27 mg) in DMF (2 ml) was reacted at 5° C. overnight in a similar manner to that of Example 1-1) to give the object compound (87 mg).

mp: 207°–209° C. Rf: 0.38 (CHCl$_3$:AcOEt=3:1)

EXAMPLE 8-2

N-Phenylacetyl-L-Leu-D-Trp(CH$_3$)-L-Phe-OEt (64 mg) in DMSO (2 ml) was reacted with 1N NaOH (0.2 ml) at room temperature for 2 hours in a similar manner to that of Example 1-2) to give the object compound (48 mg).

mp: 172°–175° C. Rf: 0.30 (CHCl$_3$:MeOH=5:1)

EXAMPLE 9

To a solution of N-cyclohexylcarbamoyl-L-Leu-D-Trp(CH$_3$)-D-Pya-OC$_2$H$_5$ (920 mg) in DMF (20 ml) was added 1N NaOH (7.3 ml) at room temperature. After 10 minutes, 1N HCl (8.5 ml) was added and the solution was evaporated in vacuo. The residue was dissolved in 1N HCl (50 ml) and water (200 ml), and applied to a column of "Diaion HP-20" (trademark, made by Mitsubishi Chemical Industries) eluting with MeOH (300 ml). After the eluate was concentrated in vacuo, the residue (750 mg) was dissolved in 1N NaOH (1.24 ml) and lyophilized to give the object compound as a white powder (728 mg).

Rf: 0.45 (CHCl$_3$:MeOH:AcOH=8:1:1)

EXAMPLE 10

N-[(1S)-2,2-Dimethyl-1-(N,N-dimethylcarbamoyl)propyl]carbamoyl-L-Leu-OH (0.28 g), H-D-Trp(CH$_3$-)-D-Pya-OC$_2$H$_5$.2HCl (0.41 g), HOBT (0.14 g), WSCD (0.16 g) and TEA (89 mg) were reacted in DMF (7 ml) in a similar manner to that of Example 1-1) to give the object compound (0.40 g).

mp: 141°–145° C. Rf: 0.43 (CHCl$_3$:MeOH=9:1) NMR (CDCl$_3$, δ): 0.82 (3H, d, J=6.0 Hz), 0.87 (3H, d, J=6.0 Hz), 1.15 (3H, t, J=6.0 Hz), 1.35 (2H, t, J=6.0 Hz), 1.65 (1H, m), 2.58 (3H, s), 3.06 (3H, s), 3.1–3.3 (4H, m), 3.70 (3H, s), 4.06 (2H, q, J=6.0 Hz), 4.34 (1H, q, J=6.0 Hz), 4.75 (1H, d, J=10.0 Hz), 4.90 (1H, q, J=6.0 Hz), 5.13 (1H, q, J=6.0 Hz), 6.20 (1H, d, J=10.0 Hz), 6.48 (1H, d, J=8.0 Hz), 6.58 (1H, d, J=7.5 Hz), 6.90 (1H, s), 6.95 –7.30 (6H, m), 7.56 (1H, td, J=7.5, 2.0 Hz), 7.65 (1H, d, J=7.5 Hz), 7.98 (1H, d, J=8.0 Hz), 8.34 (1H, d, J=5.0 Hz)

EXAMPLE 11

(2S)-2-[N-[(1S)-2,2-Dimethyl-1-(N,N-dimethylcarbamoyl)propyl]carbamoyloxy]-4-methylvaleric acid (0.15 g), H-D-TrP(CH$_3$)-D-Pya-OC$_2$H$_5$.2HCl (0.24 g), HOBT (77 mg), WSCD (88 mg) and NMM (53 mg) were reacted in DMF (4 ml) in a similar manner to that of Example 1-1) to give the object compound (0.33 g).

Rf: 0.73 (CHCl$_3$:MeOH=9:1)

EXAMPLE 12

N-(Hexahydro-1H-azepin-1-ylcarbonyl)-L-Leu-OH (1.51 g), 2HCl.H-D-Trp(CH$_3$)-D-pya-OC$_2$H$_5$ (2.50 g), WSCD (997 mg), HOBT (868 mg) and NMM (541 mg) were reacted in DMF (60 ml) in a similar manner to that of Example 1-1) to give the object compound (2.16 g).

Rf: 0.34 (ethyl acetate) NMR (CDCl$_3$δ): 0.82 (3H, d, J=6.0 Hz), 0.84 (3H, d, J=6.0 Hz), 1.18 (3H, t, J=7.5 Hz), 1.3–1.8 (11H, m), 3.1–3.5 (7H, m), 3.68 (3H, s), 4.10 (2H, q, J=7.5 Hz), 4.10 (1H, br), 4.7–4.9 (3H, m), 6.68 (1H, d, J=8.0 Hz), 6.95 (1H, s), 7.0–7.3 (5H, m), 7.5 (1H, td, J=8.0, 2.0 Hz), 7.64 (2H, t, J=8.0 Hz), 8.28 (1H, d, J=5.0 Hz)

EXAMPLE 13

(2R)-2-(Hexahydro-1H-azepin-1-ylcarbonylmethyl)-4-methylvaleric acid (982 mg). 2HCl-H-D-TrP(CH$_3$)-D-Pya-OC$_2$H$_5$ (1.54 g), WSCD (612 mg), HOBT (532 mg) and TEA (332 mg) were reacted in DMF (30 ml) in a similar manner to that of Example 1-1) to give the object compound (1.41 g).

Rf: 0.43 (CHCl$_3$:MeOH=9:1)

EXAMPLE 14

N-(Octahydroazocin-1-ylcarbonyl)-L-Leu-OH (191 mg), 2HCl.H-D-Trp(CH$_3$)-D-Pya-OC$_2$H$_5$ (300 mg), WSCD (120 mg), HOBT (104 mg) and TEA (65 mg) were reacted in DMF (20 ml) in a similar manner to that of Example 1-1) to give the object compound (340 mg).

Rf: 0.60 (CHCl$_3$:MeOH=9:1)

EXAMPLE 15

2HCl.H-L-Leu-D-Trp(CH$_3$)-D-Pya-OC$_2$H$_5$ (4.35 g), hexahydro-1H-azepin-1-ylcarbonyl chloride (1.29 g) and TEA (2.33 g) were reacted in DMF (60 ml) in a similar manner to that of Example 4-1) to give the object compound (1.95 g).

Rf: 0.44 (CHCl$_3$:MeOH=9:1)

EXAMPLE 16

To a solution of N-(hexahydro-1H-azepin-1-ylcarbonyl)-L-Leu-D-Trp(CH$_3$)-D-Pya-OC$_2$H$_5$ (37 g) in ethanol (740 ml) was added 1N NaOH (146 ml) under ice-bath cooling. After stirring for 30 minutes, 1N HCl (150 ml) was added to the reaction mixture, and the solvent was removed by evaporation in vacuo. The residue was dissolved in 1N HCl (500 ml) and water (5000 ml) and applied to a column chromatography using non-ionic adsorption resin "Diaion HP-20" (3 l), which was eluted with methanol (10 l). After the eluent was concentrated in vacuo, the residue was crystallized from n-hexane to give the object compound (34.1 g).

mp: 113°-118° C. Rf: 0.34 (CHCl$_3$:MeOH:AcOH=8:1:1) NMR (CDCl$_3$, δ): 0.89 (6H, d, J=5.0 Hz), 1.32-1.80 (11H, m), 3.11 (2H, d, J=6.0 Hz), 3.16-3.53 (6H, m), 3.78 (3H, s), 4.20 (1H, br), 4.22-4.48 (1H, m), 4.59 (1H, q, J=6.0 Hz), 4.77 (1H, q, J=7.0 Hz), 4.90 (1H, d, J=7.5 Hz), 7.01 (1H, s), 7.04-7.52 (7H, m), 7.71 (1H, d, J=7.0 Hz), 7.82 (1H, t, J=8.0 Hz), 8.48 (1H, d, J=5.0 Hz)

EXAMPLE 17

N-(Hexahydro-1H-azepin-1-ylcarbonyl)-L-Leu-D-Trp(CH$_3$)-D-Pya-OC$_2$H$_5$ (1.35 g) and 1N NaOH (6.4 ml) were reacted in ethanol (30 ml) in a similar manner to that of Example 9 to give the object compound (1.08 g).

Rf: 0.44 (CHCl$_3$:MeOH:AcOH=8:1:1) NMR (DMSO-d$_6$, δ): 0.74 (3H, d, J=3.0 Hz), 0.79 (3H, d, J=3.0 Hz), 1.08-1.67 (11H, m), 2.72-3.12 (3H, m), 3.18-3.38 (5H, m), 3.69 (3H, s), 4.09-4.25 (2H, m), 4.28-4.43 (1H, m), 6.08 (1H, d, J=8.5 Hz), 6.92-7.15 (4H, m), 7.25 (1H, d, J=8.0 Hz), 7.32 (1H, d, J=8.0 Hz), 7.49-7.62 (2H, m), 7.69 (1H, d, J=8.5 Hz), 8.03 (1H, d, J=9.0 Hz), 8.40 (1H, d, J=4.0 Hz)

EXAMPLE 18

N-[N-[(1S)-2,2-Dimethyl-1-(N,N-dimethylcarbamoyl)propyl]carbamoyl]-L-Leu-D-Trp(CH$_3$)-D-Pya-OC$_2$H$_5$ (0.31 g) and 1N NaOH (1.5 ml) were reacted in DMF in a similar manner to that of Example 9 to give the object compound (0.25 g).

Rf: 0.31 (CHCl$_3$:MeOH:AcOH=8:1:1) NMR (DMSO-d$_6$, δ): 0.66 (6H, d, J=6.0 Hz), 0.88 (9H, s), 1.0-1.3 (3H, m), 2.7-3.3 (4H, m), 2.8 (3H, s), 3.08 (3H, s), 3.68 (3H, s), 4.08 (1H, q, J=6.0 Hz), 4.20 (1H, q, J=5.0 Hz), 4.38 (1H, m), 4.50 (1H, d, J=9.0 Hz), 6.37 (1H, d, J=9.0 Hz), 6.48 (1H, d, J=7.5 Hz), 6.9-7.15 (4H, m), 7.2 (1H, d, J=7.5 Hz), 7.3 (1H, d, J=7.5 Hz), 7.45-7.6 (2H, m), 7.66 (1H, d, J=7.5 Hz), 8.28 (1H, d, J=8.0 Hz), 8.38 (1H, d, J=4.0 Hz)

EXAMPLE 19

N-[(2S)-2-[N-[(1S)-2,2-dimethyl-1-(N,N-dimethylcarbamoyl)propyl]carbamoyloxy]-4-methylvaleryl]-D-Trp(CH$_3$)-D-Pya-OC$_2$H$_5$ (0.30 g) and 1N NaOH (1.3 ml) were reacted in DMF (2.6 ml) in a similar manner to that of Example 9 to give the object compound (0.26 g).

Rf: 0.20 (CHCl$_3$:MeOH:AcOH=8:1:1) NMR (DMSO-d$_6$, δ): 0.78 (6H, d, J=6.5 Hz), 0.88 (9H, s), 1.2-1.6 (3H, m), 2.7-3.4 (4H, m), 2.83 (3H, s), 3.05 (3H, s), 3.66 (3H, s), 4.16 (1H, q, J=6.0 Hz), 4.34-4.48 (2H, m), 4.75 (1H, q, J=3.0 Hz), 6.9-7.7 (10H, m), 8.16 (1H, d, J=10.0 Hz), 8.40 (1H, d, J=4.0 Hz)

EXAMPLE 20

N-[(2R)-2-(Hexahydro-1H-azepin-1-ylcarbonylmethyl)-4-methylvaleryl]-D-Trp(CH$_3$)-D-Pya-OC$_2$H$_5$ (1.10 g) and 1N NaOH (5.2 ml) were reacted in ethanol (20 ml) in a similar manner to that of Example 9 to give the object compound (783 mg).

Rf: 0.49 (CHCl$_3$:MeOH:AcOH=8:1:1)

EXAMPLE 21

N-(Octahydroazocin-1-ylcarbonyl)-L-Leu-D-Trp(CH$_3$)-D-Pya-OC$_2$H$_5$ (300 mg) and 1N NaOH (2.4 ml) were reacted in ethanol (10 ml) in a similar manner to that of Example 9 to give the object compound (210 mg).

Rf: 0.68 (CHCl$_3$:MeOH:AcOH=8:2:1) NMR (DMSO-d$_6$, δ): 0.75 (6H, d, J=5.5 Hz), 1.02-1.65 (16H, m), 2.72-3.32 (5H, m), 3.68 (3H, s), 4.08-4.26 (2H, m), 4.29-4.45 (1H, m), 5.93 (1H, d, J=8.5 Hz), 6.92-7.18 (4H, m), 7.13 (1H, d, J=8.0 Hz), 7.32 (1H, d, J=9.0 Hz), 7.48-7.69 (3H, m), 7.97 (1H, d, J=9.0 Hz), 8.38 (1H, d, J=4.5 Hz)

EXAMPLE 22

To a solution of N-(hexahydro-1H-azepin-1-ylcarbonyl)-L-Leu-D-Trp(CH$_3$)-D-Pya-OC$_2$H$_5$ (800 mg) in ethanol (10 ml) was added 4N hydrogen chloride in ethyl acetate solution (0.63 ml) under ice-bath cooling. After stirring for 5 minutes at the same temperature, the solution was concentrated in vacuo to give the object compound (828 mg).

Rf: 0.64 (CHCl$_3$:MeOH=9:1) NMR (DMSO-d$_6$, δ): 0.71 (3H, d, J=5.0 Hz), 0.77 (3H, d, J=5.0 Hz), 1.14 (3H, t, J=6.0 Hz), 1.15-1.66 (11H, m), 2.82 (1H, q, J=11.0 Hz), 3.08-4.18 (8H, m), 3.72 (3H, s), 4.08 (2H, q, J=7.5 Hz), 4.32-4.48 (1H, m), 4.63-4.80 (1H, m), 6.13 (1H, br), 7.02 (2H, t, J=7.0 Hz), 7.13 (1H, t, J=7.5 Hz), 7.37 (1H, d, J=8.0 Hz), 7.57 (1H, d, J=7.5 Hz), 7.82 (2H, t, J=7.0 Hz), 8.22-8.42 (2H, m), 8.78 (2H, d, J=5.0 Hz)

EXAMPLE 23

N-[(2R)-2-hexahydro-1H-azepin-1-ylcarbonylmethyl)-4-methylvaleryl]-D-Trp(CH$_3$)-D-Pya-OC$_2$H$_5$ (300 mg), 4N hydrogen chloride in ethyl acetate (0.36 ml) were reacted in ethanol (10 ml) in a similar manner to that of Example 22 to give the object compound (298 mg).

Rf: 0.43 (CHCl$_3$:MeOH=9:1)

The object compounds in Examples 24 to 71 could be obtained by reacting the corresponding starting compounds (II) and (III) in a similar manner to that of Example 1-1).

The physico-chemical properties of these object compounds are provided hereinbelow.

EXAMPLE 24
mp: 193°-195° C. Rf: 0.49 (CHCl$_3$:MeOH=9:1)

EXAMPLE 25
mp: 186°-189° C. Rf: 0.62 (CHCl$_3$:MeOH=9:1)

EXAMPLE 26
mp: 181°-183° C. Rf: 0.56 (CHCl$_3$:MeOH:AcOH=8:1:1)

EXAMPLE 27
Rf: 0.49 (CHCl$_3$:MeOH=9:1)

EXAMPLE 28
Rf: 0.77 (CHCl$_3$:MeOH=9:1)

EXAMPLE 29
Rf: 0.77 (CHCl$_3$:MeOH=9:1)

EXAMPLE 30
Rf: 0.57 (CHCl$_3$:MeOH=9:1)

EXAMPLE 31
Rf: 0.56 (CHCl$_3$:MeOH=9:1)

EXAMPLE 32
mp: 184°-185° C. Rf: 0.54 (CHCl$_3$:MeOH=9:1)

EXAMPLE 33
Rf: 0.77 (CHCl$_3$:MeOH=9:1)

EXAMPLE 34
Rf: 0.43 (CHCl$_3$:MeOH=9:1)

EXAMPLE 35
Rf: 0.53 (CHCl$_3$:MeOH=9:1)

EXAMPLE 36
Rf: 0.36 (CHCl$_3$:MeOH=9:1)

EXAMPLE 37
mp: 79°-81° C. Rf: 0.60 (CHCl$_3$:MeOH:AcOH=16:1:1)

EXAMPLE 38
mp: 69°-71° C. Rf: 0.43 (CHCl$_3$:MeOH=9:1)

EXAMPLE 39
mp: 54°-55° C. Rf: 0.41 (CHCl$_3$:MeOH=9:1)

EXAMPLE 40
mp: 100°-105° C. Rf: 0.41 (CHCl$_3$:MeOH=9:1)

EXAMPLE 41
Rf: 0.53 (CHCl$_3$:MeOH=9:1)

EXAMPLE 42
Rf: 0.55 (CHCl$_3$:MeOH=9:1)

EXAMPLE 43
mp: 62°-68° C. Rf: 0.52 (CHCl$_3$:MeOH=9:1)

EXAMPLE 44
mp: 60°-67° C. Rf: 0.51 (CHCl$_3$:MeOH=9:1)

EXAMPLE 45
mp: 70°-75° C. Rf: 0.58 (CHCl$_3$:MeOH=9:1)

EXAMPLE 46
mp: 80°-83° C. Rf: 0.53 (CHCl$_3$:MeOH=9:1)

EXAMPLE 47
Rf: 0.55 (CHCl$_3$:MeOH=9:1)

EXAMPLE 48
Rf: 0.48 (CHCl$_3$:MeOH=9:1)

EXAMPLE 49
mp: 140°-142° C. Rf: 0.43 (CHCl$_3$:MeOH=9:1)

EXAMPLE 50
Rf: 0.52 (CHCl$_3$:MeOH=9:1)

EXAMPLE 51
mp: 135°-138° C. Rf: 0.31 (CHCl$_3$:MeOH=9:1)

EXAMPLE 52
mp: 190°-193° C. Rf: 0.70 (CHCl$_3$:MeOH=9:1)

EXAMPLE 53
mp: 185°-188° C. Rf: 0.50 (CHCl$_3$:MeOH=9:1)

EXAMPLE 54
mp: 170°-178° C. Rf: 0.48 (CHCl$_3$:MeOH=9:1)

EXAMPLE 55
mp: 194°-196° C. Rf: 0.45 (CHCl$_3$:MeOH=9:1)

EXAMPLE 56
mp: 166°-167° C. Rf: 0.70 (CHCl$_3$:MeOH=9:1)

EXAMPLE 57
mp: 110°-115° C. Rf: 0.59 (CHCl$_3$:MeOH=9:1)

EXAMPLE 58
mp: 79°-80° C. Rf: 0.79 (CHCl$_3$:MeOH=9:1)

EXAMPLE 59
mp: 77°-79° C. Rf: 0.52 (CHCl$_3$:MeOH=9:1)

EXAMPLE 60
Rf: 0.36 (CHCl$_3$:MeOH=9:1)

EXAMPLE 61
Rf: 0.53 (CHCl$_3$:MeOH=9:1)

EXAMPLE 62
Rf: 0.53 (CHCl$_3$:MeOH=9:1)

EXAMPLE 63
mp: 185°-188° C. Rf: 0.53 (CHCl$_3$:MeOH=9:1)

EXAMPLE 64
mp: 170°-175° C. Rf: 0.58 (CHCl$_3$:MeOH=9:1)

EXAMPLE 65
Rf: 0.71 (CHCl$_3$:MeOH=9:1)

EXAMPLE 66
mp: 183°-190° C. Rf: 0.60 (CHCl$_3$:MeOH=9:1)

EXAMPLE 67

Rf: 0.70 (CHCl$_3$:MeOH=9:1)

EXAMPLE 68

Rf: 0.79 (CHCl$_3$:MeOH=9:1)

EXAMPLE 69 mp: 159°-161° C. Rf: 0.62 (CHCl$_3$:MeOH=9:1)

EXAMPLE 70

Rf: 0.51 (CHCl$_3$:MeOH=9:1)

EXAMPLE 71 mp: 148°-150° C. Rf: 0.78 (CHCl$_3$:MeOH=9:1)

EXAMPLE 72

To a solution of HCl.H-L-Ile-OMe (135 mg) and Et$_3$N (50.2 mg) in dry toluene (10 ml) was added trichloromethyl chloroformate (0.055 ml). After the solution was refluxed for 30 minutes, it was concentrated under reduced pressure. The resulting residue was dissolved in DMF (10 ml) and a mixture of HCl.H-L-Leu-D-Trp(CH$_3$)-D-Phe-OBzl (300 mg) and Et$_3$N (50.2 mg) in DMF (10 ml) was added to the solution at room temperature. After the reaction mixture was stirred for 1 hour, the solvent was removed in vacuo. The resulting residue was dissolved in ethyl acetate (30 ml) and the solution was washed with 5% HCl, 1M sodium bicarbonate and saturated sodium chloride solution successively, dried over anhydrous magnesium sulfate, and concentrated under reduced pressure. The residue was crystallized from ether to give the object compound (324 mg).

mp: 184°-186° C. Rf: 0.80 (CHCl$_3$:MeOH=9:1)

EXAMPLE 73

To a mixture of HCl.H-L-Leu-D-Trp(CH$_3$)-D-Phe-OBzl (0.12 g), 4-pyridylacetic acid (38 mg) and NMM (24 mg) in DMF (2 ml) was added WSCD (37 mg) under ice-bath cooling. After being stirred for 3 hours at room temperature, the mixture was concentrated in vacuo and the residue was dissolved in ethyl acetate. The solution was washed with 0.5N HCl, water, saturated sodium bicarbonate and water successively, dried over magnesium sulfate and evaporated in vacuo. The residue was triturated with ether to give the object compound (107 mg).

mp: 122°-125° C. Rf: 0.46 (CHCl$_3$:MeOH=9:1)

The object compounds in Examples 74 to 82 could be obtained by reacting the corresponding starting compounds (I-a) and (IV) in a similar manner to that of Example 73.

The physico-chemical properties of these object compounds are provided hereinbelow.

EXAMPLE 74 mp: 105°-110° C. Rf: 0.50 (CHCl$_3$:MeOH=9:1)

EXAMPLE 75 mp: 98°-108° C. Rf: 0.65 (CHCl$_3$:MeOH=9:1)

EXAMPLE 76 mp: 173°-175° C. Rf: 0.84 (CHCl$_3$:MeOH=9:1)

EXAMPLE 77 mp: 196°-199° C. Rf: 0.79 (CHCl$_3$:MeOH=9:1)

EXAMPLE 78 mp: 139°-141° C. Rf: 0.60 (CHCl$_3$:MeOH:AcOH=8:2:1)

EXAMPLE 79 mp: 90°-96° C. Rf: 0.36 (CHCl$_3$:MeOH=9:1)

EXAMPLE 80 mp: 206°-209° C. Rf: 0.45 (CHCl$_3$:MeOH=9:1)

EXAMPLE 81 mp: 124°-128° C. Rf: 0.56 (CHCl$_3$:MeOH=9:1)

EXAMPLE 82

Rf: 0.64 (CHCl$_3$:MeOH=9:1)

EXAMPLE 83

To a mixture of benzylsulfonyl chloride (0.18 g) and HCl.H-L-Leu-D-Trp(CH$_3$)-D-Pya-OC$_2$H$_5$ (0.50 g) in DMF (10 ml) was added Et$_3$N (0.42 ml) at 0° C. After the reaction was completed, the solution was evaporated to dryness in vacuo. The residue was dissolved in ethyl acetate, and the solution was washed with 0.5N HCl, dried over magnesium sulfate and concentrated in vacuo. The residual solid was triturated with ether to give the object compound (0.29 g).

mp: 98°-100° C. Rf: 0.51 (CHCl$_3$:MeOH=9:1)

EXAMPLE 84

Morpholinocarbonylchloride (108 mg), 2HCl.H-L-Leu-D-Trp(CH$_3$)-D-Pya-OC$_2$H$_5$ (350 mg) and Et$_3$N (122 mg) were reacted in a similar manner to that of Example 83 to give the object compound.

Rf: 0.45 (CHCl$_3$:MeOH=9:1)

The object compounds in Examples 85 to 91 could be obtained by reacting the corresponding starting compound (I-a) with the isocyanate compound (IV) in a similar manner to that of Example 4-1).

The physico-chemical properties of these object compounds are provided hereinbelow.

EXAMPLE 85 mp: 222°-223° C. Rf: 0.79 (CHCl$_3$:MeOH=9:1)

EXAMPLE 86 mp: 198°-204° C. Rf: 0.49 (CHCl$_3$:MeOH=9:1)

EXAMPLE 87 mp: 205°-206° C. Rf: 0.46 (CHCl$_3$:MeOH=9:1)

EXAMPLE 88 mp: 216°-218° C. Rf: 0.45 (CHCl$_3$:MeOH=9:1)

EXAMPLE 89 mp: 188°-202° C. Rf: 0.53 (CHCl$_3$:MeOH=9:1)

EXAMPLE 90 mp: 167°-172° C. Rf: 0.53 (CHCl$_3$:MeOH=9:1)

EXAMPLE 91 mp: 163°-167 ° C. Rf: 0.53 (CHCl$_3$:MeOH=9:1)

EXAMPLE 92

To a mixture of N-cyclohexylcarbamoyl-L-Leu-D-Trp(CH$_3$)-OH (0.40 g), H-D-4Pya-OC$_2$H$_5$.2HCl (0.26 g), NMM (0.10 g) and HOBT (0.14 g) in DMF (8 ml) was added WSCD (0.16 g) under ice-bath cooling.

After being stirred at room temperature, the mixture was concentrated in vacuo and the residue was dissolved in ethyl acetate. The solution was washed with 0.5N HCl, water, saturated sodium bicarbonate and water successively, dried over magnesium sulfate and evaporated in vacuo. The residue was triturated with ether to give the object compound (0.45 g).

mp: 182°–186° C. Rf: 0.32 (CHCl$_3$:MeOH:AcOH=16:1:1)

The object compounds in Examples 93 to 98 could be obtained by reacting the corresponding starting compounds (V) and (VI) in a similar manner to that of Example 92.

The physico-chemical properties of these object compounds are provided hereinbelow.

EXAMPLE 93
mp: 170°–173° C. Rf: 0.43 (CHCl$_3$:MeOH=9:1)

EXAMPLE 94
mp: 181°–182° C. Rf: 0.71 (CHCl$_3$:MeOH=9:1)

EXAMPLE 95
mp: 197°–198° C. Rf: 0.70 (CHCl$_3$:MeOH=9:1)

EXAMPLE 96
mp: 115°–123° C. Rf: 0.74 (CHCl$_3$:MeOH=9:1)

EXAMPLE 97
mp: 148°–156° C. Rf: 0.52 (CHCl$_3$:MeOH:AcOH=16:1:1)

EXAMPLE 98
mp: 154°–158° C. Rf: 0.51 (CHCl$_3$:MeOH=9:1)

The object compounds in Examples 99 to 145 could be obtained by hydrolyzing the corresponding ethyl ester compound (I-c) with an aqueous NaOH in a similar manner to that of Example 1-2), 9 or 16.

The physico-chemical properties of these object compounds are provided hereinbelow.

EXAMPLE 99
mp: 167°–170° C. Rf: 0.44 (CHCl$_3$:MeOH:AcOH=8:1:1)

EXAMPLE 100
mp: 173°–178° C. Rf: 0.62 (CHCl$_3$:MeOH:AcOH=8:1:1)

EXAMPLE 101
mp: 150°–155° C. Rf: 0.25 (CHCl$_3$:MeOH:AcOH=8:1:1)

EXAMPLE 102
Rf: 0.51 (CHCl$_3$:MeOH:AcOH=8:1:1)

EXAMPLE 103
Rf: 0.69 (CHCl$_3$:MeOH:AcOH=8:1:1)

EXAMPLE 104
Rf: 0.66 (CHCl$_3$:MeOH:AcOH=8:2:1)

EXAMPLE 105
Rf: 0.78 (CHCl$_3$:MeOH:AcOH=8:2:1)

EXAMPLE 106
Rf: 0.57 (CHCl$_3$:MeOH:AcOH=8:1:1)

EXAMPLE 107
Rf: 0.52 (CHCl$_3$:MeOH:AcOH=8:1:1)

EXAMPLE 108
Rf: 0.72 (CHCl$_3$:MeOH:AcOH=8:1:1)

EXAMPLE 109
Rf: 0.56 (CHCl$_3$:MeOH:AcOH=20:20:1)

EXAMPLE 110
Rf: 0.32 (CHCl$_3$:MeOH:AcOH=8:1:1)

EXAMPLE 111
Rf: 0.31 (CHCl$_3$:MeOH:AcOH=8:1:1)

EXAMPLE 112
mp: 150°–155° C. Rf: 0.29 (CHCl$_3$:MeOH:AcOH=8:2:1)

EXAMPLE 113
Rf: 0.31 (CHCl$_3$:MeOH:AcOH=8:1:1)

EXAMPLE 114
Rf: 0.31 (CHCl$_3$:MeOH:AcOH=8:1:1)

EXAMPLE 115
Rf: 0.33 (CHCl$_3$:MeOH:AcOH=8:1:1)

EXAMPLE 116
Rf: 0.33 (CHCl$_3$:MeOH:AcOH=8:1:1)

EXAMPLE 117
Rf: 0.34 (CHCl$_3$:MeOH:AcOH=8:1:1)

EXAMPLE 118
Rf: 0.32 (CHCl$_3$:MeOH:AcOH=8:1:1)

EXAMPLE 119
Rf: 0.33 (CHCl$_3$:MeOH:AcOH=8:1:1)

EXAMPLE 120
Rf: 0.38 (CHCl$_3$:MeOH:AcOH=8:1:1)

EXAMPLE 121
Rf: 0.34 (CHCl$_3$:MeOH:AcOH=8:1:1)

EXAMPLE 122
Rf: 0.35 (CHCl$_3$:MeOH:AcOH=8:1:1)

EXAMPLE 123
Rf: 0.33 (CHCl$_3$:MeOH:AcOH=8:1:1)

EXAMPLE 124
Rf: 0.31 (CHCl$_3$:MeOH:AcOH=8:1:1)

EXAMPLE 125
Rf: 0.33 (CHCl$_3$:MeOH:AcOH=8:1:1)

EXAMPLE 126
Rf: 0.28 (CHCl$_3$:MeOH:AcOH=8:1:1)

EXAMPLE 127
Rf: 0.30 (CHCl$_3$:MeOH:AcOH=8:1:1)

EXAMPLE 128
Rf: 0.32 (CHCl$_3$:MeOH:AcOH=8:1:1)

EXAMPLE 129
Rf: 0.29 (CHCl$_3$:MeOH:AcOH=8:1:1)

EXAMPLE 130
Rf: 0.33 (CHCl$_3$:MeOH:AcOH=8:1:1)

EXAMPLE 131
Rf: 0.29 (CHCl$_3$:MeOH:AcOH=8:1:1)

EXAMPLE 132
Rf: 0.33 (CHCl$_3$:MeOH:AcOH=8:1:1)

EXAMPLE 133
Rf: 0.31 (CHCl$_3$:MeOH:AcOH=8:1:1)

EXAMPLE 134
Rf: 0.37 (CHCl$_3$:MeOH:AcOH=8:1:1)

EXAMPLE 135
Rf: 0.46 (CHCl$_3$:MeOH:AcOH=8:1:1)

EXAMPLE 136
Rf: 0.24 (CHCl$_3$:MeOH:AcOH=8:1:1)

EXAMPLE 137
Rf: 0.38 (CHCl$_3$:MeOH:AcOH=8:1:1)

EXAMPLE 138
Rf: 0.29 (CHCl$_3$:MeOH:AcOH=8:1:1)

EXAMPLE 139
Rf: 0.32 (CHCl$_3$:MeOH:AcOH=8:1:1)

EXAMPLE 140
Rf: 0.31 (CHCl$_3$:MeOH:AcOH=8:1:1)

EXAMPLE 141
Rf: 0.33 (CHCl$_3$:MeOH:AcOH=8:1:1)

EXAMPLE 142
Rf: 0.53 (CHCl$_3$:MeOH:AcOH=8:1:1)

EXAMPLE 143
Rf: 0.57 (CHCl$_3$:MeOH:AcOH=8:1:1)

EXAMPLE 144
Rf: 0.50 (CHCl$_3$:MeOH:AcOH=8:1:1)

EXAMPLE 145
Rf: 0.62 (CHCl$_3$:MeOH:AcOH=8:1:1) NMR (DMSO-d$_6$, δ): 0.54 (3H, d, J=6.0 Hz), 0.64 (3H, d, J=6.0 Hz), 0.72 (−1.02 (2H, m), 1.10–1.72 (13H, m), 2.22–2.32 (1H, m), 2.55–2.82 (2H, m), 2.93–3.60 (6H, m), 3.68 (3H, s), 4.04–4.10 (1H, m), 4.24–4.40 (1H, m), 6.94–7.18 (4H, m), 7.20–7.42 (2H, m), 7.46–7.68 (3H, m), 8.30 (1H, d, J=7.5 Hz), 8.41 (1H, d, J=4.0 Hz)

The object compounds in Examples 146 to 151 could be obtained by hydrolyzing the corresponding benzyl ester compound (I-c) with an aqueous NaOH in a similar manner to that of Example 1-2), 9 or 16.

The physico-chemical properties of these object compounds are provided hereinbelow.

EXAMPLE 146
mp: 120°–124° C. Rf: 0.85 (CHCl$_3$:AcOH=8:1:1)

EXAMPLE 147
mp: 220°–236° C. Rf: 0.16 (CHCl$_3$:MeOH:AcOH=16:1:1) FAB MS m/z: 598 [M+H]$^+$

EXAMPLE 148
mp: 214°–218 ° C. Rf: 0.20 (CHCl$_3$:MeOH:AcOH:16:1:1) FAB MS m/z: 598 [M+H]$^+$

EXAMPLE 149
mp: 174°–180° C. Rf: 0.32 (CHCl$_3$:MeOH:AcOH=16:1:1) FAB MS m/z: 598 [M+H]$^+$

EXAMPLE 150
mp: 194° C. (dec.) Rf: 0.51 (CHCl$_3$:MeOH:AcOH=16:1:1) FAB MS m/z: 711 [M+H]$^+$

EXAMPLE 151
mp: 195° C. (dec.) Rf: 0.51 (CHCl$_3$:MeOH:AcOH=16:1:1) FAB MS m/z: 711 [M+H]$^+$ The object compounds in Examples 152 to 157 could be obtained by hydrolyzing the corresponding ethyl ester compound (I-c) with an aqueous NaOH in a similar manner to that of Example 1-2), 9 or 16.

The physico-chemical properties of these object compounds are provided hereinbelow.

EXAMPLE 152
mp: 127°–145° C. Rf: 0.29 (CHCl$_3$:MeOH:AcOH=8:2:1) FAB MS m/z: 672 [M+H]$^+$

EXAMPLE 153
Rf: 0.36 (CHCl$_3$:MeOH:AcOH=8:1:1)

EXAMPLE 154
Rf: 0.38 (CHCl$_3$:MeOH:AcOH=8:1:1)

EXAMPLE 155
Rf: 0.35 (CHCl$_3$:MeOH:AcOH=8:1:1)

EXAMPLE 156
Rf: 0.32 (CHCl$_3$:MeOH:AcOH=8:1:1)

EXAMPLE 157
Rf: 0.45 (CHCl$_3$:MeOH:AcOH=8:1:1)

EXAMPLE 158
Isopropylcarbamoyl-L-Leu-D-Trp(CH$_3$)-D-Phe-OBzl (60 mg) was reacted with 1N NaOH (2 ml) in DMF (2 ml) at room temperature for 30 minutes in a similar manner to that of Example 1-2) to give the object compound (48 mg).

mp: 211°–213° C. Rf: 0.54 (CHCl$_3$:MeOH:AcOH=16:1:1)

The object compounds in Examples 159 to 166 could be obtained by hydrolyzing the corresponding ethyl ester compound (I-c) with an aqueous NaOH in a similar manner to that of Example 9.

The physico-chemical properties of these object compounds are provided hereinbelow.

EXAMPLE 159
mp: >250° C. Rf: 0.12 (CHCl$_3$:MeOH:AcOH=16:1:1)

EXAMPLE 160
mp: >250° C. Rf: 0.10 (CHCl$_3$:MeOH:AcOH=16:1:1)

EXAMPLE 161 mp: >250° C. Rf: 0.12 (CHCl₃:MeOH-:AcOH=16:1:1)

EXAMPLE 162 mp: >250° C. RF: 0.13 (CHCl₃:MeOH-:AcOH=16:1:1)

EXAMPLE 163 mp: 245° C. (dec.) Rf: 0.13 (CHCl₃:MeOH-:AcOH=16:1:1)

EXAMPLE 164 mp: >250° C. Rf: 0.13 (CHCl₃:MeOH-:AcOH=16:1:1)

EXAMPLE 165

Rf: 0.37 (CHCl₃:MeOH:AcOH=8:1:1)

EXAMPLE 166

Rf: 0.33 (CHCl₃:MeOH:AcOH=8:1:1)

The object compounds in Examples 167 to 169 could be obtained by hydrolyzing the corresponding benzyl ester compound (I-c) with an aqueous NaOH in a similar manner to that of Example 1-2) or 16.

The physico-chemical properties of those object compounds are provided hereinbelow.

EXAMPLE 167 mp: 171°–174° C. Rf: 0.51 (CHCl₃:MeOH-:AcOH=16:1:1) FAB MS m/z: 563 [M+H]+

EXAMPLE 168 mp: 165°–175° C. Rf: 0.51 (CHCl₃:MeOH-:AcOH=16:1:1) FAB MS m/z: 549 [M+H]+

EXAMPLE 169 mp: 132°–136° C. Rf: 0.31 (CHCl₃:MeOH:28% aq. ammonia=65:25:4)

EXAMPLE 170

N-Phenylacetyl-L-Leu-D-Trp(CH₃)-D-4-thiazolylalanine.HCl was hydrolyzed with 1N NaOH in a similar manner to that of Example 1-2) to give the object compound.

mp: 112°–116° C. Rf: 0.33 (CHCl₃:MeOH-:AcOH=8:1:1) FAB MS m/z: 604 [M+H]+

EXAMPLE 171

N-Cyclohexyloxycarbonyl-L-Leu-D-Trp(CH₃)-D-Pya-OC₂H₅ (0.25 g) was hydrolyzed with 1N NaOH (1 ml) in DMF (3 ml) in a similar manner to that of Example 9 to give the object compound (0.16 g).

Rf: 0.36 (CHCl₃:MeOH:AcOH=8:1:1)

EXAMPLE 172

N-Phenylacetyl-L-Leu-D-Trp(CHO)-D-Phe-OPac (0.20 g) was dissolved in a mixture of DMF (2 ml) and acetic acid (2 ml), and Zn powder (0.20 g) was added to the mixture at room temperature. After being stirred for 3 hours at the same temperature, the mixture was filtered and concentrated in vacuo. The residue was dissolved in ethyl acetate and the solution was washed with 0.5N HCl, dried over magnesium sulfate and concentrated in vacuo. The residue was triturated with ethyl ether to give the object compound (0.16 g).

mp: 230° C. (dec.) Rf: 0.51 (CHCl₃:MeOH-:AcOH=16:1:1) FAB-MS m/z: 611

EXAMPLE 173

Boc-D-alloIle-L-Leu-D-Trp(CHO)-D-Phe-OPac (0.16 g), zinc powder (0.16 g) and acetic acid (1.6 ml) were reacted in DMF (1.6 ml) in a similar manner to that of Example 172 to give the object compound (0.11 g).

mp: 197° C. (dec.) Rf: 0.49 (CHCl₃:MeOH-:AcOH=16:1:1) FAB-MS m/z: 707

EXAMPLE 174

A solution of N-[1(S)-methoxycarbonyl-2(S)-methylbutylcarbamoyl]-L-Leu-D-Trp(CH₃)-D-Phe-OBzl (270 mg) in DMF (20 ml) and water (1 ml) was hydrogenated over 10% Pd-C (50 mg) at 3 atmospheric pressure of hydrogen for 1 hour at room temperature. After the solution was filtered and the filtrate was concentrated in vacuo, the residue was crystallized from ethyl acetate and ether to give the object compound (198 mg).

mp: 210°–212° C. Rf: 0.48 (CHCl₃:MeOH-:AcOH=16:1:1)

EXAMPLE 175

N-[1(S)-Methoxycarbonyl-2(S)-methylbutylcarbamoyl]-L-Leu-D-Trp(CH₃)-D-Phe-OBzl (70 mg) and 1N NaOH (1 ml) in DMF (2 ml) were reacted in a similar manner to that of Example 1-2) to give the object compound (50 mg).

mp: 221°–225° C. Rf: 0.42 (CHCl₃:MeOH-:AcOH=16:1:1)

EXAMPLE 176

To a solution of cyclohexanol (0.10 ml) in tetrahydrofuran (3 ml) was added trichloromethyl chloroformate (0.13 ml) at room temperature. This solution was refluxed for 11 hours and the solvent was evaporated at atmospheric pressure in vacuo. The residual oil was dissolved in DMF (10 ml), and 2HCl.H-Leu-D-Trp(CH₃)-D-Pya-OEt (0.50 g) was added. The mixture was adjusted to about pH 7 with NMM (Ca. 0.2 g). After 10 minutes, the solvent was evaporated in vacuo, and the residue was dissolved in ethyl acetate (20 ml). This solution was washed with 1N HCl, saturated sodium bicarbonate and brine successively, dried over magnesium sulfate and then concentrated in vacuo. The residual solid was triturated with ethyl ether to give the object compound (0.29 g).

mp: 128°–130° C. Rf: 0.50 (CHCl₃:MeOH=9:1)

EXAMPLE 177

To a solution of N-phenylacetyl-L-Leu-D-Trp(CH₃)-D-His(Tos)-OBzl (78 mg) in DMF (2 ml) was added pyridine hydrochloride (0.15 g) at room temperature. After stirring for 2 hours, the solvent was removed by evaporation in vacuo and the residue was dissolved in ethyl acetate (20 ml). This solution was washed with 1M sodium bicarbonate (10 ml), dried over magnesium sulfate and evaporated in vacuo to give the object compound (45 mg).

mp : 118°–126° C. Rf: 0.28 (CHCl₃:MeOH=9:1)

EXAMPLE 178

Boc-D-phenylglycyl-L-Leu-D-Trp(CH₃)-D-Phe-OH (0.1 g), trifluoroacetic acid (1.5 ml) and anisole (0.2 ml) were reacted in a similar manner to that of Preparation 1-2) to give the object compound (90 mg).

mp: 135°-165° C. Rf: 0.20 (CHCl₃:MeOH:AcOH=16:1:1) FAB-MS m/z: 612 [M+H]⁺

EXAMPLE 179

Boc-L-Phenylglycyl-L-Leu-D-Trp(CH₃)-D-Phe-OH (0.11 g), TFA (1.5 ml) and anisole (0.2 ml) were reacted in a similar manner to that of Preparation 1-2) to give the object compound (107 mg).

mp: 145°-170° C. Rf: 0.20 (CHCl₃:MeOH:AcOH=16:1:1) FAB-MS m/z: 612 [M+H]⁺

EXAMPLE 180

The object compound could be obtained by reacting the corresponding starting compounds (II) and (III) in a similar manner to that of Example 1-1).

mp: 197°-202° C. Rf: 0.52 (CHCl₃:MeOH=9:1)

The object compounds in Examples 181 to 215 were obtained by reacting the corresponding starting compounds (II) and (III) in a similar manner to that of Example 1-1), preferably in the presence of a suitable base.

The physico-chemical properties of these object compounds are provided hereinbelow.

EXAMPLE 181

Rf: 0.52 (CHCl₃:MeOH=9:1)

EXAMPLE 182

Rf: 0.61 (CHCl₃:MeOH=9:1)

EXAMPLE 183

Rf: 0.80 (CHCl₃:MeOH=9:1)

EXAMPLE 184 mp: 192°-193° C. Rf: 0.67 (CHCl₃:MeOH=9:1)

EXAMPLE 185 mp: 155°-160° C. Rf: 0.82 (CHCl₃:MeOH=9:1)

EXAMPLE 186

Rf: 0.72 (CHCl₃:MeOH=9:1)

EXAMPLE 187

Rf: 0.34 (CHCl₃:MeOH:AcOH=8:1:1)

EXAMPLE 188 mp: 180°-185° C. Rf: 0.50 (CHCl₃:MeOH=9:1)

EXAMPLE 189 mp: 125°-127° C. Rf: 0.46 (CHCl₃:MeOH=9:1)

EXAMPLE 190

Rf: 0.78 (CHCl₃:MeOH=9:1)

EXAMPLE 191

Rf: 0.58 (CHCl₃:MeOH=9:1)

EXAMPLE 192 mp: 143°-146° C. Rf: 0.46 (CHCl₃:MeOH=9:1)

EXAMPLE 193

Rf: 0.40 (CHCl₃:MeOH=9:1)

EXAMPLE 194 mp: 180° C. Rf: 0.44 (CHCl₃:MeOH=9:1)

EXAMPLE 195 mp: 138°-140° C. Rf: 0.42 (CHCl₃:MeOH=9:1)

EXAMPLE 196

Rf: 0.37 (CHCl₃:MeOH=9:1)

EXAMPLE 197

Rf: 0.54 (CHCl₃:MeOH=9:1)

EXAMPLE 198

Rf: 0.66 (CHCl₃:MeOH=9:1)

EXAMPLE 199 mp: 186°-190° C. Rf: 0.611 (CHCl₃:MeOH:AcOH=8:2:1)

EXAMPLE 200 mp: 194°-197° C. Rf: 0.48 (CHCl₃:MeOH=9:1)

EXAMPLE 201

Rf: 0.39 (CHCl₃:MeOH=9:1)

EXAMPLE 202

Rf: 0.70 (CHCl₃:MeOH=9:1)

EXAMPLE 203 mp: 159°-161° C. Rf: 0.53 (CHCl₃:MeOH:AcOH=8:1:1)

EXAMPLE 204 mp: 183°-185° C. Rf: 0.58 (CHCl₃:MeOH=9:1)

EXAMPLE 205 mp: 154°-159° C. Rf: 0.58 (CHCl₃:MeOH=9:1)

EXAMPLE 206 mp: 82°-83° C. Rf: 0.58 (CHCl₃:MeOH=9:1)

EXAMPLE 207 mp: 164°-167° C. Rf: 0.83 (CHCl₃:MeOH=9:1)

EXAMPLE 208 mp: 148°-153° C. Rf: 0.58 (CHCl₃:MeOH=9:1)

EXAMPLE 209 mp: 116°-120° C. Rf: 0.83 (CHCl₃:MeOH=9:1)

EXAMPLE 210 mp: 88°-95° C. Rf: 0.64 (CHCl₃:MeOH=9:1)

EXAMPLE 211 mp: 143°-149° C. Rf: 0.57 (CHCl₃:MeOH=9:1)

EXAMPLE 212 mp: 182°-186° C. Rf: 0.58 (CHCl₃:MeOH=9:1)

EXAMPLE 213 mp: 155°-160° C. Rf: 0.58 (CHCl₃:MeOH=9:1)

EXAMPLE 214 mp: 180°-181° C. Rf: 0.58 (CHCl₃:MeOH=9:1)

EXAMPLE 215 mp: 199°-200° C. Rf: 0.38 (CHCl₃:MeOH=9:1)

EXAMPLE 216

To a mixture of phenylacetylchloride (0.27 g) and HCl.H-L-Leu-D-Trp(CHO)-βAla-OPac (0.94 g) in DMF (10 ml) was added triethylamine (0.54 ml) at 0° C. After 30 minutes, the solvent was evaporated in vacuo and the residue was dissolved in ethyl acetate (50 ml). The solution was washed with 0.5N hydrochloric acid (30 ml), dried over magnesium sulfate and concentrated in vacuo. The residual solid was triturated with ethyl ether to give the object compound (0.93 g).

mp: 163°–171° C. Rf: 0.45 (chloroform:methanol=9:1)

The object compounds in Examples 217 to 244 could be obtained by reacting the corresponding starting compounds (I-a) and (IV) in a similar manner to that of Example 73 or 216.

The physico-chemical properties of these object compounds are provided hereinbelow.

EXAMPLE 217
mp: 152°–153° C. Rf: 0.48 (CHCl$_3$:MeOH=9:1)

EXAMPLE 218
mp: 180°–181.5° C. Rf: 0.57 (CHCl$_3$:MeOH=9:1)

EXAMPLE 219
mp: 197°–199° C. Rf: 0.51 (CHCl$_3$:MeOH=9:1)

EXAMPLE 220
mp: 76°–79° C. Rf: 0.54 (CHCl$_3$:MeOH=9:1)

EXAMPLE 221
mp: 154°–160° C. Rf: 0.64 (CHCl$_3$:MeOH=9:1)

EXAMPLE 222
mp: 98°–103° C. Rf: 0.52 (CHCl$_3$:MeOH=9:1)

EXAMPLE 223
mp: 171°–174° C. Rf: 0.40 (CHCl$_3$:MeOH=9:1)

EXAMPLE 224
mp: 150°–153° C. Rf: 0.52 (CHCl$_3$:MeOH=9:1)

EXAMPLE 225
mp: 170°–172° C. Rf: 0.53 (CHCl$_3$:MeOH=9:1)

EXAMPLE 226
mp: 159°–168° C. Rf: 0.38 (CHCl$_3$:MeOH=9:1)

EXAMPLE 227
mp: 77°–88° C. Rf: 0.52 (CHCl$_3$:MeOH=9:1)

EXAMPLE 228
mp: 158°–162° C. Rf: 0.55 (CHCl$_3$:MeOH=9:1)

EXAMPLE 229
mp: 191°–193° C. Rf: 0.43 (CHCl$_3$:MeOH=9:1)

EXAMPLE 230
mp: 158°–162° C. Rf: 0.43 (CHCl$_3$:MeOH=9:1)

EXAMPLE 231
mp: 123°–126° C. Rf: 0.51 (CHCl$_3$:MeOH=9:1)

EXAMPLE 232
mp: 145°–146° C. Rf: 0.60 (CHCl$_3$:MeOH=9:1)

EXAMPLE 233
mp: 168°–170° C. Rf: 0.72 (CHCl$_3$:MeOH=9:1)

EXAMPLE 234
mp: 180°–183° C. Rf: 0.59 (CHCl$_3$:MeOH=9:1)

EXAMPLE 235
mp: 196°–204° C. Rf: 0.49 (CHCl$_3$:MeOH=9:1)

EXAMPLE 236
mp: 221°–226° C. Rf: 0.49 (CHCl$_3$:MeOH=9:1)

EXAMPLE 237
Rf: 0.47 (CHCl$_3$:MeOH=9:1)

EXAMPLE 238
mp: 198°–199° C. Rf: 0.65 (CHCl$_3$:MeOH=9:1)

EXAMPLE 239
mp: 104°–107° C. Rf: 0.59 (CHCl$_3$:MeOH=9:1)

EXAMPLE 240
mp: 228°–230° C. Rf: 0.57 (CHCl$_3$:MeOH=9:1)

EXAMPLE 241
mp: 196°–199° C. Rf: 0.53 (CHCl$_3$:MeOH=9:1)

EXAMPLE 242
mp: 207°–212° C. Rf: 0.51 (CHCl$_3$:MeOH=9:1)

EXAMPLE 243
mp: 186°–190° C. Rf: 0.49 (CHCl$_3$:MeOH=9:1)

EXAMPLE 244
Rf: 0.49 (CHCl$_3$:MeOH=9:1)

The object compounds in Examples 245 to 263 could be obtained by reacting the corresponding starting compounds (V) and (VI) in a similar manner to that of Example 92.

The physico-chemical properties of these object compounds are provided hereinbelow.

EXAMPLE 245
mp: 145°–148° C. Rf: 0.68 (CHCl$_3$:MeOH=9:1)

EXAMPLE 246
mp: 156°–160° C. Rf: 0.56 (CHCl$_3$:MeOH=9:1)

EXAMPLE 247
mp: 143°–147° C. Rf: 0.51 (CHCl$_3$:MeOH=9:1)

EXAMPLE 248
mp: 106°–110° C. Rf: 0.51 (CHCl$_3$:MeOH=9:1)

EXAMPLE 249
mp: 116°–119° C. Rf: 0.51 (CHCl$_3$:MeOH=9:1)

EXAMPLE 250
mp: 140°–143° C. Rf: 0.51 (CHCl$_3$:MeOH=9:1)

EXAMPLE 251
mp: 156°–160° C. Rf: 0.51 (CHCl$_3$:MeOH=9:1)

EXAMPLE 252
mp: 128°–130° C. Rf: 0.76 (CHCl$_3$:MeOH:AcOH=8:1:1)

EXAMPLE 253
mp: 120°–130° C. Rf: 0.85 (CHCl$_3$:MeOH:AcOH=8:1:1)

EXAMPLE 254 mp: 145°–148° C. Rf: 0.88 (CHCl$_3$:MeOH-:AcOH=8:2:1)

EXAMPLE 255 mp: 165°–167° C. Rf: 0.91 (CHCl$_3$:MeOH-:AcOH=8:2:1)

EXAMPLE 256

Rf: 0.37 (CHCl$_3$:MeOH:AcOH=8:1:1)

EXAMPLE 257

Rf: 0.56 (CHCl$_3$:MeOH=19:1)

EXAMPLE 258

Rf: 0.45 (CHCl$_3$:MeOH=19:1)

EXAMPLE 259 mp: 69°–70° C. Rf: 0.53 (CHCl$_3$:MeOH=9:1)

EXAMPLE 260

Rf: 0.45 (CHCl$_3$:MeOH=19:1)

EXAMPLE 261

Rf: 0.71 (CHCl$_3$:MeOH=9:1)

EXAMPLE 262 mp: 120°–130° C. Rf: 0.85 (CHCl$_3$:MeOH-:AcOH=8:1:1)

EXAMPLE 263 mp: 120°–122° C. Rf: 0.72 (CHCl$_3$:MeOH=9:1)

EXAMPLE 264

To a solution of N-phenylacetyl-L-Leu-D-Trp(Me)-D-Lys(Z)-OBzl (0.10 g) in DMF (2 ml) were added 10%-palladium on activated carbon (30 mg) and ammonium formate (0.2 g) at room temperature. After 3 hours, the suspended mixture was filtered and the filtrate was evaporated in vacuo. The residue was dissolved in 1N hydrochloric acid (1 ml) and purified with "Diaion HP-20" (Trademark, made by Mitsubishi Chemical Industries) column chromatography (eluent-:MeOH), and lyophilized to give the object compound (57.4 mg).

mp: 142°–160° C. Rf: 0.26 (chloroform:methanol:28% aqueous ammonia=5:3:1) FAB-MS m/z: 578 [M+H]

EXAMPLE 265

N-Phenylacetyl-L-Leu-D-Trp(CHO)-βAla-OH (0.38 g) and 1N NaOH (5 ml) were reacted in DMF (10 ml) in a similar manner to that of Example 1-2) to give the object compound (0.23 g).

mp: 85°–95° C. Rf: 0.48 (chloroform:methanol:acetic acid=16:1:1) FAB-MS m/z=507 [M+H]

EXAMPLE 266

N-Phenylacetyl-L-His(Tos)-D-Trp(CHO)-βAla-OMe (0.32 g) and pyridine hydrochloride (0.6 g) were reacted in DMF (6 ml) in a similar manner to that of Example 177 to give the object compound (0.20 g).

mp: 160°–166° C. Rf: 0.30 (10% MeOH in CHCl$_3$)

EXAMPLE 267

Boc-D-alloIle-L-Leu-D-Trp-D-Pya-OEt (2.0 g), and 4N HCl in dioxane (35 ml) were reacted in a similar manner to that of Preparation 1°-2) to give the object compound (1.82 g).

Rf: 0.62 (CHCl$_3$:MeOH:AcOH=8:2:1)

EXAMPLE 268

Boc-D-alloIle-L-Leu-D-Trp(CHO)-D-Glu(OBzl)-OH (0.67 g), TFA (10 ml) and anisole (1 ml) were reacted in a similar manner to that of Preparation 1-2) to give the object compound (0.60 g).

mp: 85°–110° C. Rf: 0.16 (chloroform:methanol:acetic acid=16:1:1) FAB-MS m/z: 679 [M+H]

The object compounds in Examples 269 to 292, and 349 were obtained by reacting the corresponding Pac ester compounds (I-c), Zn powder, acetic acid and DMF in a similar manner to that of Example 172.

The object compounds in Examples 293 to 294, 297 to 330, 333 to 345, 347–348, and 350 to 355 were obtained by reacting the corresponding methyl, ethyl, benzyl or Pac ester compound (I-c) with an aqueous NaOH in a similar manner to that of Example 1-2), 9 or 16.

The object compounds in Examples 295 to 296 and 331 to 332 were obtained by hydrogenating the corresponding benzyl, ester compound (I-c) in a similar manner to that of Preparation 1-4).

EXAMPLE 346

N-(β-Caprolactam-3-ylaminocarbonyl)-L-Leu-OH (293 mg), 2HCl.H-D-Trp(Me)-D-Pya-OEt (400 mg), WSCD (159 mg), HOBt (139 mg), Et$_3$N (87 mg) and DMF (10 ml) were reacted in a similar manner to that of Example 1-1) to give the object compound (411 mg).

The physico-chemical properties of these object compounds of Examples 269 to 355 are provided hereinbelow.

EXAMPLE 269 mp: 165°–168° C. Rf: 0.52 (CHCl$_3$:MeOH-:AcOH=16:1:1) FAB-MS m/z: 669 [M+H]

EXAMPLE 270 mp: 152°–157° C. Rf: 0.41 (CHCl$_3$:MeOH-:AcOH=16:1:1) FAB-MS m/z: 683 [M+H]

EXAMPLE 271 mp: 150°–153° C. Rf: 0.52 (CHCl$_3$:MeOH-:AcOH=16:1:1) FAB-MS m/z: 719 [M+H]

EXAMPLE 272 mp: 196°–199° C. Rf: 0.52 (CHCl$_3$:MeOH-:AcOH=16:1:1) FAB-MS m/z: 719 [M+H]

EXAMPLE 273 mp: 90°–100° C. Rf: 0.50 (CHCl$_3$:MeOH-:AcOH=16:1:1) FAB-MS m/z: 649 [M+H]

EXAMPLE 274 mp: 140°–148° C. Rf: 0.50 (CHCl$_3$:MeOH-:AcOH=16:1:1) FAB-MS m/z: 708 [M+H]

EXAMPLE 275 mp: 95°–105° C. Rf: 0.44 (CHCl$_3$:MeOH-:AcOH=16:1:1) FAB-MS m/z: 670 [M+H]

EXAMPLE 276 mp: 183°–185° C. Rf: 0.36 (CHCl$_3$:MeOH-:AcOH=16:1:1) FAB-MS m/z: 671 [M+H]

EXAMPLE 277
mp: 145°-150° C. Rf: 0.46 (CHCl3:MeOH:AcOH=16:1:1) FAB-MS m/z: 664 [M+H]

EXAMPLE 278
mp: 205°-207° C. Rf: 0.49 (CHCl3:MeOH:AcOH=16:1:1) FAB-MS m/z: 675 [M+H]

EXAMPLE 279
mp: 90°-130° C. Rf: 0.41 (CHCl3:MeOH:AcOH=8:1:1)

EXAMPLE 280
mp: 89°-120° C. Rf: 0.40 (CHCl3:MeOH:AcOH=16:1:1) FAB-MS m/z: 678 [M+H]

EXAMPLE 281
mp: 145°-150° C. Rf: 0.51 (CHCl3:MeOH:AcOH=16:1:1) FAB-MS m/z: 663 [M+H]

EXAMPLE 282
mp: 165°-170° C. Rf: 0.49 (CHCl3:MeOH:AcOH=16:1:1) FAB-MS m/z: 733 [M+H]

EXAMPLE 283
mp: 156°-160° C. Rf: 0.47 (CHCl3:MeOH:AcOH=16:1:1) FAB-MS m/z: 733 [M+H]

EXAMPLE 284
mp: 165°-200° C. Rf: 0.29 (CHCl3:MeOH:AcOH=16:1:1) FAB-MS m/z: 616 [M+H]

EXAMPLE 285
mp: 137°-142° C. Rf: 0.46 (CHCl3:MeOH:AcOH=16:1:1) FAB-MS m/z: 644 [M+H]

EXAMPLE 286
mp: 155°-157° C. Rf: 0.48 (CHCl3:MeOH:AcOH=16:1:1) FAB-MS m/z: 658 [M+H]

EXAMPLE 287
mp: 111°-128° C. Rf: 0.48 (CHCl3:MeOH:AcOH=16:1:1) FAB-MS m/z: 673 [M+H]

EXAMPLE 288
mp: 80°-108° C. Rf: 0.47 (CHCl3:MeOH:AcOH=16:1:1) FAB-MS m/z: 817 [M+K]

EXAMPLE 289
mp: 110°-113° C. Rf: 0.49 (CHCl3:MeOH:AcOH=16:1:1)

EXAMPLE 290
mp: 195° C. (dec.) Rf: 0.52 (CHCl3:MeOH:AcOH=16:1:1) FAB-MS m/z: 535 [M+H]

EXAMPLE 291
mp: 165°-169° C. Rf: 0.45 (CHCl3:MeOH:AcOH=16:1:1) FAB-MS m/z: 630 [M+H]

EXAMPLE 292
Rf: 0.32 (CHCl3:MeOH:AcOH=8:1:1)

EXAMPLE 293
Rf: 0.32 (CHCl3:MeOH:AcOH=8:1:1)

EXAMPLE 294
Rf: 0.68 (CHCl3:MeOH:AcOH=8:2:1)

EXAMPLE 295
mp: 188°-190° C. Rf: 0.31 (CHCl3:MeOH:AcOH=8:1:1)

EXAMPLE 296
mp: 202°-205° C. Rf: 0.29 (CHCl3:MeOH:AcOH=8:1:1)

EXAMPLE 297
Rf: 0.10 (CHCl3:MeOH:AcOH=8:1:1)

EXAMPLE 298
Rf: 0.07 (CHCl3:MeOH:AcOH=8:1:1)

EXAMPLE 299
Rf: 0.10 (CHCl3:MeOH:AcOH=8:1:1)

EXAMPLE 300
Rf: 0.09 (CHCl3:MeOH:AcOH=8:1:1)

EXAMPLE 301
Rf: 0.11 (CHCl3:MeOH:AcOH=8:1:1)

EXAMPLE 302
Rf: 0.25 (CHCl3MeOH:AcOH=8:1:1)

EXAMPLE 303
Rf: 0.22 (CHCl3:MeOH:AcOH=16:1:1)

EXAMPLE 304
Rf: 0.29 (CHCl3:MeOH:AcOH=8:1:1)

EXAMPLE 305
Rf: 0.33 (CHCl3:MeOH:AcOH=8:2:1)

EXAMPLE 306
Rf: 0.45 (CHCl3:MeOH:AcOH=8:2:1)

EXAMPLE 307
Rf: 0.29 (CHCl3:MeOH:AcOH=8:1:1)

EXAMPLE 308
Rf: 0.33 (CHCl3:MeOH:AcOH=8:2:1)

EXAMPLE 309
Rf: 0.53 (CHCl3:MeOH:AcOH=8:1:1)

EXAMPLE 310
Rf: 0.28 (CHCl3:MeOH:AcOH=8:2:1)

EXAMPLE 311
Rf: 0.25 (CHCl3:MeOH:AcOH=8:1:1)

EXAMPLE 312
Rf: 0.62 (CHCl3:MeOH:AcOH=8:2:1)

EXAMPLE 313
Rf: 0.64 (CHCl3:MeOH:AcOH=8:2:1)

EXAMPLE 314
Rf: 0.46 (CHCl3:MeOH:AcOH=8:2:1)

EXAMPLE 315
mp: 248° C. (dec.) Rf: 0.27 (CHCl$_3$:MeOH:AcOH=8:1:1)

EXAMPLE 316
Rf: 0.32 (CHCl$_3$:MeOH:AcOH=8:1:1)

EXAMPLE 317
mp: 142°–147° C. Rf: 0.34 (CHCl$_3$:MeOH:AcOH=8:1:1)

EXAMPLE 318
Rf: 0.31 (CHCl$_3$:MeOH:AcOH=8:1:1)

EXAMPLE 319
Rf: 0.37 (CHCl$_3$:MeOH:AcOH=8:1:1)

EXAMPLE 320
Rf: 0.37 (CHCl$_3$:MeOH:AcOH=8:1:1)

EXAMPLE 321
Rf: 0.20 (CHCl$_3$:MeOH:AcOH=8:2:1)

EXAMPLE 322
Rf: 0.32 (CHCl$_3$:MeOH:AcOH=8:1:1)

EXAMPLE 323
Rf: 0.36 (CHCl$_3$:MeOH:AcOH=8:1:1)

EXAMPLE 324
Rf: 0.36 (CHCl$_3$:MeOH:AcOH=8:1:1)

EXAMPLE 325
Rf: 0.36 (CHCl$_3$:MeOH:AcOH=8:1:1)

EXAMPLE 326
Rf: 0.54 (CHCl$_3$:MeOH:AcOH=8:2:1)

EXAMPLE 327
Rf: 0.54 (CHCl$_3$:MeOH:AcOH=8:2:1)

EXAMPLE 328
Rf: 0.53 (CHCl$_3$:MeOH:AcOH=8:2:1)

EXAMPLE 329
Rf: 0.53 (CHCl$_3$:MeOH:AcOH=8:2:1)

EXAMPLE 330
Rf: 0.53 (CHCl$_3$:MeOH:AcOH=8:2:1)

EXAMPLE 331
mp: 205°–208° C. Rf: 0.27 (CHCl$_3$:MeOH:AcOH=8:1:1)

EXAMPLE 332
mp: 200°–210° C. Rf: 0.34 (CHCl$_3$:MeOH:AcOH=8:1:1)

EXAMPLE 333
mp: 146°–150° C. Rf: 0.74 (CHCl$_3$:MeOH:AcOH=8:1:1)

EXAMPLE 334
mp: 138°–141° C. Rf: 0.70 (CHCl$_3$:MeOH:AcOH=8:1:1)

EXAMPLE 335
mp: 80°–90° C. Rf: 0.42 (CHCl$_3$:MeOH:AcOH=16:1:1) Rf: 0.72 (CHCl$_3$:MeOH:AcOH=8:1:1)

EXAMPLE 336
Rf: 0.61 (CHCl$_3$:MeOH:AcOH=16:1:1)

EXAMPLE 337
mp: 103°–110° C. Rf: 0.46 (CHCl$_3$:MeOH:AcOH=16:1:1)

EXAMPLE 338
mp: 128°–137° C. Rf: 0.47 (CHCl$_3$:MeOH:AcOH=8:1:1)

EXAMPLE 339
mp: 105°–115° C. Rf: 0.48 (CHCl$_3$:MeOH:AcOH=16:1:1)

EXAMPLE 340
mp: 133°–136° C. Rf: 0.47 (CHCl$_3$:MeOH:AcOH=8:1:1)

EXAMPLE 341
mp: 158°–162° C. Rf: 0.42 (CHCl$_3$:MeOH:AcOH=8:1:1)

EXAMPLE 342
Rf: 0.64 (CHCl$_3$:MeOH:AcOH=8:1:1)

EXAMPLE 343
Rf: 0.56 (CHCl$_3$:MeOH:AcOH=8:1:1)

EXAMPLE 344
Rf: 0.30 (CHCl$_3$:MeOH=9:1)

EXAMPLE 345
Rf: 0.41 (CHCl$_3$:MeOH:AcOH=8:2:1)

EXAMPLE 346
mp: 210°–212° C. Rf: 0.44 (CHCl$_3$:MeOH=9:1)

EXAMPLE 347
Rf: 0.50 (CHCl$_3$:MeOH:AcOH=8:2:1)

EXAMPLE 348
mp: 129°–135° C. Rf: 0.37 (CHCl$_3$:MeOH:AcOH=8:1:1)

EXAMPLE 349
mp: 91°–113° C. Rf: 0.53 (CHCl$_3$:MeOH:AcOH=16:1:1)

EXAMPLE 350
mp: 162°–167° C. Rf: 0.12 (CHCl$_3$:MeOH:AcOH=8:2:1)

EXAMPLE 351
mp: 133°–140° C. Rf: 0.52 (CHCl$_3$:MeOH:AcOH=8:1:1)

EXAMPLE 352
mp: 208°–210° C. Rf: 0.72 (CHCl$_3$:MeOH:AcOH=8:1:1)

EXAMPLE 353 mp: 113°-123° C. Rf: 0.72 (CHCl₃:MeOH:AcOH=8:1:1)

EXAMPLE 354 mp: 160°-164° C. Rf: 0.80 (CHCl₃:MeOH:AcOH=8:1:1)

EXAMPLE 355

Rf: 0.30 (CHCl₃:MeOH:AcOH=8:1:1)

The object compounds in Examples 356 to 374, 376 to 377, 380 to 382, 384 to 392 and 400 could be obtained by reacting the corresponding carboxylic acid compounds (I-i) with substituted amines in a similar manner to that of Example 1-1).

The object compounds in Examples 375, 378 to 379, and 393 to 399 could be obtained by reacting the corresponding carboxylic acid or its ethyl ester compounds (I-i) with optionally substituted amines in a similar manner to that of Example 383.

EXAMPLE 383

N-(Hexahydro-1H-azepin-1-ylcarbonyl)-L-Leu-D-Trp(Me)-D-Pya-OEt (0.20 g) was dissolved in 2.4N ammonia in methanol (10 ml) and the mixture was allowed to stand for 3 days at room temperature. Then the mixture was concentrated in vacuo and the residue was triturated with diethyl ether (10 ml) to give the object compound (0.18 g).

EXAMPLE 401

N-(Hexahydro-1H-azepin-1-ylcarbonyl)-L-Leu-D-Trp(Me)-D-Pya-2-[(5S)-5-ethoxycarbonyl-2-oxopyrrolidin-1-yl]ethylamide (70 mg) and 2.4N NH₃ in MeOH (5 ml) were reacted in a similar manner to that of Example 383 to give the object compound (42.7 mg).

The physico-chemical properties of the object compounds of Examples 356 to 401 are provided hereinbelow.

EXAMPLE 356 mp: 220°-224° C. RF: 0.47 (CHCl₃:MeOH=9:1)

EXAMPLE 357 mp: 196°-203° C. Rf: 0.36 (CHCl₃:MeOH=9:1)

EXAMPLE 358

Rf: 0.62 (CHCl₃:MeOH=9:1)

EXAMPLE 359 mp: 140°-145° C. Rf: 0.52 (CHCl₃:MeOH=9:1)

EXAMPLE 360

Rf: 0.56 (CHCl₃:MeOH=9:1)

EXAMPLE 361

Rf: 0.60 (CHCl₃:MeOH=9:1)

EXAMPLE 362

Rf: 0.60 (CHCl₃:MeOH=9:1)

EXAMPLE 363

Rf: 0.58 (CHCl₃:MeOH=9:1)

EXAMPLE 364

Rf: 0.58 (CHCl₃:MeOH=9:1)

EXAMPLE 365

Rf: 0.53 (CHCl₃:MeOH=9:1)

EXAMPLE 366

Rf: 0.53 (CHCl₃:MeOH=9:1)

EXAMPLE 367

Rf: 0.52 (CHCl₃:MeOH=9:1)

EXAMPLE 368

Rf: 0.83 (CHCl₃:MeOH:AcOH=8:2:1)

EXAMPLE 369

Rf: 0.83 (CHCl₃:MeOH:AcOH=8:2:1)

EXAMPLE 370

Rf: 0.83 (CHCl₃:MeOH:AcOH=8:2:1)

EXAMPLE 371

Rf: 0.83 (CHCl₃:MeOH:AcOH=8:2:1)

EXAMPLE 372

Rf: 0.83 (CHCl₃:MeOH:AcOH=8:2:1)

EXAMPLE 373 mp: 190°-195° C. Rf: 0.72 (CHCl₃:MeOH=9:1)

EXAMPLE 374 mp: 195°-197° C. Rf: 0.76 (CHCl₃:MeOH=9:1)

EXAMPLE 375

Rf: 0.41 (CHCl₃:MeOH=9:1)

EXAMPLE 376

Rf: 0.44 (CHCl₃:MeOH=9:1)

EXAMPLE 377 mp: 160°-164° C. Rf: 0.49 (CHCl₃:MeOH=9:1)

EXAMPLE 378

Rf: 0.44 (CHCl₃:MeOH=9:1)

EXAMPLE 379 mp: 200°-203° C. Rf: 0.51 (CHCl₃:MeOH=9:1)

EXAMPLE 380 mp: 76°-78° C. Rf: 0.54 (CHCl₃:MeOH=9:1)

EXAMPLE 381 mp: 75°-78° C. Rf: 0.49 (CHCl₃:MeOH=9:1)

EXAMPLE 382

Rf: 0.64 (CHCl₃:MeOH=9:1)

EXAMPLE 383 mp: 110°-112° C. Rf: 0.50 (CHCl₃:MeOH=9:1)

EXAMPLE 384 mp: 140°-145° C. Rf: 0.64 (CHCl₃:MeOH=9:1)

EXAMPLE 385

Rf: 0.65 (CHCl₃:MeOH=9:1)

EXAMPLE 386

Rf: 0.62 (CHCl₃:MeOH=9:1)

EXAMPLE 387

Rf: 0.62 (CHCl₃:MeOH=9:1)

EXAMPLE 388

Rf: 0.62 (CHCl₃:MeOH=9:1)

EXAMPLE 389

Rf: 0.65 (CHCl₃:MeOH=9:1)

EXAMPLE 390

Rf: 0.45 (CHCl₃:MeOH=9:1)

EXAMPLE 391 mp: 165°-167° C. Rf: 0.48 (CHCl₃:MeOH=9:1)

EXAMPLE 392 mp: 142°-143° C. Rf: 0.50 (CHCl₃:MeOH=9:1)

EXAMPLE 393 mp: 168° C. Rf: 0.46 (CHCl₃:MeOH=9:1)

EXAMPLE 394 mp: 120°-125° C. Rf: 0.47 (CHCl₃:MeOH=9:1)

EXAMPLE 395 mp: 115°-125° C. Rf: 0.47 (CHCl₃:MeOH=9:1)

EXAMPLE 396 mp: 168° C. Rf: 0.41 (CHCl₃:MeOH=9:1)

EXAMPLE 397 mp: 215° C. Rf: 0.35 (CHCl₃:MeOH=9:1)

EXAMPLE 398 mp: 108°-109° C. Rf: 0.34 (CHCl₃:MeOH=19:1)

EXAMPLE 399 mp: 119°-120° C. Rf: 0.28 (CHCl₃:MeOH=19:1)

EXAMPLE 400

Rf: 0.49 (CHCl₃:MeOH=9:1)

EXAMPLE 401 mp: 195°-197° C. Rf: 0.26 (CHCl₃:MeOH=9:1)

EXAMPLE 402

N-(Hexahydro-1H-azepin-1-ylcarbonyl)-L-Leu-D-Trp(Me)-OH (400 mg), N-(ethoxycarbonylmethyl)-N-(pyridin-2-ylmethyl)amine (187 mg), HOBT (131 mg), WSLD-HCl (150 mg) and DMF (5 ml) were reacted in a similar manner to that of Example 1-1) to give the object compound (554 mg).

Rf: 0.37 (CHCl₃:MeOH=20:1)

EXAMPLE 403

N-(Hexahydro-1H-azepin-1-ylcarbonyl)-L-Leu-D-Trp(Me)-OH (400 mg), N-(ethoxycarbonylmethyl)-N-[2-(pyridin-2-yl)ethyl]amine dihydrochloride (271 mg), HOBT (131 mg), WSCD (150 mg), N-methylmorpholine (98 mg) and DMF (5 ml) were reacted in substantially the same manner to that of Example 92 to give the object compound (288 mg).

Rf: 0.32 (CHCl₃:MeOH=20:1)

EXAMPLE 404

Cyclohexyl isocyanate (60 mg), 2HCl.H-D-alloIle-L-Leu-D-Trp(Me)-D-Pya-OEt (300 mg), Et₃N (87 mg) and DMF (10 ml) were reacted in a similar manner to that of Example 4-1) to give the object compound (260 mg).

mp: 235°-237° C. Rf: 0.45 (CHCl₃:MeOH=9:1)

EXAMPLE 405

The object compound was obtained in 90.8% yield in substantially the same manner as that of Example 406.

mp: 111°-115° C. Rf: 0.46 (CHCl₃:MeOH=9:1)

EXAMPLE 406

Boc-L-Leu-D-Trp(CH₃)-D-Pya-OC₂H₅ (1.70 g) in TFA (20 ml) and anisole (2 ml) was reacted at 0° C. for 1 hour and then the product was reacted with 4N HCl in 1,4-dioxane in a similar manner to that of Preparation 1-2) to give the object compound (1.60 g).

mp: 141°-145° C. Rf: (CHCl₃:MeOH=9:1)

The object compounds in Examples 407 to 416 could be obtained by removing t-butoxycarbonyl groups from the corresponding starting compounds (I-b) with TFA and anisole in a similar manner to that of Preparation 1-2).

The physico-chemical properties of these object compounds are provided hereinbelow.

EXAMPLE 407 mp: 146°-156° C. Rf: 0.35 (CHCl₃:MeOH=9:1)

EXAMPLE 408

Rf: 0.26 (CHCl₃:MeOH=9:1)

EXAMPLE 409

Rf: 0.26 (CHCl₃:MeOH=9:1)

EXAMPLE 410 mp: 86°-103° C. Rf: 0.36 (CHCl₃:MeOH=9:1)

EXAMPLE 411 mp: 76°-102° C. Rf: 0.20 (CHCl₃:MeOH:AcOH=16:1:1)

EXAMPLE 412 mp: 152°-165° C. Rf: 0.32 (CHCl₃:MeOH=9:1)

EXAMPLE 413

Rf: 0.27 (CHCl₃:MeOH=9:1)

EXAMPLE 414

Rf: 0.26 (CHCl₃:MeOH=9:1)

EXAMPLE 415 mp: 194°-202° C. Rf: 0.26 (CHCl₃:MeOH=9:1)

EXAMPLE 416

Rf: 0.26 (CHCl₃:MeOH=9:1)

The object compounds in Examples 417 to 426 could be obtained by reacting the corresponding starting compounds with 4N hydrogen chloride in ethyl acetate in a similar manner to that of Example 22.

The physico-chemical properties of these object compounds are provided hereinbelow.

EXAMPLE 417 mp: 141°-146° C. Rf: 0.87 (CHCl₃:MeOH:AcOH=8:1:1) FAB-MS m/z=678 [M+H]

EXAMPLE 418 mp: 103°-120° C.

EXAMPLE 419
Rf: 0.41 (CHCl₃:MeOH=9:1)

EXAMPLE 420
Rf: 0.44 (CHCl₃MeOH=9:1)

EXAMPLE 421
Rf: 0.49 (CHCl₃MeOH=9:1)

EXAMPLE 422
Rf: 0.44 (CHCl₃MeOH=9:1)

EXAMPLE 423
Rf: 0.51 (CHCl₃:MeOH=9:1)

EXAMPLE 424
Rf: 0.65 (CHCl₃:MeOH=9:1)

EXAMPLE 425
mp: 110°-135° C. Rf: 0.50 (CHCl₃:MeOH=9:1)

EXAMPLE 426
mp: 105°-145° C. Rf: 0.49 (CHCl₃:MeOH=9:1)

The compounds of Examples 427 to 429 could be obtained by reacting the corresponding starting compounds (II) and (III) in a similar manner to that of Example 1-1).

The physicochemical properties of these object compounds are provided hereinbelow.

EXAMPLE 427
Rf: 0.44 (CHCl₃:MeOH=9:1)

EXAMPLE 428
Rf: 0.44 (CHCl₃:MeOH=9:1)

EXAMPLE 429
mp: 110°-112° C. Rf: 0.50 (CHCl₃:MeOH=9:1)

The compounds of Examples 430 to 432 could be obtained by reacting the corresponding starting compounds (V) and (VI) in a similar manner to that of Example 92.

The physicochemical properties of these object compounds are provided hereinbelow.

EXAMPLE 430
Rf: 0.44 (CHCl₃:MeOH=9:1)

EXAMPLE 431
Rf: 0.44 (CHCl₃:MeOH=9:1)

EXAMPLE 432
mp: 110°-112° C. Rf: 0.50 (CHCl₃:MeOH=9:1)

EXAMPLE 433
N-[N-{(1S)-1-Dimethylcarbamoyl-2-methylpropyl} carbamoyl]-L-Leu-D-Trp(CH₃)-D-Pya-OEt was obtained in substantially the same manner as that of Preparation 1-1).

Rf: 0.62 (10% MeoH in CHCl₃)

EXAMPLE 434
N-[N-{(1S)-1-Dimethylcarbamoyl-2-methylpropyl} carbamoyl]-L-Leu-D-Trp(CH₃)-D-Pya-ONa was obtained in substantially the same manner as that of Example 1-2).

The object compounds obtained in the above Examples are given in the following Table.

| Example Nos. | Chemical Formulae |
|---|---|
| 1-1) | 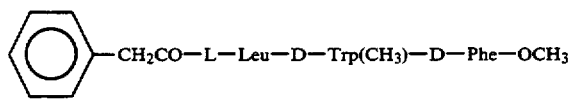 |
| 2) | 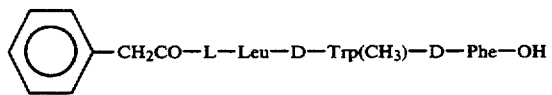 |
| 2-1) | 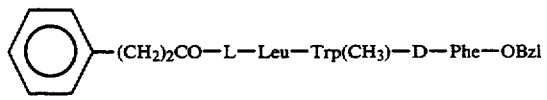 |
| 2) | 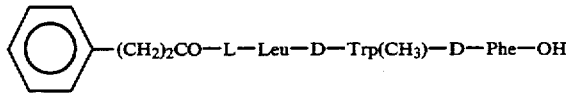 |
| 3-1) | 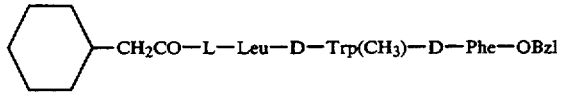 |
| 2) | 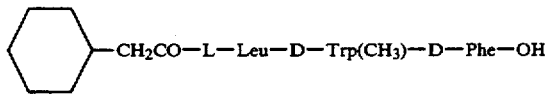 |

-continued 4-1) Ph-NHCO—L—Leu—D—Trp(CH₃)—D—Phe—OBzl 4-2) Ph-NHCO—L—Leu—D—Trp(CH₃)—D—Phe—OH 5-1) Cy-NHCO—L—Leu—D—Trp(CH₃)—D—Phe—OBzl 2) Cy-NHCO—L—Leu—D—Trp(CH₃)—D—Phe—OH 6-1) Ph-CH₂CO—L—Leu—D—Trp(CH₃)—D—Pya—OC₂H₅·HCl 2) Ph-CH₂CO—L—Leu—D—Trp(CH₃)—D—Pya—OH·HCl 7-1) Cy-NHCO—L—Leu—D—Trp(CH₃)—D—Pya—OC₂H₅

2) 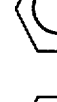Cy-NHCO—L—Leu—D—Trp(CH₃)—D—Pya—OH·HCl 8-1) Ph-CH₂CO—L—Leu—D—Trp(CH₃)—L—Phe—OC₂H₅

2) 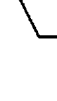Ph-CH₂CO—L—Leu—D—Trp(CH₃)—L—Phe—OH

9 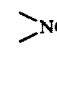Cy-NHCO—L—Leu—D—Trp(CH₃)—D—Pya—ONa

10 —NHCO—L—Leu—D—Trp(CH₃)—D—Pya—OC₂H₅

11 —NHCOO—CO—D—Trp(CH₃)—D—Pya—OC₂H₅

-continued
12 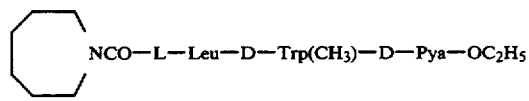
13 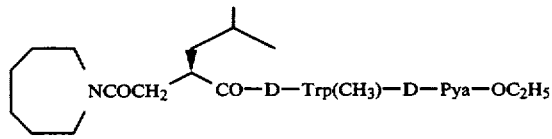
14 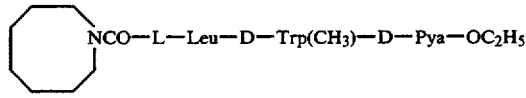
15 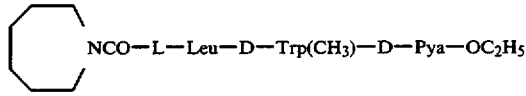
16 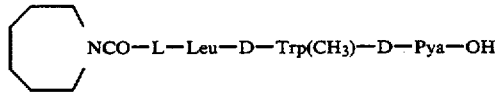
17 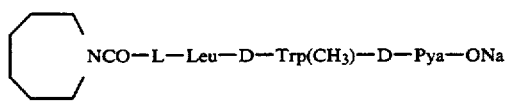
18 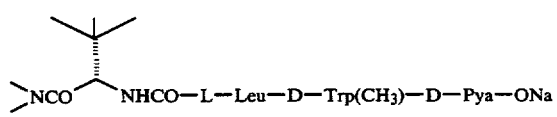
19 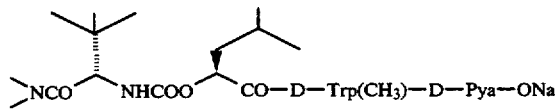
20 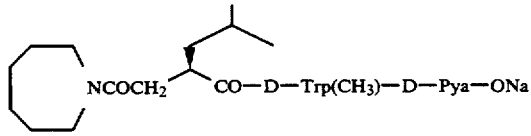
21 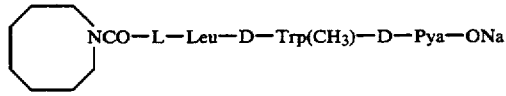
22 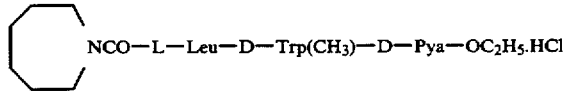
23 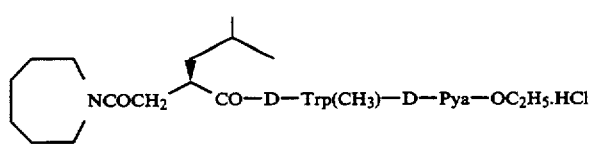

-continued
24 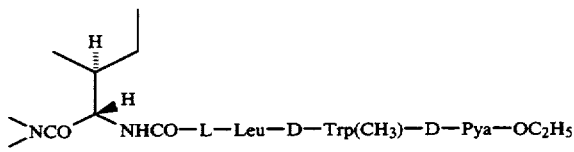
25 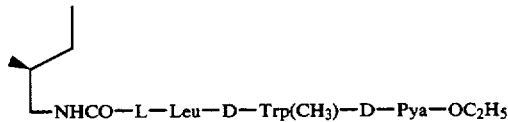
26 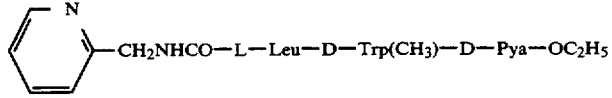
27 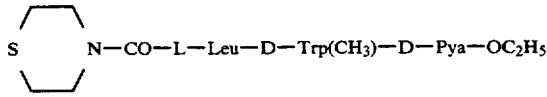
28 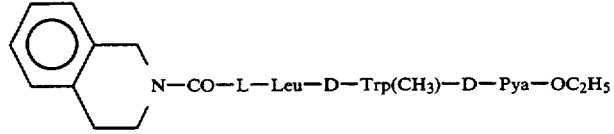
29 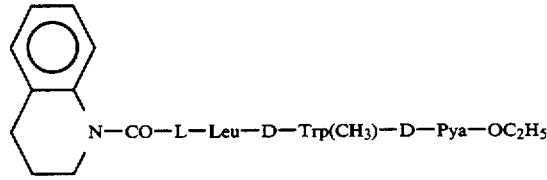
30 (n-C$_4$H$_9$)$_2$N—CO—L—Leu—D—Trp(CH$_3$)—D—Pya—OC$_2$H$_5$
31 (n-C$_3$H$_7$)$_2$N—CO—L—Leu—D—Trp(CH$_3$)—D—Pya—OC$_2$H$_5$
32 n-C$_7$H$_{15}$—NHCO—L—Leu—D—Trp(CH$_3$)—D—Pya—OC$_2$H$_5$
33 (i-C$_4$H$_9$)$_2$N—CO—L—Leu—D—Trp(CH$_3$)—D—Pya—OC$_2$H$_5$
34 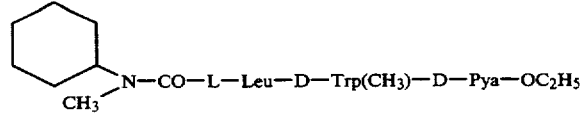
35 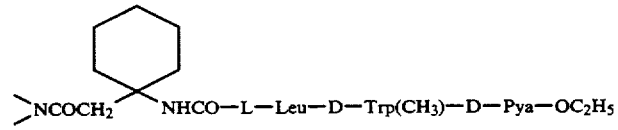
36 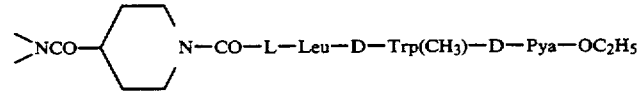
37 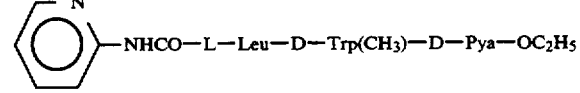

-continued
| 38 | 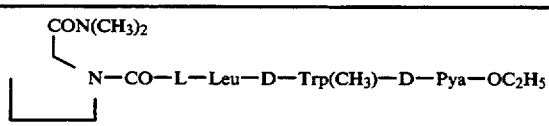 |
| 39 | 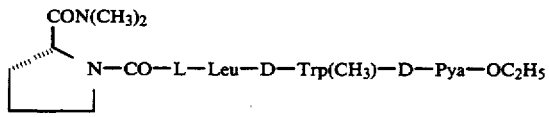 |
| 40 | 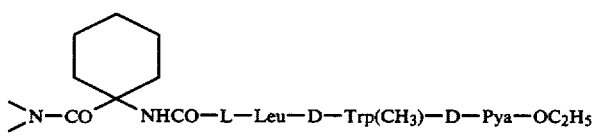 |
| 41 | 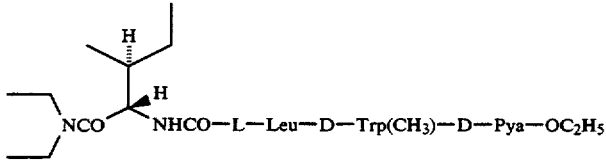 |
| 42 | 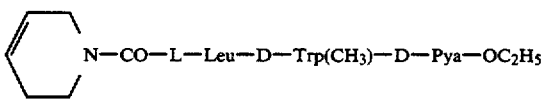 |
| 43 | 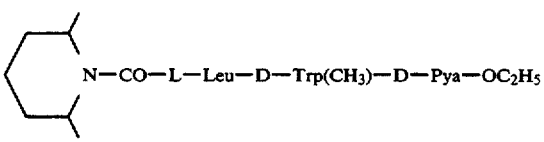 |
| 44 | 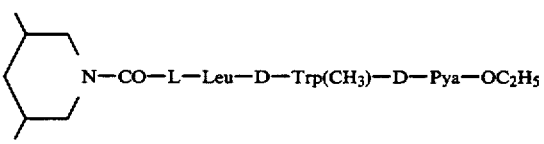 |
| 45 | 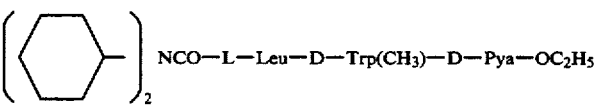 |
| 46 | $(C_2H_5)_2NCO-L-Leu-D-Trp(CH_3)-D-Pya-OC_2H_5$ |
| 47 | $(i-C_3H_7)_2NCO-L-Leu-D-Trp(CH_3)-D-Pya-OC_2H_5$ |
| 48 |  |
| 49 | 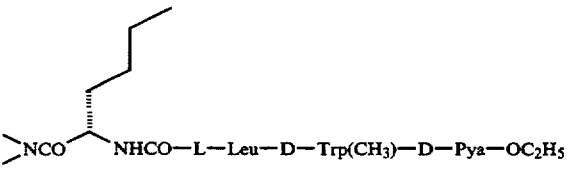 |

-continued
50
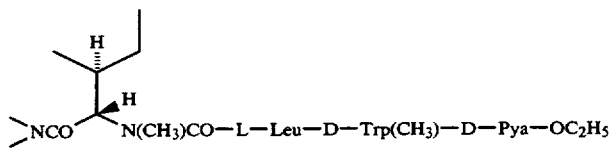
51
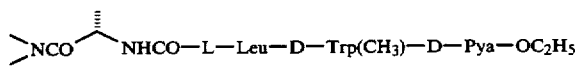
52
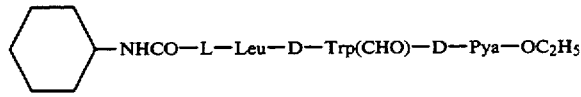
53
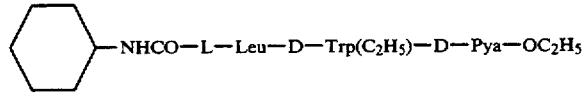
54
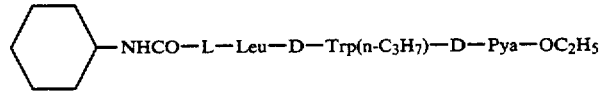
55
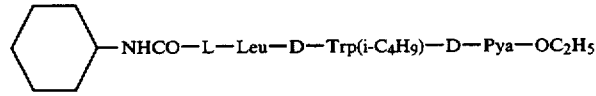
56
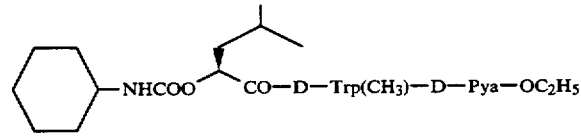
57
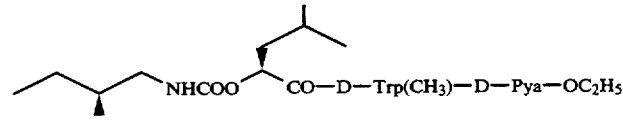
58
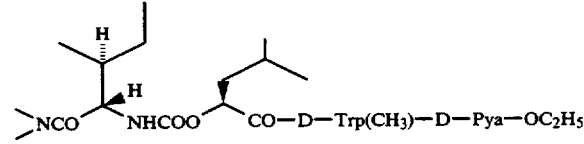
59
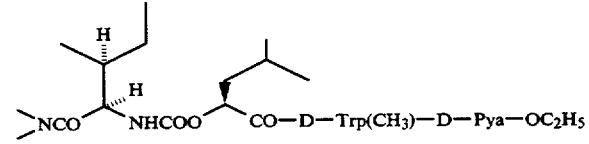
60
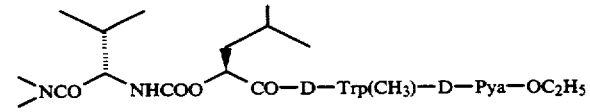

-continued
61 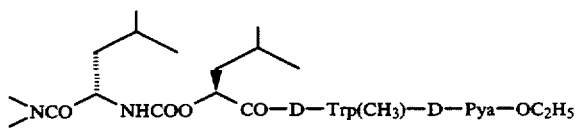
62 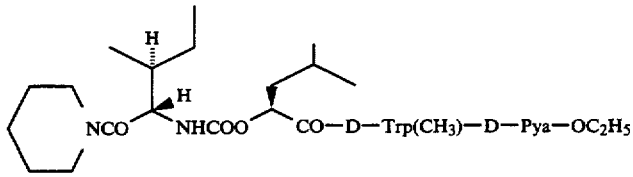
63 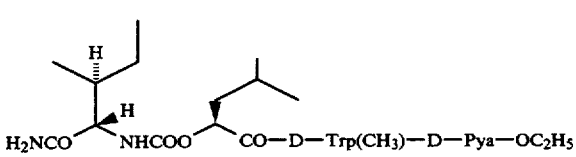
64 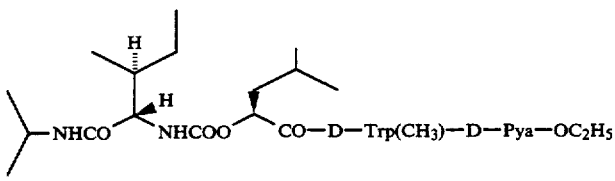
65 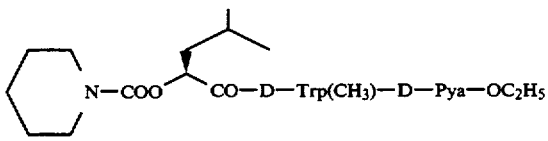
66 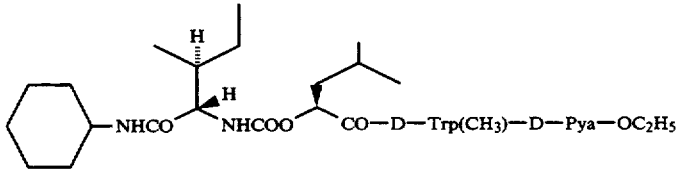
67 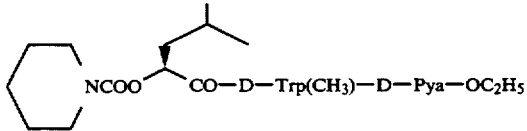
68 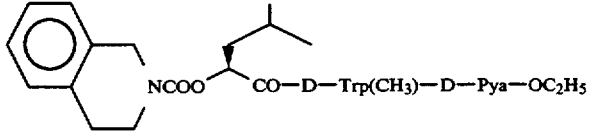
69 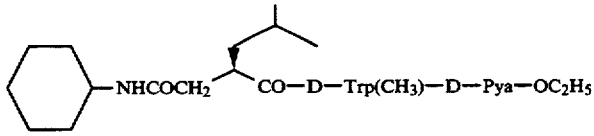

-continued
70 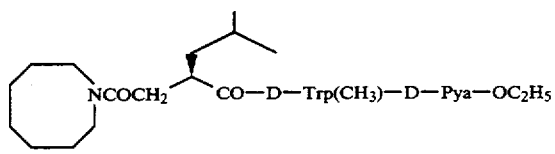
71 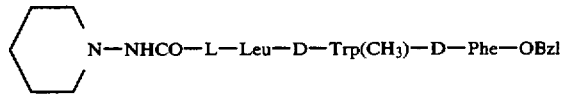
72 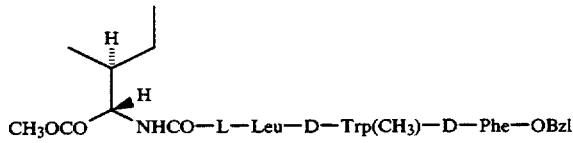
73 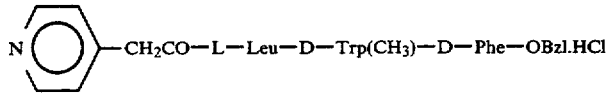
74 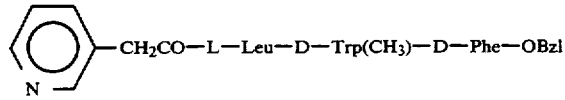
75 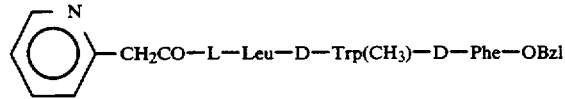
76 
77 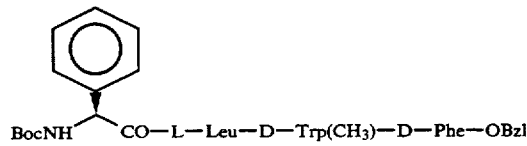
78 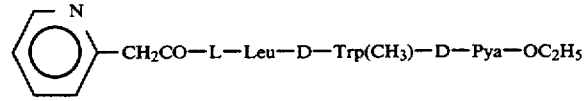
79 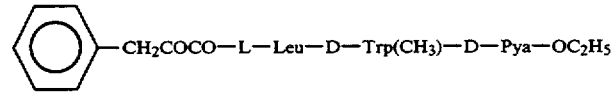
80 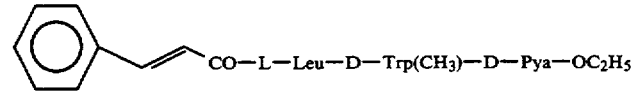
81 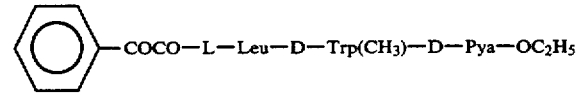

-continued
82 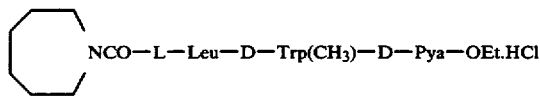NCO—L—Leu—D—Trp(CH₃)—D—Pya—OEt.HCl
83 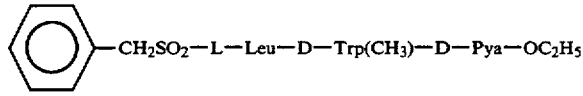—CH₂SO₂—L—Leu—D—Trp(CH₃)—D—Pya—OC₂H₅
84 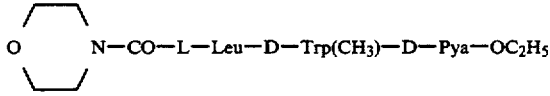N—CO—L—Leu—D—Trp(CH₃)—D—Pya—OC₂H₅
85 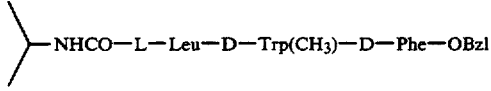—NHCO—L—Leu—D—Trp(CH₃)—D—Phe—OBzl
86 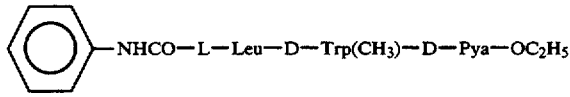—NHCO—L—Leu—D—Trp(CH₃)—D—Pya—OC₂H₅
87 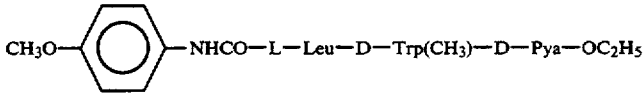—NHCO—L—Leu—D—Trp(CH₃)—D—Pya—OC₂H₅
88 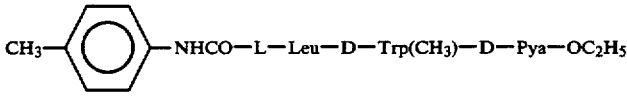—NHCO—L—Leu—D—Trp(CH₃)—D—Pya—OC₂H₅
89 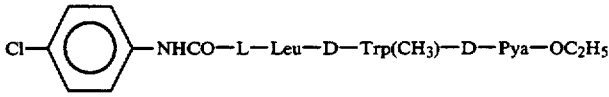—NHCO—L—Leu—D—Trp(CH₃)—D—Pya—OC₂H₅
90 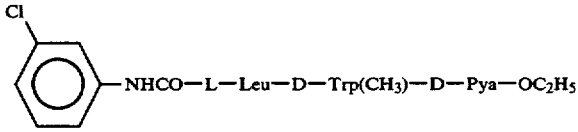—NHCO—L—Leu—D—Trp(CH₃)—D—Pya—OC₂H₅
91 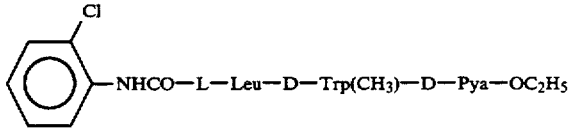—NHCO—L—Leu—D—Trp(CH₃)—D—Pya—OC₂H₅
92 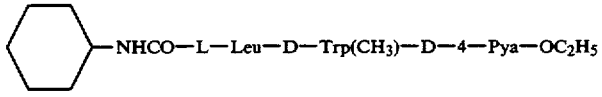—NHCO—L—Leu—D—Trp(CH₃)—D—4—Pya—OC₂H₅
93 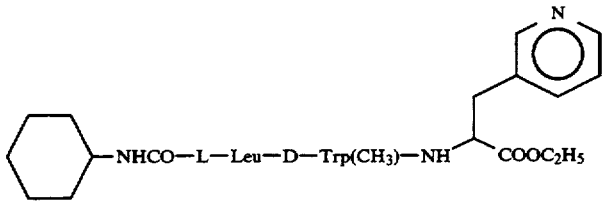—NHCO—L—Leu—D—Trp(CH₃)—NH -continued
| | |
|---|---|
| 94 | 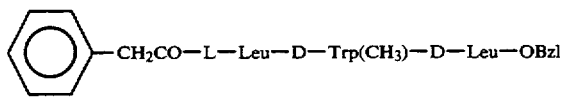—CH₂CO—L—Leu—D—Trp(CH₃)—D—Leu—OBzl |
| 95 | 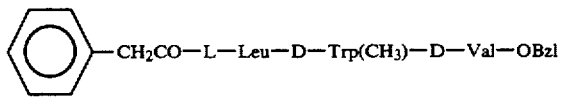—CH₂CO—L—Leu—D—Trp(CH₃)—D—Val—OBzl |
| 96 | 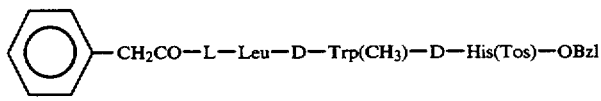—CH₂CO—L—Leu—D—Trp(CH₃)—D—His(Tos)—OBzl |
| 97 | 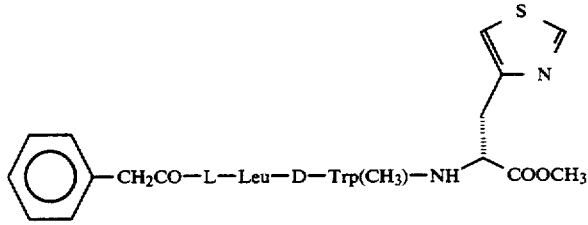 |
| 98 | Boc—D—alloIle—L—Leu—D—Trp(CHO)—D—Phe—OPac |
| 99 | 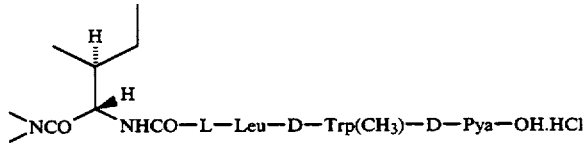 |
| 100 | 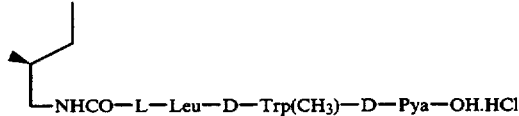 |
| 101 | 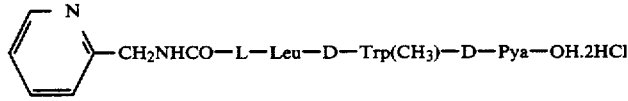 |
| 102 | 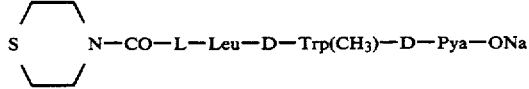 |
| 103 | 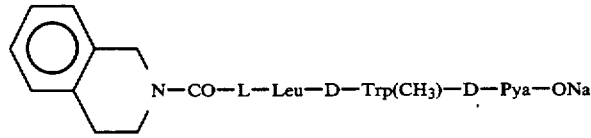 |
| 104 | 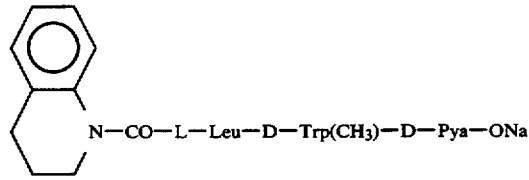 |
| 105 | (n-C₄H₉)₂N—CO—L—Leu—D—Trp(CH₃)—D—Pya—ONa |
| 106 | (n-C₃H₇)₂N—CO—L—Leu—D—Trp(CH₃)—D—Pya—ONa |
| 107 | n-C₇H₁₅—NHCO—L—Leu—D—Trp(CH₃)—D—Pya—ONa |
| 108 | (i-C₄H₉)₂N—CO—L—Leu—D—Trp(CH₃)—D—Pya—ONa |

-continued

109: Ph(N-CH₃)—CO—L—Leu—D—Trp(CH₃)—D—Pya—ONa

110: (CH₃)₂NCOCH₂—[cyclohexyl]—NHCO—L—Leu—D—Trp(CH₃)—D—Pya—ONa

111: (CH₃)₂NCO—[piperidin-4-yl]—N—CO—L—Leu—D—Trp(CH₃)—D—Pya—ONa

112: 2-Pyridyl—NHCO—L—Leu—D—Trp(CH₃)—D—Pya—OH·2HCl

113: CH₂CON(CH₃)₂ substituted pyrrolidin-N—CO—L—Leu—D—Trp(CH₃)—D—Pya—ONa

114: CON(CH₃)₂ substituted pyrrolidin-N—CO—L—Leu—D—Trp(CH₃)—D—Pya—ONa

115: (CH₃)₂N—CO—[cyclohexyl]—NHCO—L—Leu—D—Trp(CH₃)—D—Pya—ONa

116: (C₂H₅)₂NCO—CH(sec-Bu)—NHCO—L—Leu—D—Trp(CH₃)—D—Pya—ONa

117: tetrahydropyridin-N—CO—L—Leu—D—Trp(CH₃)—D—Pya—ONa

118: 2,6-dimethylpiperidin-N—CO—L—Leu—D—Trp(CH₃)—D—Pya—ONa

119: 2,4,6-trimethylpiperidin-N—CO—L—Leu—D—Trp(CH₃)—D—Pya—ONa

120 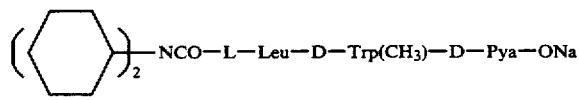
121 $(C_2H_5)_2NCO-L-Leu-D-Trp(CH_3)-D-Pya-ONa$
122 $(i-C_3H_7)_2NCO-L-Leu-D-Trp(CH_3)-D-Pya-ONa$
123 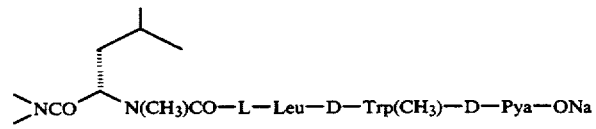
124 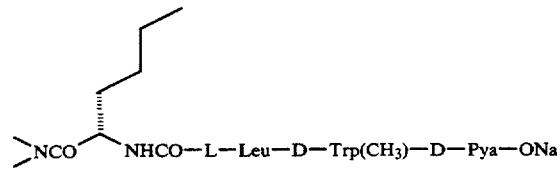
125 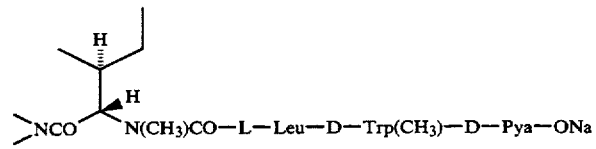
126 
127 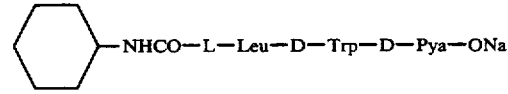
128 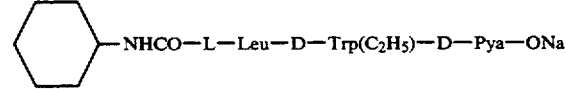
129 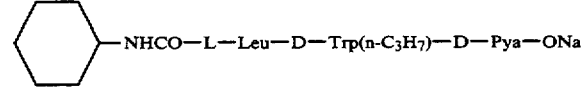
130 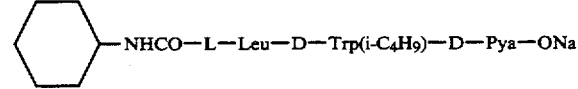
131 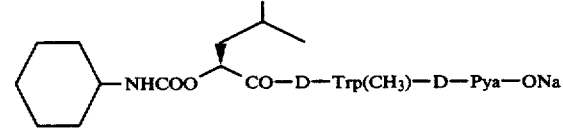
132 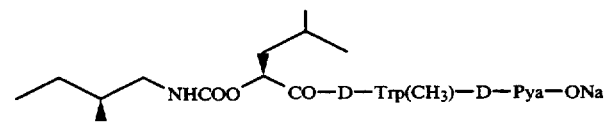

133 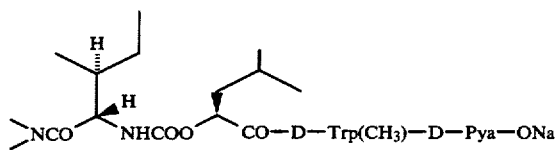
134 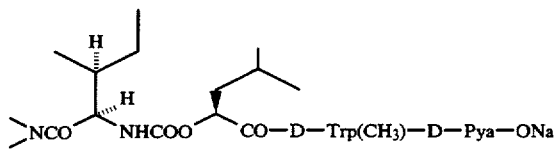
135 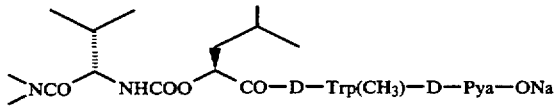
136 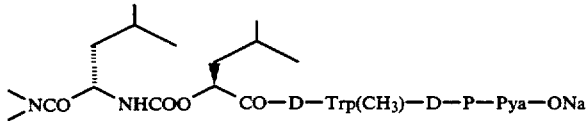
137 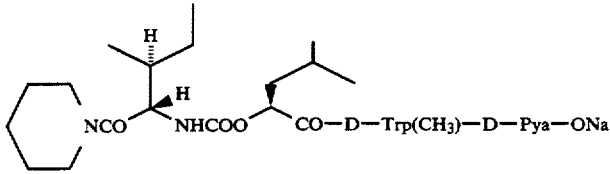
138 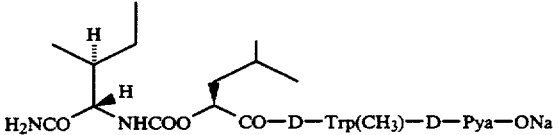
139 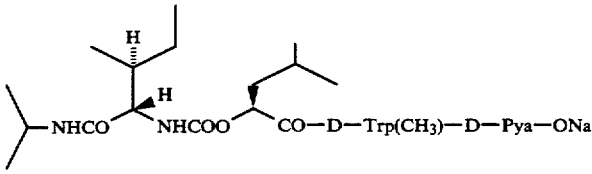
140 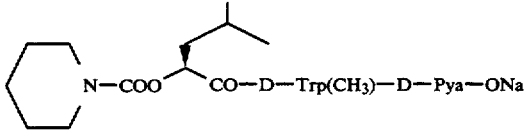
141 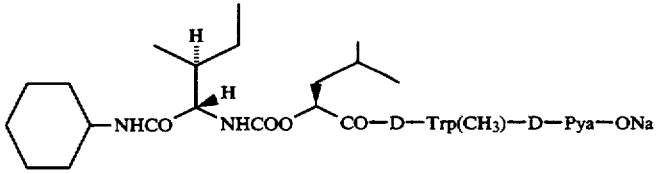

142 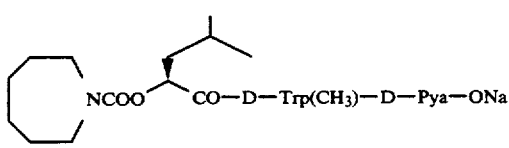
143 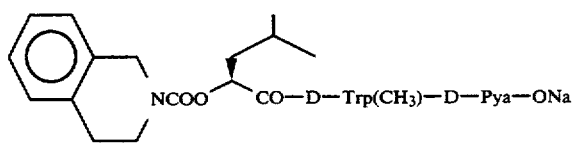
144 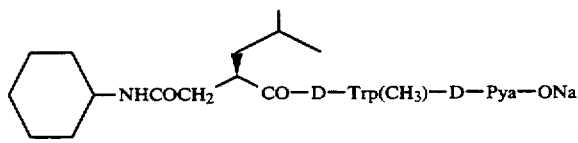
145 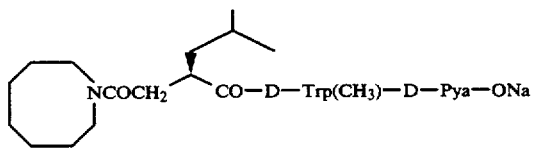
146 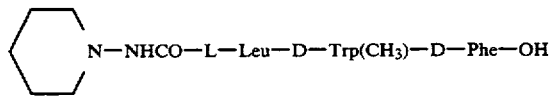
147 
148 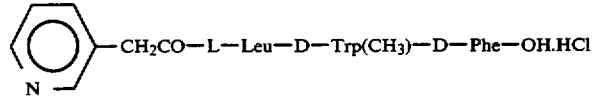
149 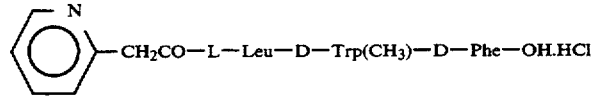
150 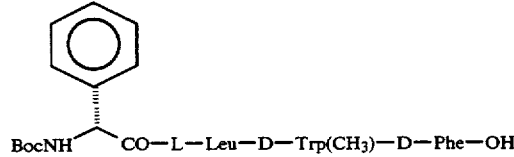
151 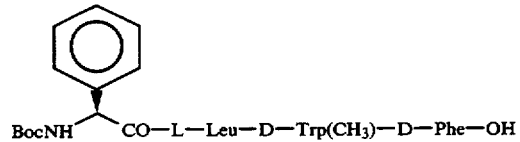
152 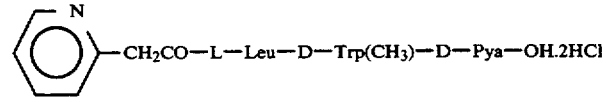

-continued
153 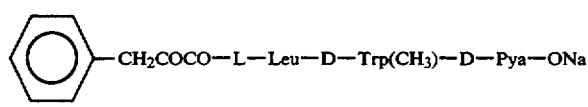
154 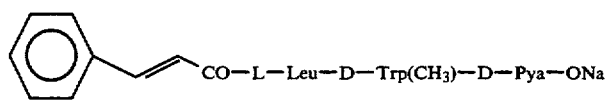
155 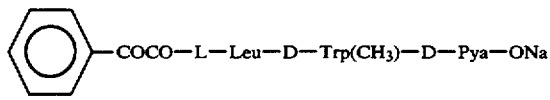
156 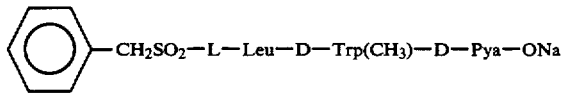
157 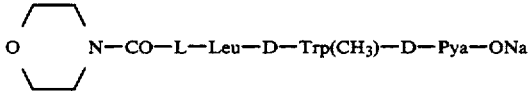
158 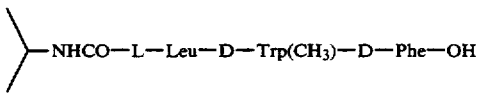
159 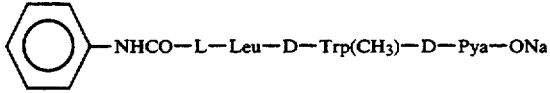
160 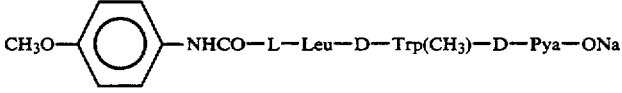
161 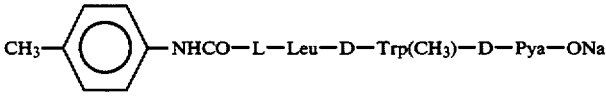
162 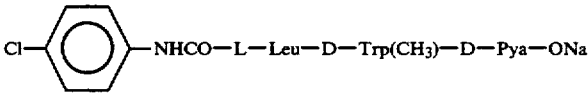
163 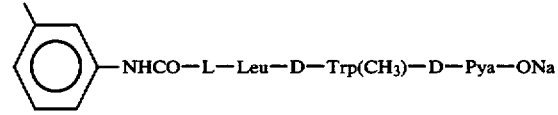
164 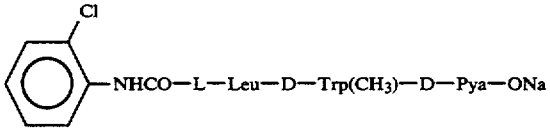
165 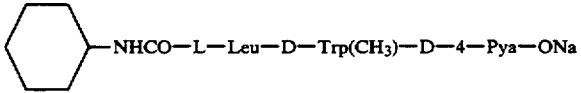

166 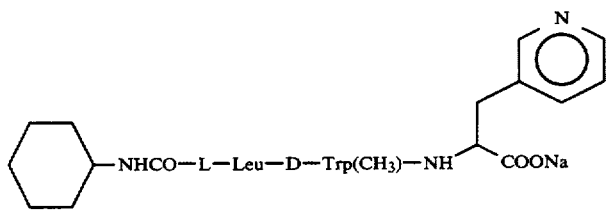
167 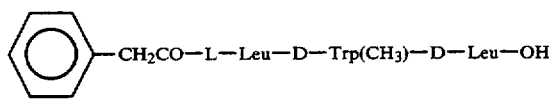
168 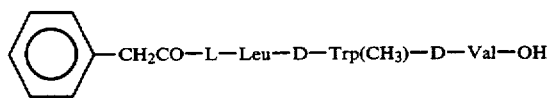
169 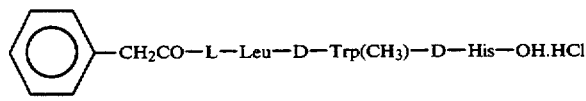
170 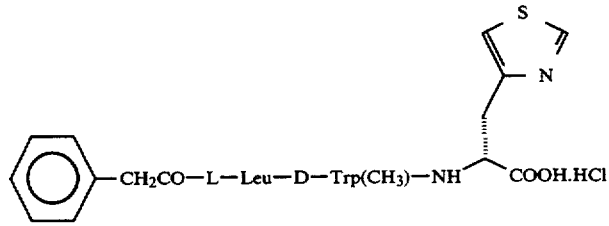
171 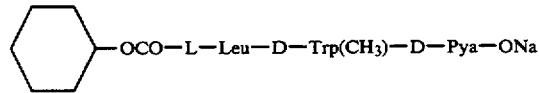
172 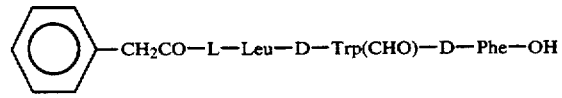
173 Boc—D—alloIle—L—Leu—D—Trp(CHO)—D—Phe—OH
174 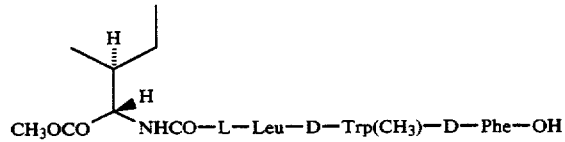
175 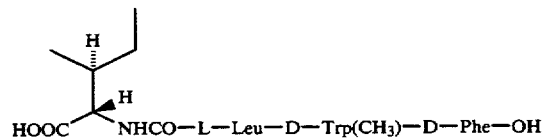
176 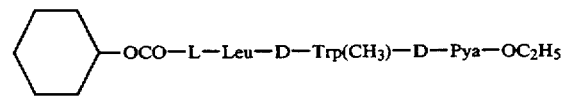
177 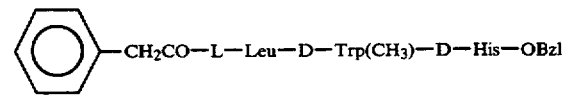

178 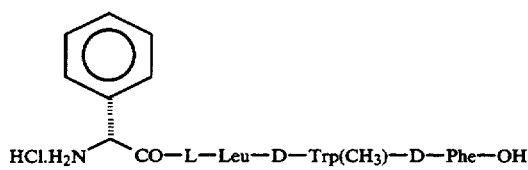
179 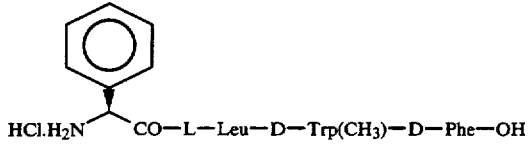
180 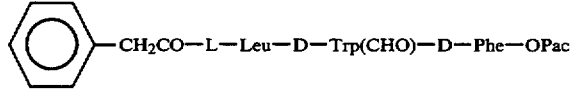
181 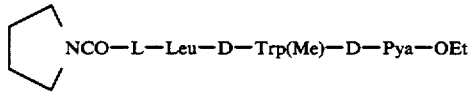
182 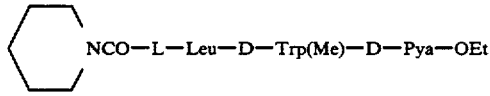
183 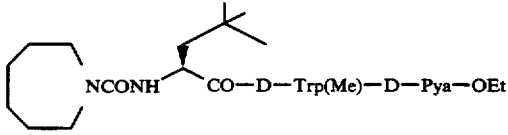
184 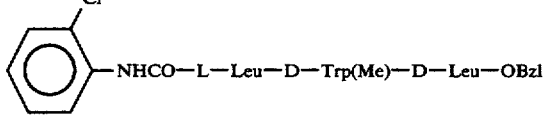
185 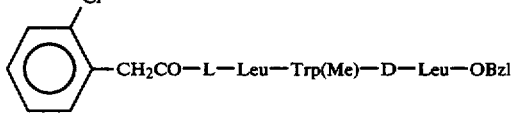
186 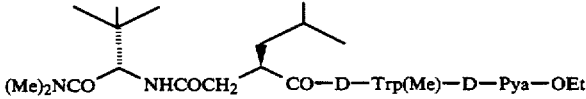
187 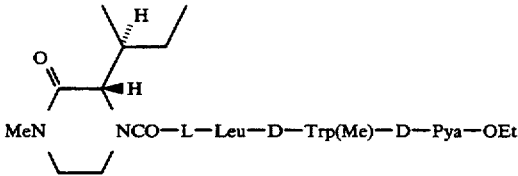
188 

189 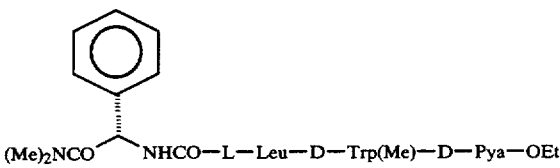
190 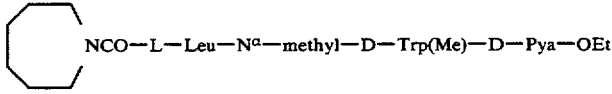
191 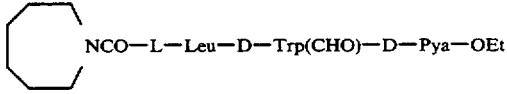
192 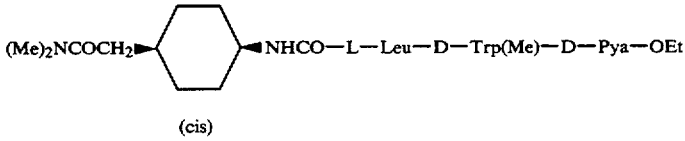
(cis)
193 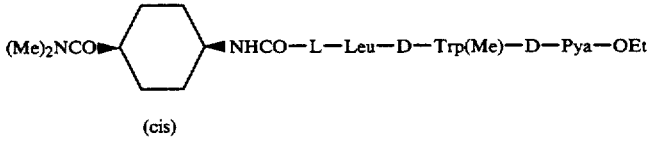
(cis)
194 (Me)₂NCOCH₂NHCO—L—Leu—D—Trp(Me)—D—Pya—OEt
195 (Me)₂NCO(CH₂)₂NHCO—L—Leu—D—Trp(Me)—D—Pya—OEt
196 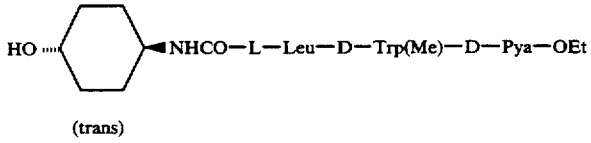
(trans)
197 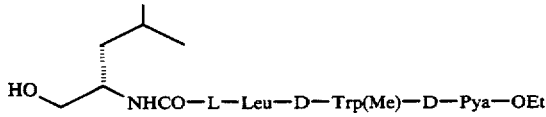
198 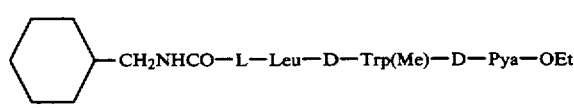
199 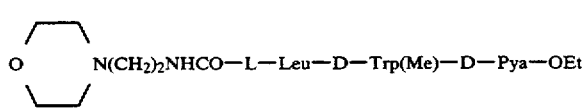
200 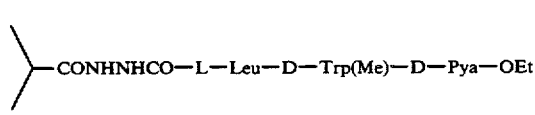
201 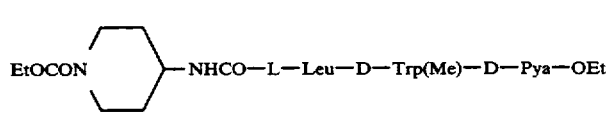

202 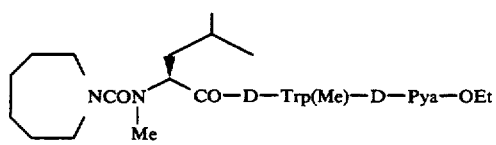
203 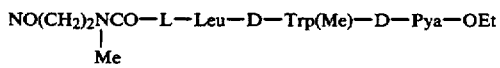
204 Boc—L—Ile—D—Trp(CHO)—βAla—OMe
205 Boc—L—Nle—D—Trp(CHO)—βAla—OMe
206 Boc—D—Leu—D—Trp(CHO)—βAla—OMe
207 Boc—L—Leu—D—Trp(CHO)—D—Glu(OBzl)—OPac
208 Boc—L—Leu—D—Trp(CHO)—βAla—OPac
209 Boc—L—Leu—D—Trp(Me)—D—Phe—OBzl
210 Boc—L—His(Tos)—D—Trp(CHO)—βAla—OMe
211 Boc—L—Pya—D—Trp(CHO)—βAla—OMe
212 Boc—L—Phe—D—Trp(CHO)—βAla—OMe
213 Boc—L—Cha—D—Trp(CHO)—βAla—OMe
214 Boc—L—1—Nal—D—Trp(CHO)—βAla—OMe
215 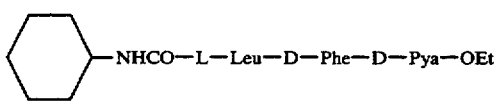
216 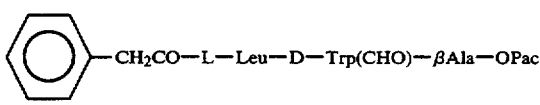
217 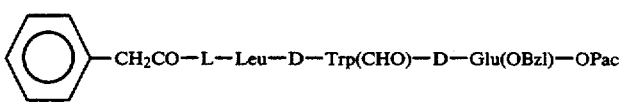
218 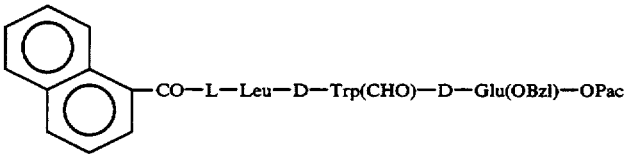
219 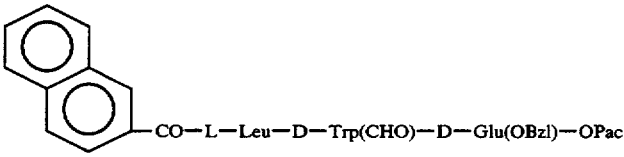
220 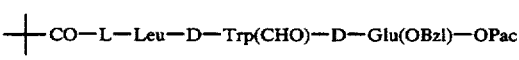
221 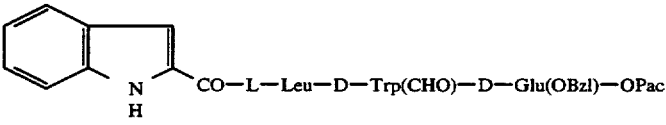
222 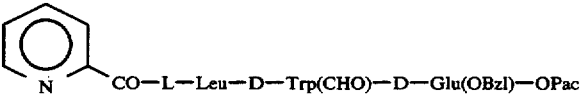
223 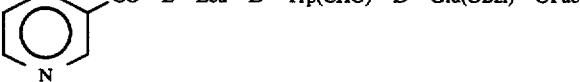

224 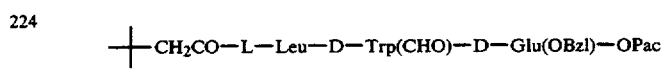CH₂CO—L—Leu—D—Trp(CHO)—D—Glu(OBzl)—OPac

225 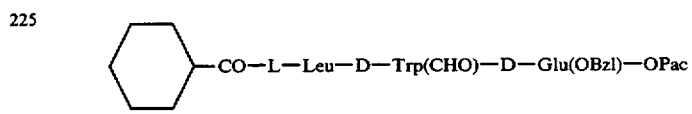—CO—L—Leu—D—Trp(CHO)—D—Glu(OBzl)—OPac

226 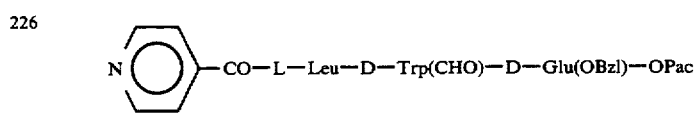—CO—L—Leu—D—Trp(CHO)—D—Glu(OBzl)—OPac

227 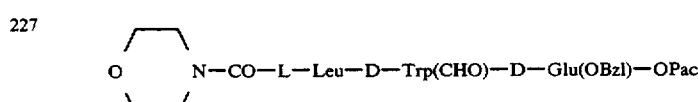—CO—L—Leu—D—Trp(CHO)—D—Glu(OBzl)—OPac

228 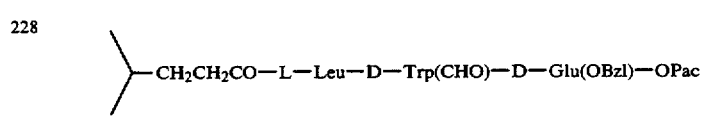CH₂CH₂CO—L—Leu—D—Trp(CHO)—D—Glu(OBzl)—OPac

229 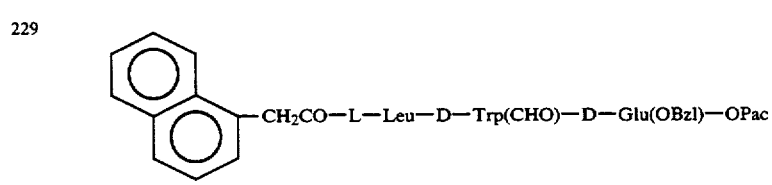CH₂CO—L—Leu—D—Trp(CHO)—D—Glu(OBzl)—OPac

230 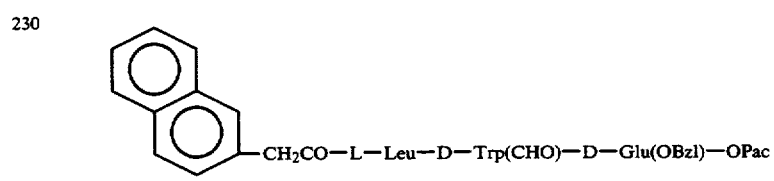CH₂CO—L—Leu—D—Trp(CHO)—D—Glu(OBzl)—OPac

231 Boc—D—alloIle—L—Leu—D—Trp(CHO)—D—Glu(OBzl)—OPac

232 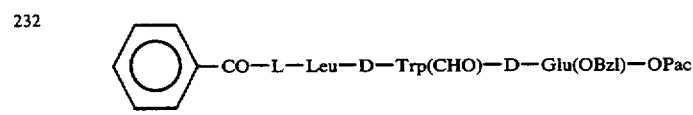—CO—L—Leu—D—Trp(CHO)—D—Glu(OBzl)—OPac

233 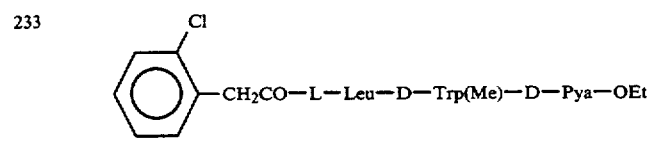CH₂CO—L—Leu—D—Trp(Me)—D—Pya—OEt

234 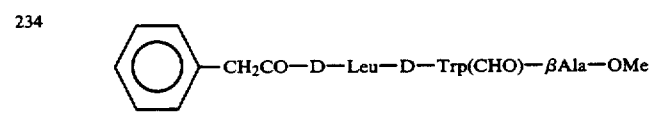CH₂CO—D—Leu—D—Trp(CHO)—βAla—OMe

235 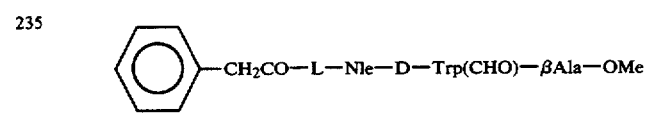CH₂CO—L—Nle—D—Trp(CHO)—βAla—OMe

236 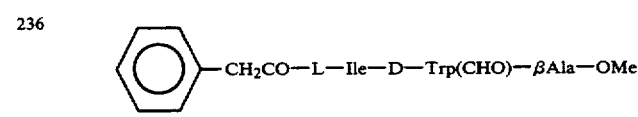CH₂CO—L—Ile—D—Trp(CHO)—βAla—OMe

-continued

237 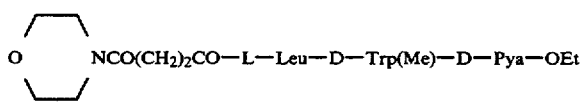 O⟨⟩NCO(CH₂)₂CO—L—Leu—D—Trp(Me)—D—Pya—OEt

238 Boc—D—alloIle—L—Leu—D—Trp(Me)—D—Pya—OEt

239 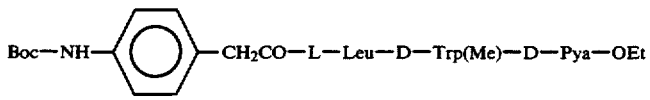 Boc—NH—⟨○⟩—CH₂CO—L—Leu—D—Trp(Me)—D—Pya—OEt

240 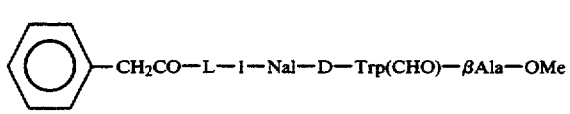 ⟨○⟩—CH₂CO—L—1—Nal—D—Trp(CHO)—βAla—OMe

241 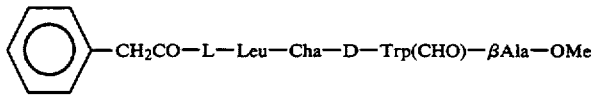 ⟨○⟩—CH₂CO—L—Leu—Cha—D—Trp(CHO)—βAla—OMe

242 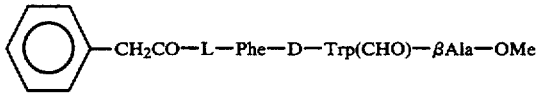 ⟨○⟩—CH₂CO—L—Phe—D—Trp(CHO)—βAla—OMe

243 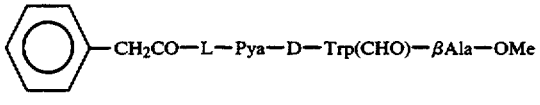 ⟨○⟩—CH₂CO—L—Pya—D—Trp(CHO)—βAla—OMe

244 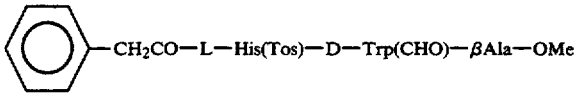 ⟨○⟩—CH₂CO—L—His(Tos)—D—Trp(CHO)—βAla—OMe

245 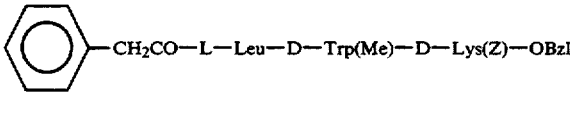 ⟨○⟩—CH₂CO—L—Leu—D—Trp(Me)—D—Lys(Z)—OBzl

246 Boc—D—alloIle—L—Leu—D—Trp(CHO)—Gly—OPac
247 Boc—D—alloIle—L—Leu—D—Trp(CHO)—NH(CH₂)₃COOPac
248 Boc—D—alloIle—L—Leu—D—Trp(CHO)—NH(CH₂)₄COOPac
249 Boc—D—alloIle—L—Leu—D—Trp(CHO)—NH(CH₂)₅COOPac
250 Boc—D—alloIle—L—Leu—D—Trp(CHO)—L—Glu(OBzl)—OPac
251 Boc—D—alloIle—L—Leu—D—Trp(CHO)—βAla—OPac 252 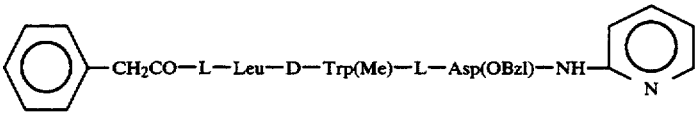 ⟨○⟩—CH₂CO—L—Leu—D—Trp(Me)—L—Asp(OBzl)—NH—⟨N⟩

253 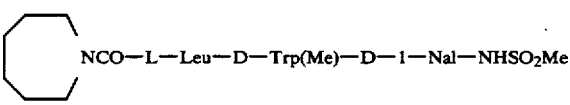 ⟨⟩NCO—L—Leu—D—Trp(Me)—D—1—Nal—NHSO₂Me

254 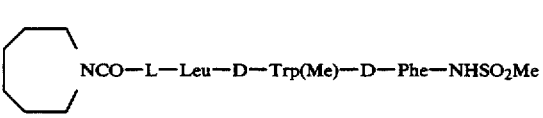 ⟨⟩NCO—L—Leu—D—Trp(Me)—D—Phe—NHSO₂Me

255 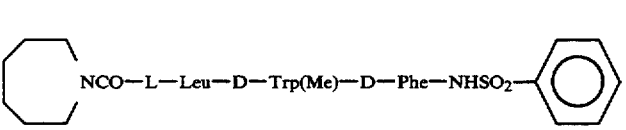 ⟨⟩NCO—L—Leu—D—Trp(Me)—D—Phe—NHSO₂—⟨○⟩

256 NCO—L—Leu—D—Trp(Me)—D—Pya—N(Et)₂

257 NCO—L—Leu—D—Trp(Me)—D—1—Nal—OEt

258 NCO—L—Leu—D—Trp(Me)—D—Phe—OEt

259 NCO—L—Leu—D—Trp(Me)—L—Pya—OEt

260 NCO—L—Leu—D—Trp(Me)—D—Leu—OEt

261 —NHCO—L—Leu—D—Trp(Me)—D—Leu—OBzl

262 NCO—L—Leu—D—Trp(Me)—D—1—Nal—NHSO₂Me

263 Boc—L—Leu—D—Trp(Me)—D—Pya—OEt

264 —CH₂CO—L—Leu—D—Trp(Me)—D—Lys—OH·HCl

265 —CH₂CO—L—Leu—D—Trp—βAla—OH

266 —CH₂CO—L—His—D—Trp(CHO)—βAla—OMe 267 2HCl·H—D—alloIle—L—Leu—D—Trp(Me)—D—Pya—OEt
268 HCl·H—D—alloIle—L—Leu—D—Trp(CHO)—D—Glu(OBzl)—OH 269 —CO—L—Leu—D—Trp(CHO)—D—Glu(OBzl)—OH 270 —CH₂CO—L—Leu—D—Trp(CHO)—D—Glu(OBzl)—OH 271 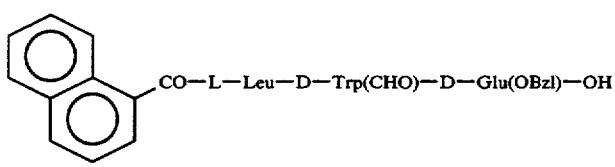
272 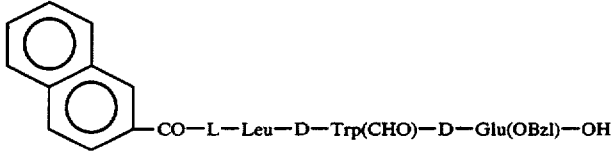
273 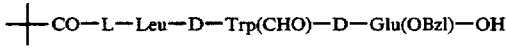
274 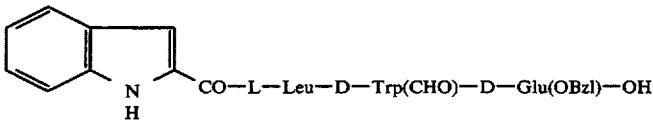
275 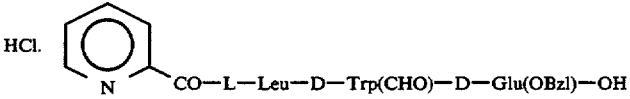
276 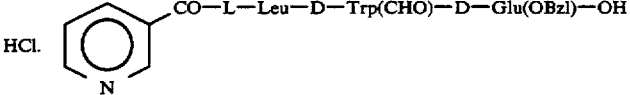
277 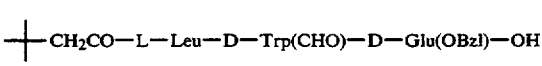
278 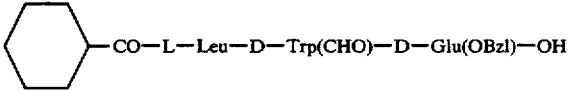
279 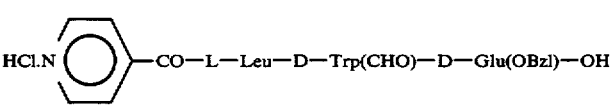
280 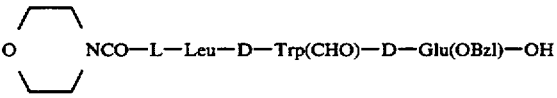
281 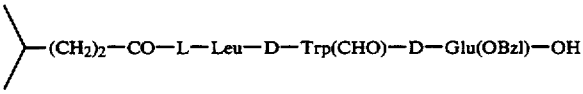
282 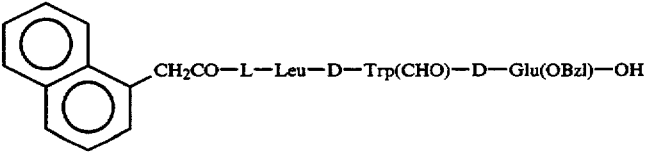

283 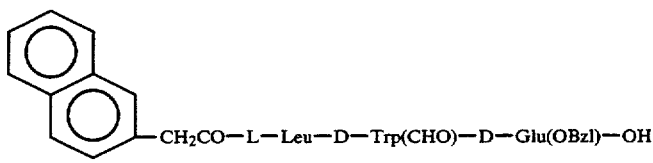
284 Boc—D—alloIle—L—Leu—D—Trp(CHO)—Gly—OH
285 Boc—D—alloIle—L—Leu—D—Trp(CHO)—NH(CH₂)₃COOH
286 Boc—D—alloIle—L—Leu—D—Trp(CHO)—NH(CH₂)₄COOH
287 Boc—D—alloIle—L—Leu—D—Trp(CHO)—NH(CH₂)₅COOH
288 Boc—D—alloIle—L—Leu—D—Trp(CHO)—L—Glu(OBzl)—OH
289 Boc—D—alloIle—L—Leu—D—Trp(CHO)—D—Glu(OBzl)—OH
290 
291 Boc—D—alloIle—L—Leu—D—Trp(CHO)—βAla—OH
292 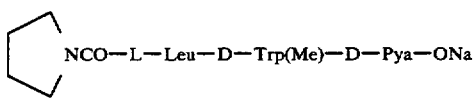
293 
294 
295 
296 
297 (Me)₂NCO—[structure]—NHCOCH₂—[structure]—CO—D—Trp(Me)—D—Pya—ONa
298 
299 (Me)₂NCO—[cyclohexyl]—NHCO—L—Leu—D—Trp(Me)—D—Pya—ONa 300 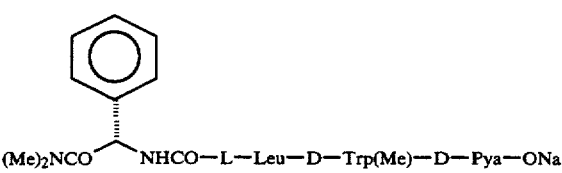
(Me)₂NCO—*—NHCO—L—Leu—D—Trp(Me)—D—Pya—ONa 301 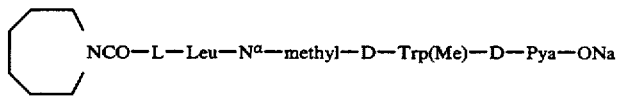
NCO—L—Leu—Nᵅ—methyl—D—Trp(Me)—D—Pya—ONa 302 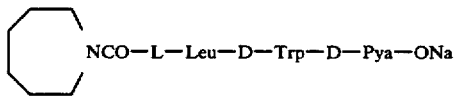
NCO—L—Leu—D—Trp—D—Pya—ONa 303 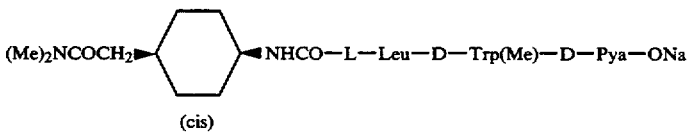
(Me)₂NCOCH₂—◁—NHCO—L—Leu—D—Trp(Me)—D—Pya—ONa
(cis)

304 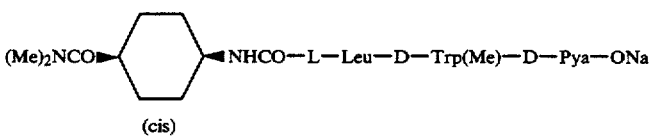
(Me)₂NCO—▷—NHCO—L—Leu—D—Trp(Me)—D—Pya—ONa
(cis)

305 (Me)₂NCOCH₂NHCO—L—Leu—D—Trp(Me)—D—Pya—ONa
306 (Me)₂NCO(CH₂)₂NHCO—L—Leu—D—Trp(Me)—D—Pya—ONa

307 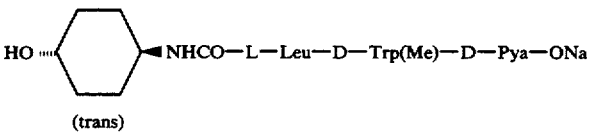
HO—◁—NHCO—L—Leu—D—Trp(Me)—D—Pya—ONa
(trans)

308 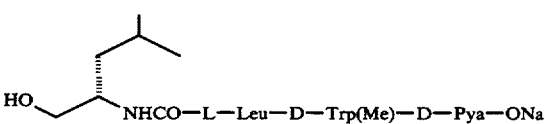
HO—CH₂—CH(iBu)—NHCO—L—Leu—D—Trp(Me)—D—Pya—ONa

309 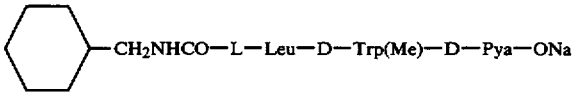
Cy—CH₂NHCO—L—Leu—D—Trp(Me)—D—Pya—ONa

310 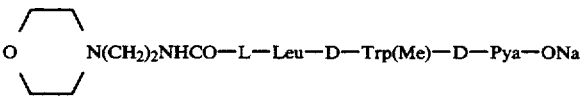
O(morpholino)N(CH₂)₂NHCO—L—Leu—D—Trp(Me)—D—Pya—ONa

311 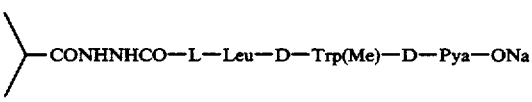
iPr—CONHNHCO—L—Leu—D—Trp(Me)—D—Pya—ONa

312 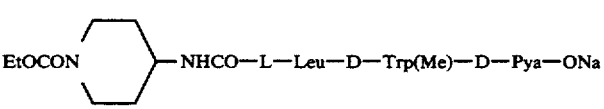
EtOCON—(piperidine)—NHCO—L—Leu—D—Trp(Me)—D—Pya—ONa

-continued
313 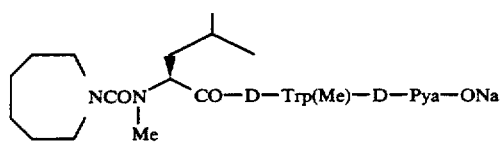
314 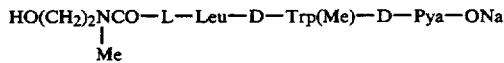
315 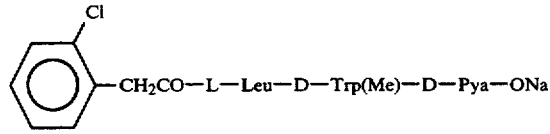
316 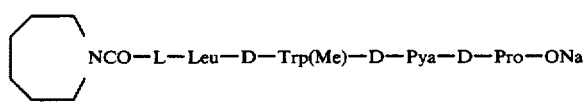
317 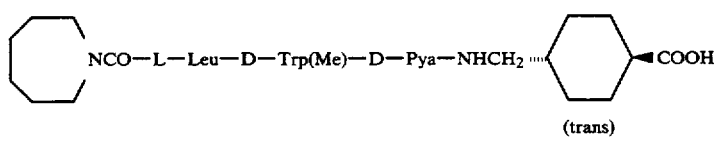
(trans)
318 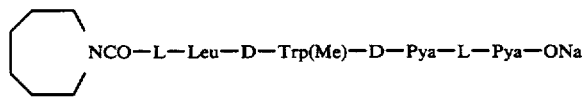
319 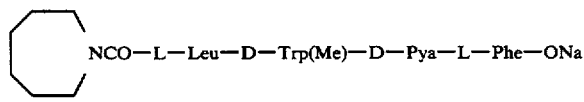
320 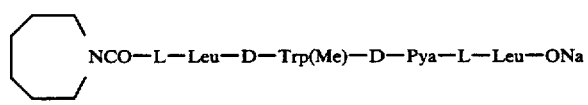
321 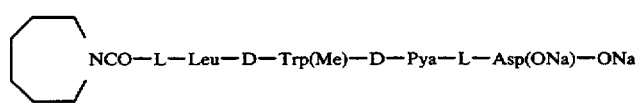
322 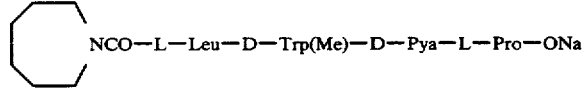
323 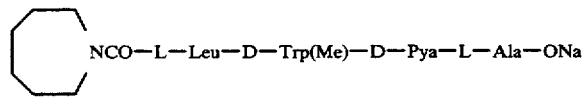
324 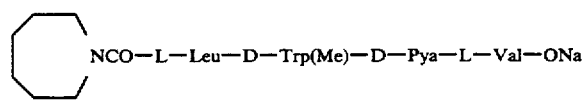
325 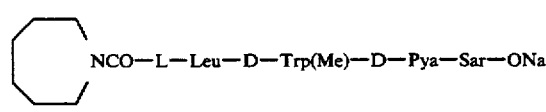

326 NCO—L—Leu—D—Trp(Me)—D—Pya—NH(CH₂)₅COONa
327 NCO—L—Leu—D—Trp(Me)—D—Pya—NH(CH₂)₄COONa
328 NCO—L—Leu—D—Trp(Me)—D—Pya—NH(CH₂)₃COONa
329 NCO—L—Leu—D—Trp(Me)—D—Pya—βAla—ONa
330 NCO—L—Leu—D—Trp(Me)—D—Pya—Gly—ONa
331 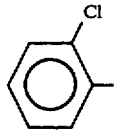—NHCO—L—Leu—D—Trp(Me)—D—Pya—βAla—OH
332 —CH₂CO—L—Leu—D—Trp(Me)—D—Leu—βAla—OH
333 —CH₂CO—L—Ile—D—Trp—βAla—OH
334 —CH₂CO—L—Nle—D—Trp—βAla—OH
335 —CH₂CO—D—Leu—D—Trp—βAla—OH
336 NCO—L—Leu—D—Trp(Me)—D—1—Nal—OH
337 NCO—L—Leu—D—Trp(Me)—D—Phe—OH
338 NCO—L—Leu—D—Trp(Me)—L—Pya—OH 339 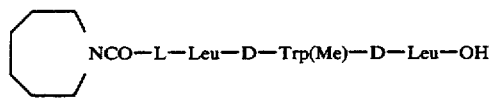NCO—L—Leu—D—Trp(Me)—D—Leu—OH
340 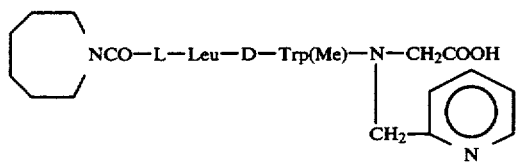NCO—L—Leu—D—Trp(Me)—N—CH₂COOH
341 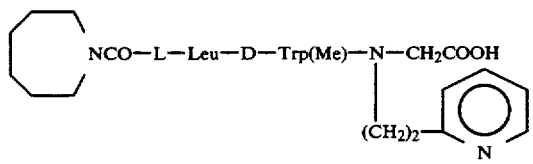NCO—L—Leu—D—Trp(Me)—N—CH₂COOH
342 Boc—D—alloIle—L—Leu—D—Trp(Me)—D—Pya—ONa
343 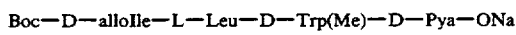—NHCO—D—alloIle—L—Leu—D—Trp(Me)—D—Pya—ONa
344 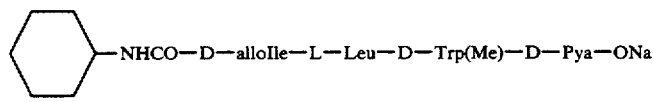—NHCO—L—Leu—D—Trp(Me)—D—Leu—ONa
345 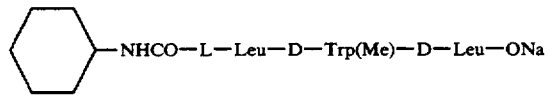NCO(CH₂)₂CO—L—Leu—D—Trp(Me)—D—Pya—ONa
346 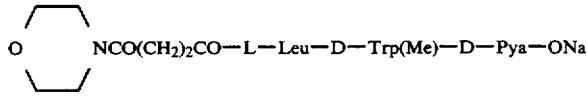NHCO—L—Leu—D—Trp(Me)—D—Pya—Et
347 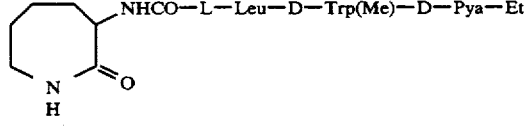NHCO—L—Leu—D—Trp(Me)—D—Pya—Na
348 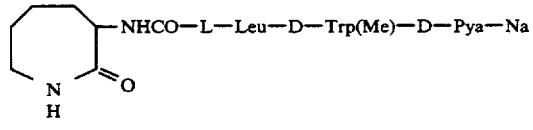NCO—L—Leu—D—Trp(Me)—D—Pya—NH(CH₂)₂N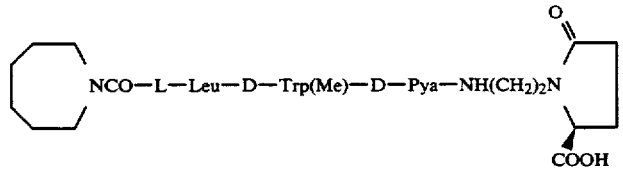
349 Boc—L—Leu—D—Trp(CHO)—D—Glu(OBzl)—OH
350 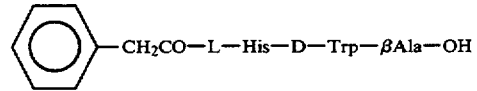—CH₂CO—L—His—D—Trp—βAla—OH
351 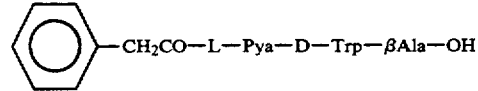—CH₂CO—L—Pya—D—Trp—βAla—OH 352 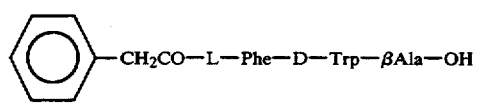
353 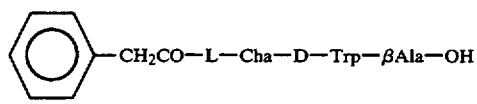
354 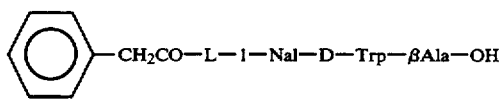
355 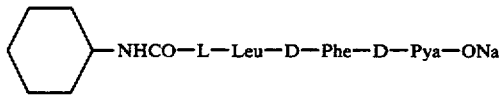
356 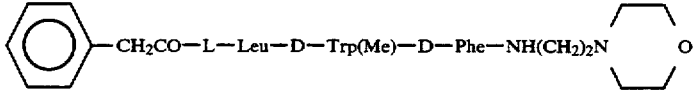
357 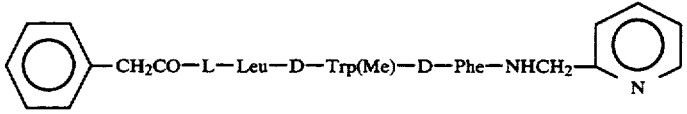
358 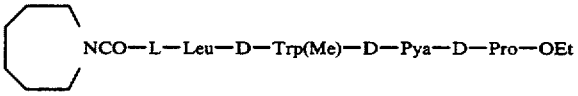
359 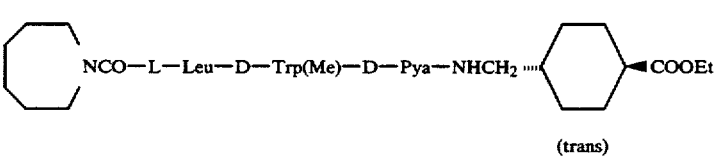
(trans)
360 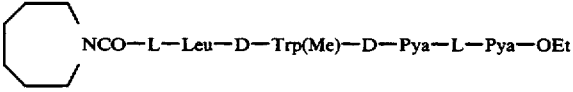
361 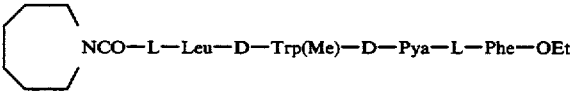
362 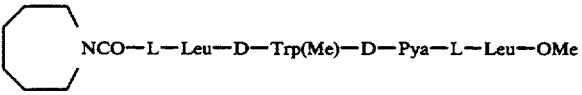
363 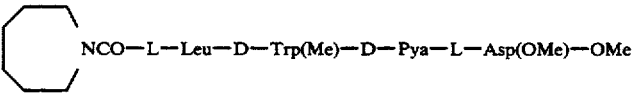
364 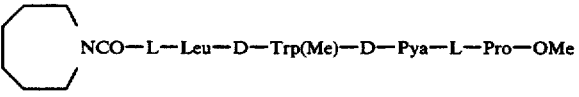

-continued

365 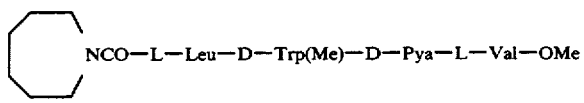 NCO—L—Leu—D—Trp(Me)—D—Pya—L—Val—OMe

366 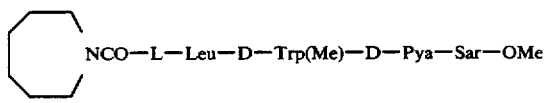 NCO—L—Leu—D—Trp(Me)—D—Pya—Sar—OMe

367 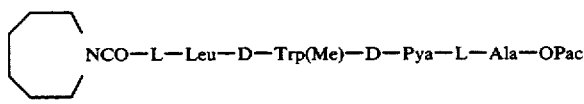 NCO—L—Leu—D—Trp(Me)—D—Pya—L—Ala—OPac

368 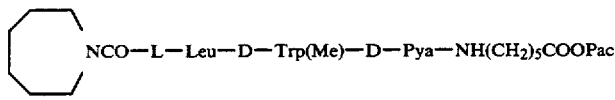 NCO—L—Leu—D—Trp(Me)—D—Pya—NH(CH$_2$)$_5$COOPac

369 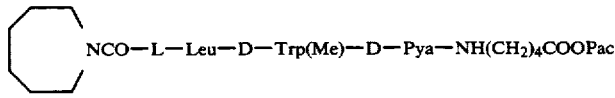 NCO—L—Leu—D—Trp(Me)—D—Pya—NH(CH$_2$)$_4$COOPac

370 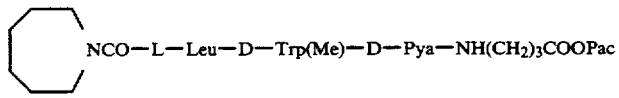 NCO—L—Leu—D—Trp(Me)—D—Pya—NH(CH$_2$)$_3$COOPac

371 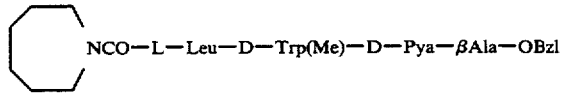 NCO—L—Leu—D—Trp(Me)—D—Pya—βAla—OBzl

372 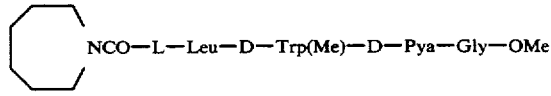 NCO—L—Leu—D—Trp(Me)—D—Pya—Gly—OMe

373 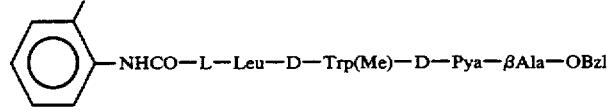 NHCO—L—Leu—D—Trp(Me)—D—Pya—βAla—OBzl

374 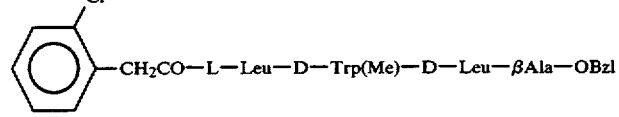 CH$_2$CO—L—Leu—D—Trp(Me)—D—Leu—βAla—OBzl

375 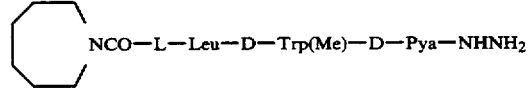 NCO—L—Leu—D—Trp(Me)—D—Pya—NHNH$_2$

376 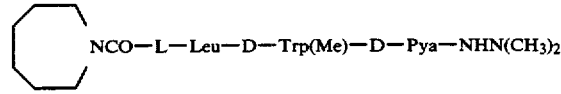 NCO—L—Leu—D—Trp(Me)—D—Pya—NHN(CH$_3$)$_2$

377 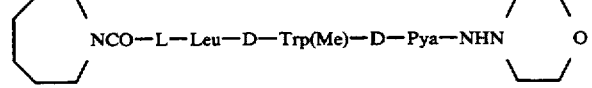 NCO—L—Leu—D—Trp(Me)—D—Pya—NHN⟨O⟩

378 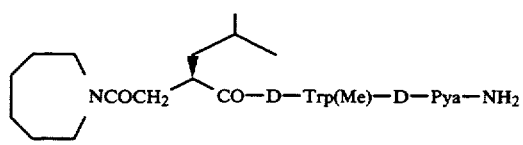
379 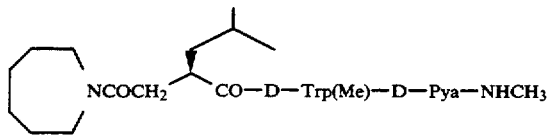
380 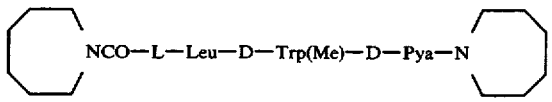
381 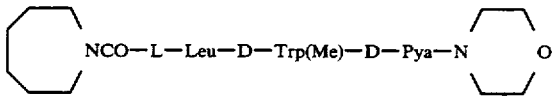
382 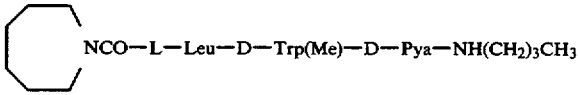
383 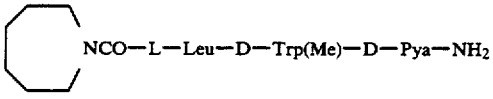
384 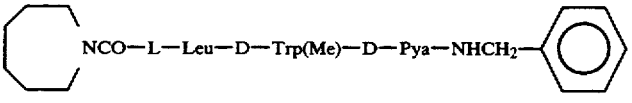
385 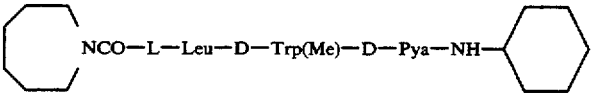
386 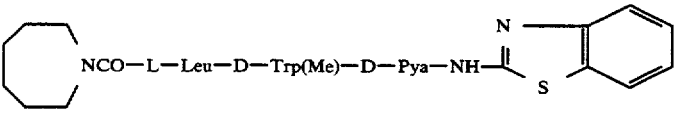
387 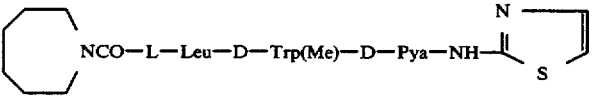
388 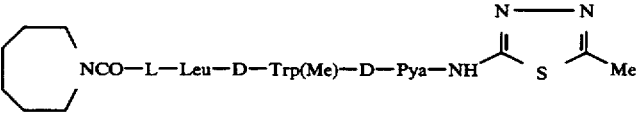
389 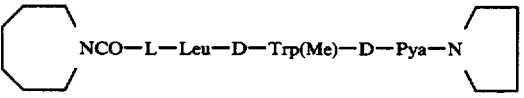
390 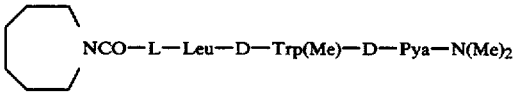

391 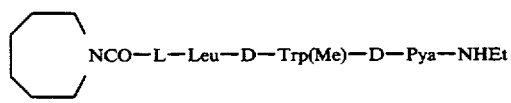
392 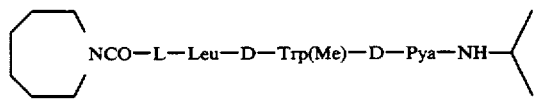
393 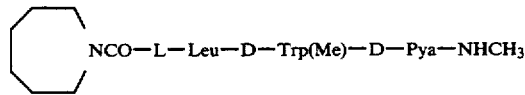
394 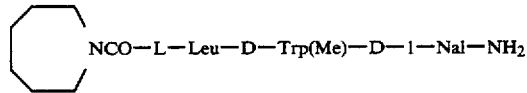
395 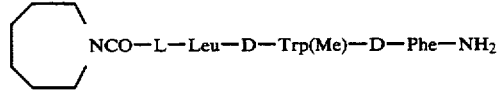
396 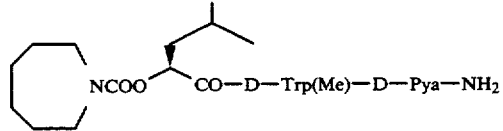
397 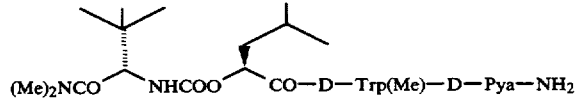
398 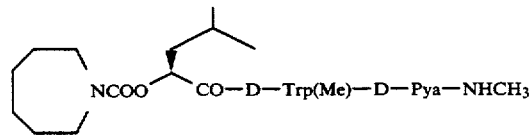
399 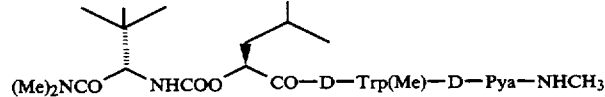
400 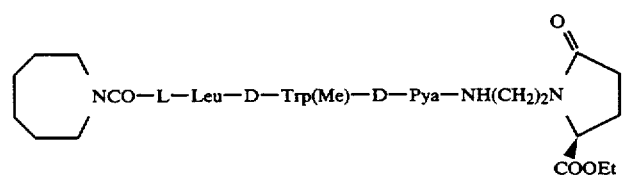
401 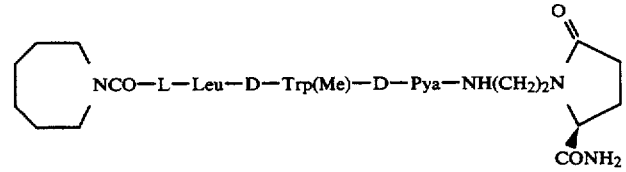

-continued
402 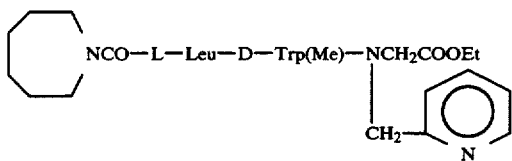
403 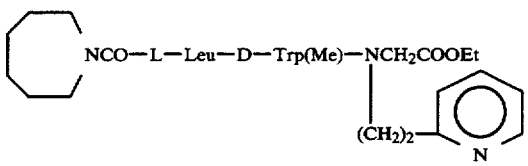
404 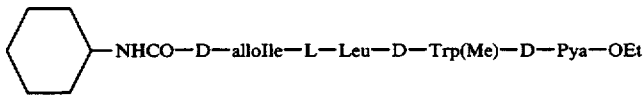
405  HCl.H—L—Leu—D—Trp(Me)—D—Phe—OBzl
406  2HCl.H—L—Leu—D—Trp(Me)—D—Pya—OEt
407  HCl.H—D—Leu—D—Trp(CHO)—βAla—OMe
408  HCl.H—L—Nle—D—Trp(CHO)—βAla—OMe
409  HCl.H—L—Ile—D—Trp(CHO)—βAla—OMe
410  HCl.H—L—Leu—D—Trp(CHO)—D—Glu(OBzl)—OPac
411  HCl.H—L—Leu—D—Trp(CHO)—βAla—OPac
412  HCl.H—L—1-Nal—D—Trp(CHO)—βAla—OMe
413  HCl.H—L—Cha—D—Trp(CHO)—βAla—OMe
414  HCl.H—L—Phe—D—Trp(CHO)—βAla—OMe
415  2HCl.H—L—Pya—D—Trp(CHO)—βAla—OMe
416  TFA.H—L—His(Tos)—D—Trp(CHO)—βAla—OMe
417 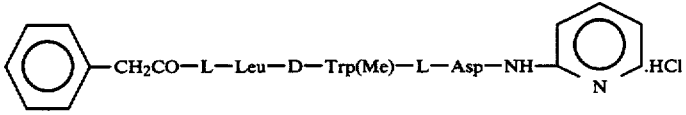
418 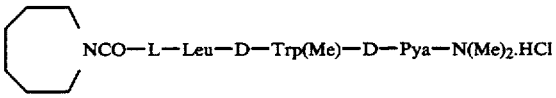
419 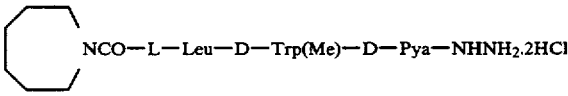
420 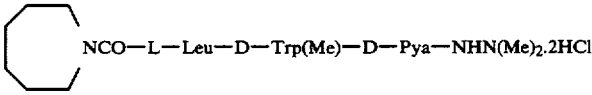
421 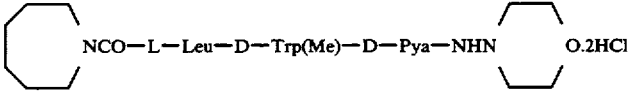
422 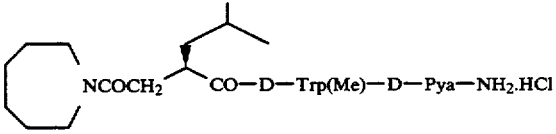
423 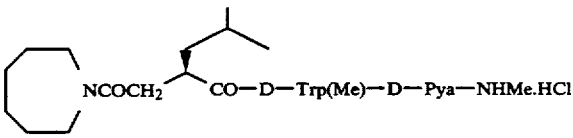

424 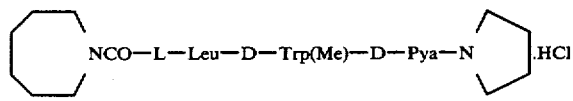
425 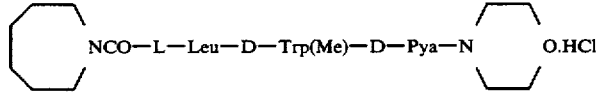
426 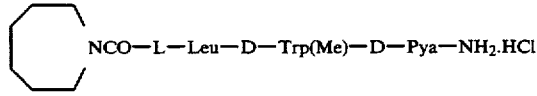
427 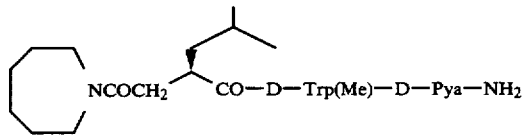
428 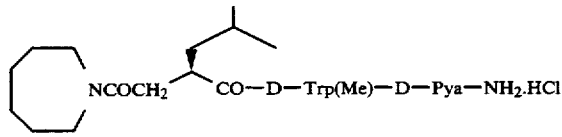
429 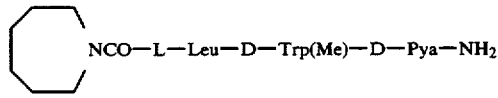
430 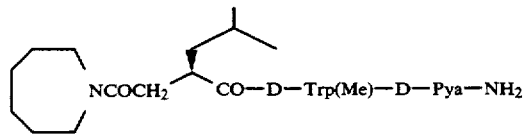
431 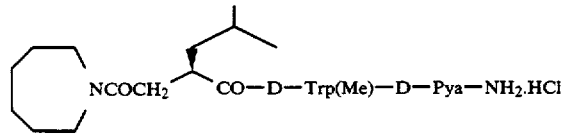
432 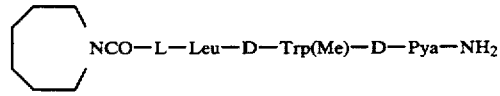
433 
434 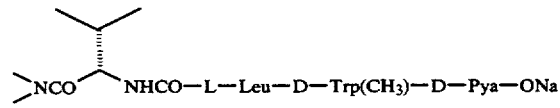
In the above table, the configurations accompanied with cis or trans do not mean the absolute configurations, but the relative configurations only. The other configurations mean the absolute ones.
What is claimed is:
1. A peptide compound having the formula (I')

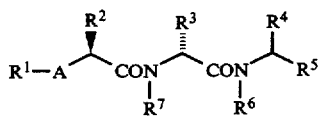

or a pharmaceutically acceptable salt thereof in which
$R^1$ is acyl,
$R^2$ is lower alkyl, cyclo(lower)alkyl(lower)alkyl or optionally substituted heterocyclic(lower)alkyl,
$R^3$ is optionally substituted heterocyclic(lower)alkyl or optionally substituted ar(lower)alkyl,
$R^4$ is lower alkyl, amino(lower)alkyl, protected amino(lower)alkyl, carboxy(lower)alkyl, protected carboxy(lower)alkyl or optionally substituted heterocyclic(lower)alkyl,
$R^5$ is carboxy, protected carboxy, carboxy(lower)alkyl or protected carboxy(lower)alkyl,
$R^6$ is hydrogen, lower alkyl, $C_{6-10}$ar(lower)alkyl amino(lower)alkyl, protected amino(lower)alkyl, carboxy(lower)alkyl, protected carboxy(lower)alkyl, or heterocyclic(lower)alkyl,
$R^7$ is hydrogen or lower alkyl, and
A is —O—, —NH—, lower alkylimino or lower alkylene.

2. The compound of claim 1, wherein
$R^2$ is lower alkyl; cyclo(lower)alkyl(lower)alkyl; or heterocyclic(lower)alkyl optionally substituted by suitable substituent(s) selected from hydroxy, protected hydroxy, halogen, lower alkoxy, lower alkyl, amino, nitro, cyano and imino-protective group; said heterocyclic group being
unsaturated 3 to 8-membered heteromonocyclic group containing 1 to 4 nitrogen atom(s),
saturated 3 to 8-membered heteromonocyclic group containing 1 to 4 nitrogen atom(s),
unsaturated condensed 7 to 12-membered heterocyclic group containing 1 to 5 nitrogen atom(s),
unsaturated 3 to 8-membered heteromonocyclic group containing 1 to 2 oxygen atom(s) and 1 to 3 nitrogen atom(s),
saturated 3 to 8-membered heteromonocyclic group containing 1 to 2 oxygen atom(s) and 1 to 3 nitrogen atom(s),
unsaturated condensed 7 to 12-membered heterocyclic group containing 1 to 2 oxygen atom(s) and 1 to 3 nitrogen atom(s),
unsaturated 3 to 8-membered heteromonocyclic group containing 1 to 2 sulfur atom(s) and 1 to 3 nitrogen atom(s),
saturated 3 to 8-membered heteromonocyclic group containing 1 to 2 sulfur atom(s) and 1 to 3 nitrogen atom(s),
unsaturated 3 to 8-membered heteromonocyclic group containing a sulfur atom, or
unsaturated condensed 7 to 12-membered heterocyclic group containing 1 to 2 sulfur atom(s) and 1 to 3 nitrogen atom(s),
$R^3$ is heterocyclic(lower)alkyl or ar(lower)alkyl, each of which is optionally substituted by suitable substituent(s) selected from hydroxy, protected hydroxy, halogen, lower alkoxy, lower alkyl, amino, nitro, cyano and imino-protective group, said heterocyclic group being
unsaturated 3 to 8-membered heteromonocyclic group containing 1 to 4 nitrogen atom(s),
saturated 3 to 8-membered heteromonocyclic group containing 1 to 4 nitrogen atom(s),
unsaturated condensed 8 to 12-membered heterocyclic group containing 1 to 5 nitrogen atom(s),
unsaturated 3 to 8-membered heteromonocyclic group containing 1 to 2 oxygen atom(s) and 1 to 3 nitrogen atom(s),
saturated 3 to 8-membered heteromonocyclic group containing 1 to 2 oxygen atom(s) and 1 to 3 nitrogen atom(s),
unsaturated condensed 7 to 12-membered heterocyclic group containing 1 to 2 oxygen atom(s) and 1 to 3 nitrogen atom(s),
unsaturated 3 to 8-membered heteromonocyclic group containing 1 to 2 sulfur atom(s) and 1 to 3 nitrogen atom(s),
saturated 3 to 8-membered heteromonocyclic group containing 1 to 2 sulfur atom(s) and 1 to 3 nitrogen atom(s),
unsaturated 3 to 8-membered heteromonocyclic group containing a sulfur atom, or
unsaturated condensed 7 to 12-membered heterocyclic group containing 1 to 2 sulfur atom(s) and 1 to 3 nitrogen atom(s),
$R^4$ is lower alkyl, amino(lower)alkyl, protected amino(lower)alkyl, carboxy(lower)alkyl, protected carboxy(lower)alkyl or optionally substituted heterocyclic(lower)alkyl, said heterocyclic group being
unsaturated 3 to 8-membered heteromonocyclic group containing 1 to 4 nitrogen atom(s),
saturated 3 to 8-membered heteromonocyclic group containing 1 to 4 nitrogen atom(s),
unsaturated condensed 8 to 12-membered heterocyclic group containing 1 to 5 nitrogen atom(s),
unsaturated 3 to 8-membered heteromonocyclic group containing 1 to 2 oxygen atom(s) and 1 to 3 nitrogen atom(s),
saturated 3 to 8-membered heteromonocyclic group containing 1 to 2 oxygen atom(s) and 1 to 3 nitrogen atom(s),
unsaturated condensed 7 to 12-membered heterocyclic group containing 1 to 2 oxygen atom(s) and 1 to 3 nitrogen atom(s),
unsaturated 3 to 8-membered heteromonocyclic group containing 1 to 2 sulfur atom(s) and 1 to 3 nitrogen atom(s),
saturated 3 to 8-membered heteromonocyclic group containing 1 to 2 sulfur atom(s) and 1 to 3 nitrogen atom(s),
unsaturated 3 to 8-membered heteromonocyclic group containing a sulfur atom or
unsaturated condensed 7 to 12-membered heterocyclic group containing 1 to 2 sulfur atom(s) and 1 to 3 nitrogen atom(s),
wherein said heterocyclic group may be substituted by one or two suitable substituent(s) selected from hydroxy, protected hydroxy, halogen, lower alkoxy, lower alkyl, amino, nitro, cyano and imino-protective group,
$R^5$ is carboxy, esterified carboxy or amidated carboxy, and
$R^6$ is hydrogen or heterocyclic(lower)alkyl, in which said heterocyclic group is unsaturated 3 to 8-membered heteromonocyclic group containing 1 to 4 nitrogen atom(s).

3. The compound of claim 2, wherein $R^1$ is carbamoyl; saturated or unsaturated, acyclic or cyclic aliphatic acyl optionally substituted by aromatic or heterocyclic group(s), aromatic acyl, or heterocyclic acyl, each of which is derived from an organic carboxylic or an organic carbonic or an organic sulfonic or an organic carbamic acid;

$R^2$ is lower alkyl; $C_3$-$C_7$cycloalkyl(lower)alkyl; or 5- or 6-membered aromatic heteromonocyclic(lower)alkyl, in which the heterocyclic ring contains one to three nitrogen atoms;

$R^3$ is 9- or 10-membered benzene-condensed heterocyclic (lower)alkyl, in which the heterocyclic group contains one to three nitrogen atoms and may be substituted by lower alkyl or an organic carboxylic acyl; or $C_6$-$C_{10}$ar(lower)alkyl;

$R^4$ is lower alkyl; amino(lower)alkyl; protected amino(lower)alkyl; carboxy(lower)alkyl; protected carboxy(lower)alkyl; 5- or 6-membered aromatic heteromonocyclic(lower)alkyl, in which the heterocyclic ring contains one to three nitrogen atoms; or 5- or 6-membered aromatic heteromonocyclic(lower)alkyl, in which the heterocyclic ring contains one or two nitrogen atoms and one sulfur atom;

$R^5$ is carboxy; esterified carboxy selected from: lower alkoxycarbonyl, $C_6$-$C_{10}$ar(lower)alkoxycarbonyl and $C_6$-$C_{10}$aroyl(lower)alkoxycarbonyl; amidated carboxy selected from: carbamoyl, N- or N,N-di(-lower)alkylcarbamoyl, lower alkylcarbamoyl substituted by one or two substituents selected from carboxy and protected carboxy, N-(lower)alkyl-N-[carboxy- or protected carboxy (lower)alkyl]carbamoyl, $C_6$-$C_{10}$ar(lower)alkylcarbamoyl, carboxy- or protected carboxy-substituted $C_6$-$C_{10}$ ar(lower)alkylcarbamoyl, $C_3$-$C_7$cycloalkylcarbamoyl, N-[carboxy- or protected carboxy-substituted $C_3$-$C_7$-cycloalkyl(lower)alkyl]carbamoyl, lower alkylsulfonylcarbamoyl, $C_6$-$C_{10}$arylsulfonylcarbamoyl, carboxy- or protected carboxy-substituted 5- or 6-membered aromatic heteromonocyclic(lower)alkylcarbamoyl, in which the heterocyclic ring contains one to three nitrogen atoms, lower alkyleneaminocarbonyl, lower alkyleneaminocarbonyl substituted by carboxy or protected carboxy, [lower alkyleneamino(lower)alkyl]carbamoyl substituted by one to two substituents selected from carboxy, protected carboxy and carbamoyl, morpholinocarbonyl, 5- or 6-membered saturated heteromonocycliccarbamoyl, in which the heterocyclic ring contains one nitrogen atom and one oxygen atom, 5- or 6-membered aromatic heteromonocycliccarbamoyl, in which the heterocyclic ring contains one to three nitrogen atoms, 5- or 6-membered aromatic heteromonocycliccarbamoyl, in which the heterocyclic ring contains one to two nitrogen atoms and one sulfur atom and may be substututed by lower alkyl, 9- or 10-membered benzene-condensed heterocyclic carbamoyl, in which the heterocyclic ring contains one to two nitrogen atoms and one sulfur atom, 5- or 6-membered saturated heteromonocyclic(lower)alkylcarbamoyl, in which the heterocyclic ring contains one nitrogen atom and one oxygen atom, 5- or 6-membered aromatic heteromonocyclic(lower)alkylcarbonyl, in which the heterocyclic ring contains one to three nitrogen atoms, carbazoyl, di(-lower)alkylcarbazoyl; carboxy(lower)alkyl; or protected carboxy(lower)alkyl; and $R^6$ is hydrogen; or 5- or 6-membered aromatic heteromonocyclic (lower)alkyl, in which the heterocyclic ring contains one to three nitrogen atoms.

4. The compound of claim 3, wherein $R^1$ is carbamoyl; lower alkanoyl; amino(lower)alkanoyl; lower alkoxycarbonylamino(lower)alkanoyl; $C_3$-$C_7$cycloalkylureido(lower)alkanoyl; lower alkoxycarbonyl; $C_3$-$C_7$cycloalkyl(lower)alkanoyl; $C_3$-$C_7$cycloalkylcarbonyl; $C_3$-$C_7$cycloalkyloxycarbonyl; benzoyl; naphthoyl; phenyl(lower)alkanoyl; naphthyl(lower)alkanoyl; amino-substituted phenyl(lower)alkanoyl; lower alkoxycarbonylamino-substituted phenyl(lower)alkanoyl; halophenyl(lower)alkanoyl; phenyl(lower)alkenoyl; phenylglyoxyloyl; phenyl(lower)alkylglyoxyloyl; pyridylcarbonyl; tetrahydropyridylcarbonyl; tetrahydroquinolylcarbonyl; tetrahydroisoquinolylcarbonyl; morpholinylcarbonyl; thiomorpholinylcarbonyl; indolylcarbonyl; piperazinylcarbonyl substituted by one to three substituents selected from oxo and lower alkyl; pyridyl(lower)alkanoyl; morpholinylcarbonyl(lower)alkanoyl; phenyl(lower)alkylsulfonyl; N- or N,N-di($C_1$-$C_{10}$)alkylcarbamoyl; hydroxy(lower)alkylcarbamoyl; carboxy(lower)alkylcarbamoyl; lower alkoxycarbonyl(lower)alkylcarbamoyl; carbamoyl(lower)alkylcarbamoyl; [N- or N,N-di(lower)alkylcarbamoyl](lower)alkylcarbamoyl; N-lower alkyl-N-[hydroxy(lower)alkyl]carbamoyl; N-lower alkyl-N-[di(lower)alkylcarbamoyl(lower)alkyl]carbamoyl; $C_3$-$C_{10}$alkyleneaminocarbonyl; di(lower)alkylcarbamoyl(lower)alkyleneaminocarbonyl; N-lower alkyl-N-($C_3$-$C_7$)cycloalkylcarbamoyl; mono- or di($C_3$-$C_7$)cycloalkylcarbamoyl; hydroxy- or di(lower)alkylcarbamoyl- or di(lower)alkylcarbamoyl(lower)alkyl-substituted ($C_3$-$C_7$)cycloalkylcarbamoyl; $C_3$-$C_7$cycloalkyl(lower)alkylcarbamoyl; di(lower)alkylcarbamoyl-substituted $C_3$-$C_7$cycloalkyl(lower)alkylcarbamoyl; di(lower)alkylcarbamoyl-substituted phenyl(lower)alkylcarbamoyl; phenylcarbamoyl, in which the phenyl group may be substituted by one to three substituents selected from halogen, lower alkyl and lower alkoxy; pyridylcarbamoyl; N-lower alkoxycarbonylpiperidylcarbonyl; morpholinyl(lower)alkylcarbamoyl; lower alkanoylcarbazoyl; lower alkyleneaminocarbamoyl; N-($C_3$-$C_7$)cycloalkylcarbamoyl(lower)alkylcarbamoyl; lower alkyleneaminocarbonyl(lower)alkylcarbamoyl; pyridyl(lower)alkylcarbamoyl; or oxo-substituted hexahydroazepinylcarbamoyl;

$R^2$ is lower alkyl;

$R^3$ is indolyl(lower)alkyl; N-(lower)alkylindolyl(lower)alkyl; N-(lower)alkanoylindolyl(lower)alkyl; phenyl(lower)alkyl; or naphthyl(lower)alkyl;

$R^4$ is lower alkyl; amino(lower)alkyl; mono- or di or triphenyl(lower)alkoxycarbonylamino(lower)alkyl; carboxy(lower)alkyl; mono- or di or triphenyl(lower)alkoxycarbonyl(lower)alkyl; pyridyl(lower)alkyl; imidazolyl(lower)alkyl; or thiazolyl(lower)alkyl;

$R^5$ is carboxy; lower alkoxycarbonyl; mono or di or triphenyl(lower)alkoxycarbonyl; benzoyl(lower)alkoxycarbonyl; carbamoyl; N- or N,N-di(lower)alkylcarbamoyl; lower alkylcarbamoyl substituted by one or two substituents selected from carboxy, lower alkoxycarbonyl, mono or di or triphenyl(lower)alkoxycarbonyl and benzoyl(lower)alkoxycarbonyl); N-(lower)alkyl-N-[carboxy- or lower alkoxycarbonyl)(lower)alkyl]carbamoyl; phenyl(lower)alkylcarbamoyl; carboxy- or lower alkoxycarbonyl-substituted phenyl(lower)alkylcarbamoyl; $C_3$-$C_7$cycloalkylcarbamoyl; carboxy($C_3$-$C_7$-)cycloalkyl(lower)alkyl]carbamoyl; lower alkoxycarbonyl($C_3$-$C_7$)cycloalkyl(lower)alkyl]carbamoyl; lower alkylsulfonylcarbamoyl,; phenylsulfonylcarbamoyl, carboxy- or lower alkoxycarbonyl-substituted pyridyl(lower)alkylcarbamoyl; lower alkyleneaminocarbonyl; lower alkyleneaminocarbonyl substituted by carboxy or lower alkoxycarbonyl; [lower alkyleneamino(lower)alkyl]carbamoyl substituted by one to two substituents selected from carboxy, lower alkoxycarbonyl and carbamoyl; morpholinocarbonyl; morpholinylcarbamoyl; pyridylcarbamoyl; thiazolylcarbamoyl; lower alkylthiadiazolylcarbamoyl; benzothiazolylcarbamoyl; morpholinyl(lower)alkylcarbamoyl; pyridyl(lower)alkylcarbonyl; carbazoyl; di(lower)alkylcarbazoyl; carboxy(lower)alkyl; lower alkoxycarbonyl(lower)alkyl; or benzoyl(lower)alkoxycarbonyl(lower)alkyl, and $R^6$ and $R^7$ are each hydrogen.

5. The compound of claim 4, wherein $R^1$ is N- or N,N-di($C_1$-$C_{10}$)alkylcarbamoyl, N-lower alkyl-N-($C_3$-$C_7$)cycloalkylcarbamoyl, N- or N,N-di($C_3$-$C_7$)cycloalkylcarbamoyl, N-(lower)alkyl-N-[N,N-di(lower)alkylcarbamoyl(lower)alkyl]carbamoyl, phenylcarbamoyl, $C_3$-$C_{10}$ alkyleneaminocarbonyl, [N,N-di(lower)alkylcarbamoyl](lower)alkylcarbamoyl or N-(lower)alkyl-N-[hydroxy(lower)alkyl]carbamoyl, $R^2$ is lower alkyl, $R^3$ is indolyl(lower)alkyl, N-(lower)alkanoylindolyl(lower)alkyl or N-(lower)alkylindolyl(lower)alkyl, $R^4$ is pyridyl(lower)alkyl, $R^5$ is carboxy, lower alkoxycarbonyl, carbamoyl or N- or N,N-di(lower)alkylcarbamoyl, and A is methylene or —NH—.

6. The compound of claim 5, wherein $R^1$ is isopropylcarbamoyl, 2-methylbutylcarbamoyl, heptylcarbamoyl, dimethylcarbamoyl, diethylcarbamoyl, dipropylcarbamoyl, diisopropylcarbamoyl, dibutylcarbamoyl, diisobutylcarbamoyl, pyrrolidin-1-ylcarbonyl, piperidin-1-ylcarbonyl, 3,5- or 2,6-dimethylpiperidin-1-ylcarbonyl, hexahydro-1H-azepin-1-ylcarbonyl, octahydroazocin-1-ylcarbonyl or N-(1-dimethylcarbamoyl-2-methylpropyl)carbamoyl, $R^2$ is isobutyl, $R^3$indol-3-ylmethyl, N-formylindol-3-ylmethyl, N-methylindol-3-ylmethyl, N-ethylindol-3-ylmethyl, N-propylindol-3-ylmethyl or N-isobutylindol-3-ylmethyl, $R^4$ is 2-pyridylmethyl, $R^5$ is carboxy, methoxycarbonyl, ethoxycarbonyl, carbamoyl, methylcarbamoyl, ethylcarbamoyl, propylcarbamoyl, isopropylcarbamoyl, butylcarbamoyl, N,N-dimethylcarbamoyl or N,N-diethylcarbamoyl.

7. A process for the preparation of a peptide compound having the formula (I')

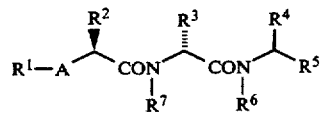

or a pharmaceutically acceptable salt thereof in which $R^2$ is acyl, $R^2$ is lower alkyl, cyclo(lower)alkyl(lower)alkyl or optionally substituted heterocyclic(lower)alkyl, $R^3$ is optionally substituted heterocyclic(lower)alkyl or optionally substituted ar(lower)alkyl, $R^4$ is lower alkyl, amino(lower)alkyl, protected amino(lower)alkyl, carboxy(lower)alkyl, protected carboxy(lower)alkyl or optionally substituted heterocyclic(lower)alkyl, $R^5$ is carboxy, protected carboxy, carboxy(lower)alkyl or protected carboxy(lower)alkyl, $R^6$ is hydrogen, lower alkyl, $C_{6-10}$ar(lower)alkyl amino(lower)alkyl, protected amino(lower)alkyl, carboxy(lower)alkyl, protected carboxy(lower)alkyl, or heterocyclic(lower)alkyl, $R^7$ is hydrogen or lower alkyl, and A is —O—, —NH—, lower alkylimino or lower alkylene, which comprises (a) reacting a compound of the formula:

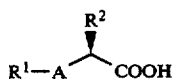

wherein $R^1$, $R^2$ and A are each as defined above or its reactive derivative at the carboxy group or a salt thereof, with a compound of the formula:

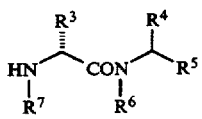

wherein $R^3$, $R^4$, $R^5$, $R^6$ and $R^7$ are each as defined above, or its reactive derivative at the amino group, or a salt thereof, to give a compound of the formula:

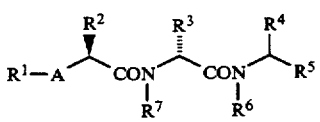

wherein $R^1$, $R^2$, $R^3$, $R^4$, $R^5$, $R^6$, $R^7$ and A are each as defined above, or a salt thereof; or (b) reacting a compound of the formula:

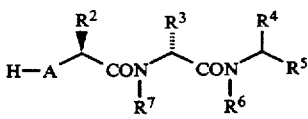

wherein $R^2$, $R^3$, $R^4$, $R^5$, $R^6$, $R^7$ and A are each as defined above, or its reactive derivative at the amino group, or a salt thereof, with a compound of the formula:

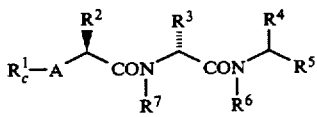   (IV)

wherein $R_C^1$ is acyl, or its reactive derivative at the carboxy group, or a salt thereof, to give a compound of the formula:

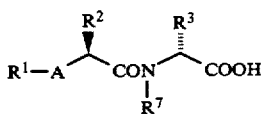   (I-b)

wherein $R_C^1$, $R^2$, $R^3$, $R^4$, $R^5$, $R^6$, $R^7$ and A are each as defined above or a salt thereof; or (c) reacting a compound of the formula:

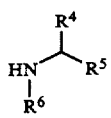   (V)

wherein $R^1$, $R^2$, $R^3$, $R^7$ and A are each as defined above, or its reactive derivative at the carboxy group, or a salt thereof, with a compound of the formula:

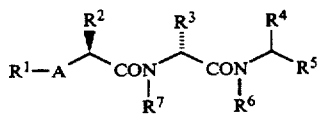   (VI)

wherein $R^4$, $R^5$ and $R^6$ are each as defined above, or its reactive derivative at the amino group, or a salt thereof, to give a compound of the formula:

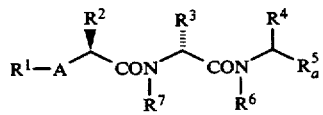   (I')

wherein $R^1$, $R^2$, $R^3$, $R^4$, $R^5$, $R^6$, $R^7$ and A are each as defined above or a salt thereof; or (d) subjecting a compound of the formula:

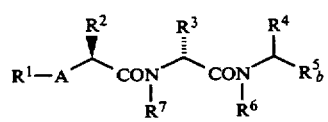   (I-c)

wherein $R^1$, $R^2$, $R^3$, $R^4$, $R^6$, $R^7$ and A are each as defined above, and $R_a^5$ is protected carboxy or protected carboxy(lower)alkyl, or a salt thereof, to a removal reaction of the carboxy-protective group to give a compound of the formula:

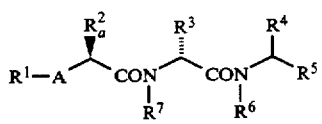   (I-d)

wherein $R^1$, $R^2$, $R^3$, $R^4$, $R^6$, $R^7$ and A are as defined above, and $R_b^5$ is carboxy or carboxy(lower)alkyl, (e) subjecting a compound of the formula:

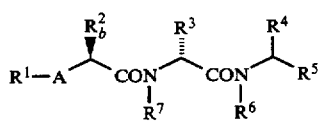   (I-e)

in which $R^1$, $R^3$, $R^4$, $R^5$, $R^6$, $R^7$ and A are each as defined above, and $R_a^2$ is protected imino containing heterocyclic(lower)alkyl optionally substituted by suitable substituent(s), or a salt thereof, to removal reaction of the imino-protective group in $R_a^2$ to give a compound of the formula:

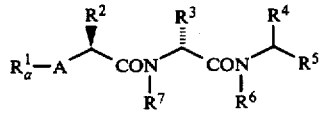   (I-f)

in which $R^1$, $R^3$, $R^4$, $R^5$, $R^6$, $R^7$ and A are each as defined above, and $R_b^2$ is imino containing heterocyclic(lower)alkyl optionally substituted by suitable substituent(s), or a salt thereof; or (f) subjecting a compound of the formula:

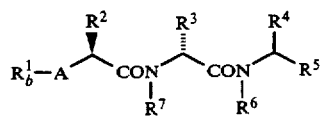   (I-g)

in which $R^2$, $R^3$, $R^4$, $R^5$, $R^6$, $R^7$ and A are each as defined above, and $R_a^1$ is acyl substituted by a protected amino group, or a salt thereof, to removal reaction of the amino-protective group to give a compound of the formula:

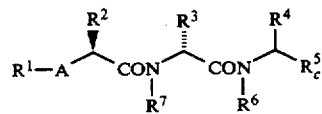   (I-h)

in which $R^2$, $R^3$, $R^4$, $R^5$, $R^6$, $R^7$ and A are each as defined above, and $R_b^1$ is acyl substituted by an amino group, or a salt thereof; or (g) reacting a compound of the formula:

(I-i)

in which $R^1$, $R^2$, $R^3$, $R^4$, $R^6$, $R^7$ and A are each as defined above, and $R_c^5$ is esterified carboxy, or its reactive derivative at the carboxy group, or a salt thereof, with an optionally substituted amine, or a salt thereof to give a compound of the formula:

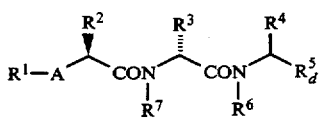

(I-j)

in which $R^1$, $R^2$, $R^3$, $R^4$, $R^6$, $R^7$ and A are each as defined above, and $R_d^5$ is amidated carboxy, or a salt thereof, or (h) acylating the amino group in $R_b^1$ of a compound of the formula:

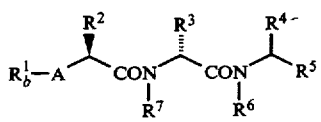

(I-h)

in which $R^1_b$, $R^2$, $R^3$, $R^4$, $R^5$, $R^6$, $R^7$ and A are each as defined above, or a salt thereof, to give a compound of the formula:

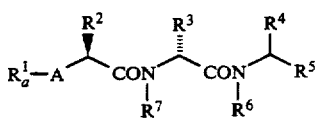

(I-g)

in which $R_a^1$, $R^2$, $R^3$, $R^4$, $R^5$, $R^6$, $R^7$ and A are each as defined above, or a salt thereof; or (i) subjecting a compound of the formula:

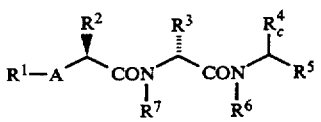

(I-k)

in which $R^1$, $R^2$, $R^3$, $R^5$, $R^6$, $R^7$ and A are each as defined above, and $R_c^4$ is protected carboxy(lower)alkyl, or a salt thereof, to a removal reaction of the carboxy-protective group in $R^4_c$ to give a compound of the formula:

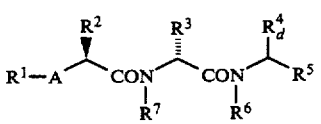

(I-l)

in which $R^1$, $R^2$, $R^3$, $R^5$, $R^6$, $R^7$ and A are each as defined above, and $R_d^4$ is carboxy(lower)alkyl, or a salt thereof, (j) subjecting a compound of the formula:

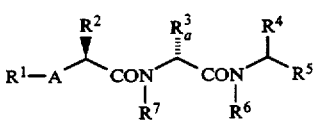

(I-m)

wherein $R^1$, $R^2$, $R^4$, $R^5$, $R^6$, $R^7$ and A are each as defined above, and $R_a^3$ is protected imino containing heterocyclic(lower)alkyl optionally substituted by suitable substituent(s), or a salt thereof, to a removal reaction of the imino-protective group in $R_a^3$ to give a compound of the formula:

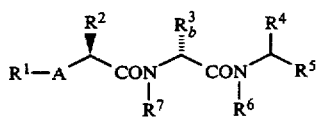

(I-n)

wherein $R^1$, $R^2$, $R^4$, $R^5$, $R^6$, $R^7$ and A are each as defined above, and $R_b^3$ is imino containing heterocyclic(lower)alkyl optionally substituted by suitable substituent(s), (k) subjecting a compound of the formula:

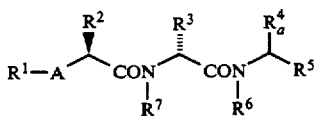

(I-o)

in which $R^1$, $R^2$, $R^3$, $R^5$, $R^6$, $R^7$ and A are each as defined above, and $R_a^4$ is protected amino(lower)alkyl or protected imino containing heterocyclic(lower)alkyl optionally substituted by suitable substituent(s), or a salt thereof, to removal reaction of the amino or imino-protective group in $R_a^4$ to give a compound of the formula:

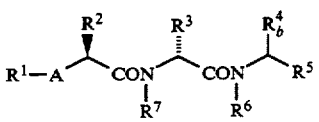

(I-p)

in which $R^1$, $R^2$, $R^3$, $R^5$, $R^6$, $R^7$ and A are each as defined above, and $R_b^4$ is amino(lower)alkyl or imino containing heterocyclic(lower)alkyl optionally substituted by suitable substituent(s), or a salt thereof.

8. A pharmaceutical composition which comprises a compound of claim 1 or a pharmaceutically acceptable salt thereof and a pharmaceutically acceptable carrier or excipient.

9. A process for preparing a pharmaceutical composition which comprises admixing a compound of claim 5 or pharmaceutically acceptable salts thereof with a pharmaceutically acceptable carrier or excipient.

10. A compound of claim 1 or pharmaceutically acceptable salts thereof for use as a medicament.

11. A compound of claim 1 or pharmaceutically acceptable salts thereof for use as an endothelin antagonistic agent.

12. A method for treating endothelin mediated diseases which comprises administering a compound of claim 1 pharmaceutically acceptable salts thereof to human being or animals.

* * * * *